(12) United States Patent
Kimura

(10) Patent No.: US 10,282,879 B2
(45) Date of Patent: May 7, 2019

(54) INFORMATION PROCESSING APPARATUS AND INFORMATION PROCESSING METHOD

(71) Applicant: SONY CORPORATION, Tokyo (JP)

(72) Inventor: Natsuki Kimura, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/551,101

(22) PCT Filed: Apr. 13, 2016

(86) PCT No.: PCT/JP2016/001999
§ 371 (c)(1),
(2) Date: Aug. 15, 2017

(87) PCT Pub. No.: WO2016/166975
PCT Pub. Date: Oct. 20, 2016

(65) Prior Publication Data
US 2018/0033174 A1    Feb. 1, 2018

(30) Foreign Application Priority Data

Apr. 16, 2015 (JP) ................. 2015-083944

(51) Int. Cl.
*G06T 11/60* (2006.01)
*G16H 50/30* (2018.01)
(Continued)

(52) U.S. Cl.
CPC ............. *G06T 11/60* (2013.01); *A61B 5/442* (2013.01); *A61B 5/443* (2013.01); *A61B 5/742* (2013.01);
(Continued)

(58) Field of Classification Search
None
See application file for complete search history.

(56) References Cited

U.S. PATENT DOCUMENTS

2006/0089543 A1* 4/2006 Kim .................. A61B 5/00
600/300
2010/0185064 A1* 7/2010 Bandic ............. A61B 5/0059
600/306
(Continued)

FOREIGN PATENT DOCUMENTS

EP          1875863 A1    1/2008
JP       2012-239768 A   12/2012

OTHER PUBLICATIONS

International Search Report and Written Opinion of PCT Application No. PCT/JP2016/001999, dated Jul. 7, 2016, 12 pages.

*Primary Examiner* — Ryan M Gray
(74) *Attorney, Agent, or Firm* — Chip Law Group

(57) ABSTRACT

There is provided an information processing apparatus including: an acquisition unit that acquires measurement results of a user's skin state; and a presentation unit that displays a chart image configured by arranging a plurality of areas, to which a plurality of items of the measurement results are assigned, having a same shape and a same size in respective directions with a predetermined position used as the center and arranging score images representing scores of the items inside each of the areas so as to have sizes corresponding to the scores and to expand from the predetermined position.

16 Claims, 63 Drawing Sheets

(51) Int. Cl.
    *A61B 5/00*   (2006.01)
    *G06F 19/00*  (2018.01)
    *G06F 19/26*  (2011.01)
    *G06T 11/00*  (2006.01)

(52) U.S. Cl.
    CPC .............. *A61B 5/744* (2013.01); *G06F 19/00* (2013.01); *G06F 19/26* (2013.01); *G06F 19/321* (2013.01); *G06T 11/001* (2013.01); *G16H 50/30* (2018.01); *G06T 2207/10024* (2013.01); *G06T 2210/41* (2013.01)

(56) References Cited

U.S. PATENT DOCUMENTS

| | | | |
|---|---|---|---|
| 2011/0050725 A1* | 3/2011 | Seo ........................ | A61B 5/021 |
| | | | 345/632 |
| 2011/0054269 A1* | 3/2011 | Lee ......................... | A61B 5/00 |
| | | | 600/300 |
| 2012/0154402 A1* | 6/2012 | Mital ..................... | G06T 11/206 |
| | | | 345/440 |
| 2015/0379392 A1* | 12/2015 | Shigyo ................... | G06N 3/006 |
| | | | 345/619 |
| 2016/0210764 A1* | 7/2016 | Gomi ..................... | A45D 44/00 |
| 2016/0262624 A1* | 9/2016 | Nakajima .............. | A61B 5/444 |

* cited by examiner

FIG. 1
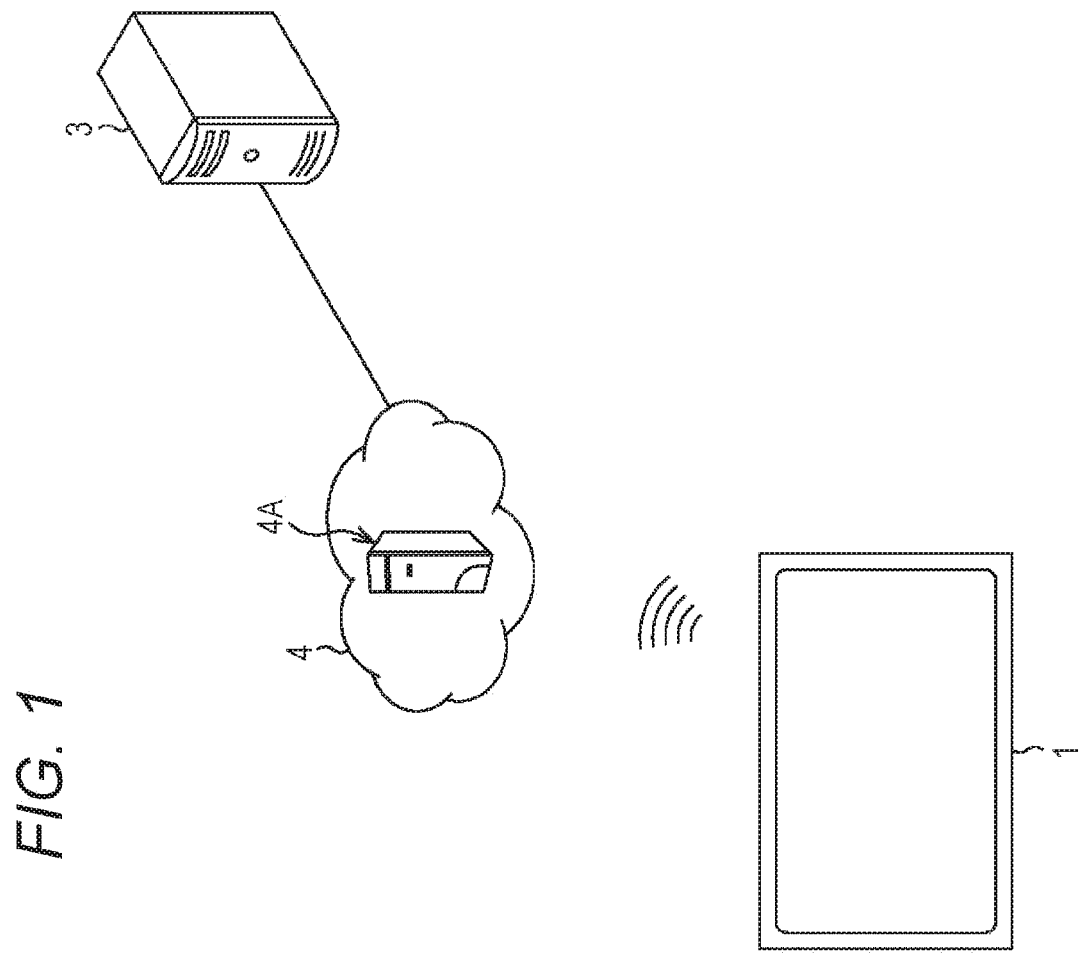
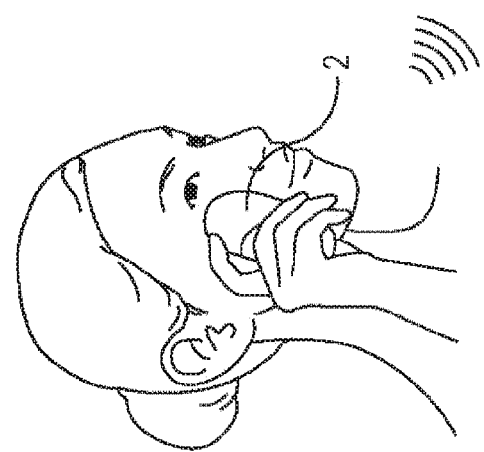

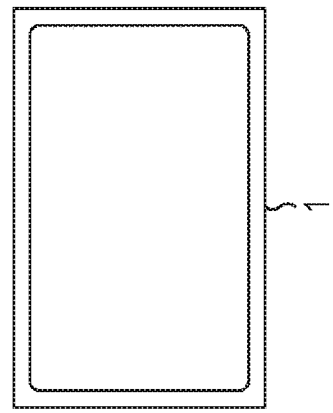
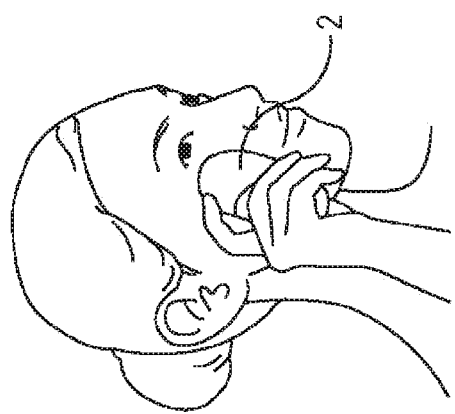
FIG. 53

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2016/001999 filed on Apr. 13, 2016, which claims priority benefit of Japanese Patent Application No. JP 2015-083944 filed in the Japan Patent Office on Apr. 16, 2015. Each of the above-referenced applications is hereby incorporated herein by reference in its entirety.

TECHNICAL FIELD

The present technology relates to an information processing apparatus, an information processing method, and a program, and more particularly, to an information processing apparatus, an information processing method, and a program enabling checking the result of measurement of a skin state in an intuitive and easy manner.

BACKGROUND ART

There are technologies for measuring a skin state by analyzing a skin image acquired by imaging skin through image processing. A person taking a measurement of a skin state images a measurement portion by bringing a measuring instrument in which an imaging device is mounted into contact with the face of a measurement target person or the like.

After the measurement of the skin state, the measurement target person checks a result of the measurement by viewing a screen displayed on a display or the like. On the display screen of measurement results, results of the measurements of items such as a spot state, a texture state, and a pore state are displayed using numbers, a line graph, a radar chart, or the like.

SUMMARY

Some embodiments relate to an apparatus for displaying a first image representing multiple parameters of biological information, the apparatus comprising: circuitry configured to receive data values for the multiple parameters and prepare first image data that, when rendered on a display, forms from the first image data an image of a living plant, wherein the multiple parameters are represented on the display as portions of the living plant. Additional embodiments relate to a data storage device containing machine-readable instructions that, when executed by a processor that is in communication with a display of an apparatus, adapt the apparatus to: receive data values corresponding to multiple parameters of human skin quality; prepare first image data from the received data values; form from the first image data a first image; and render the first image on the display, wherein the multiple parameters are represented on the display as portions of a living plant.

Technical Problem

A display method in related art using numbers, a line graph, a radar chart, or the like employs a theoretical and mathematical representation, and it is difficult for a measurement target person to intuitively understand whether a measurement result is good or bad. In addition, even in case of a good result, it is difficult to arouse a feeling of delight or the like.

It is desirable to enable checking the result of measurement of a skin state in an intuitive and easy manner.

Solution to Problem

An information processing apparatus of one embodiment of the present technology includes: an acquisition unit that acquires information representing measurement results of a user's skin state; and presentation unit that displays a chart image configured by arranging a plurality of areas, to which a plurality of items of the measurement results are assigned, having a same shape and a same size in respective directions with a predetermined position used as the center and arranging score images representing scores of the items inside each of the areas so as to have sizes corresponding to the scores and to expand from the predetermined position.

The presentation unit may display the score images arranged inside each of the areas in mutually-different colors.

The presentation unit may display the chart image such that shapes of the score images representing mutually-different scores are almost similar shapes.

The presentation unit may display the chart image in which information representing a reference score is arranged inside each of the areas.

The presentation unit may display the chart image in which the plurality of areas are arranged with a display area of predetermined information included in the measurement results disposed at the center.

The presentation unit may display information representing a comprehensive evaluation of the user's skin state in the display area.

The presentation unit may change the number of the areas configuring the chart image in accordance with a change in the number of the items of which the scores are displayed.

The presentation unit may display a plurality of the chart images to be aligned in measurement order.

The presentation unit may display the chart images above images of bar shapes having heights corresponding to comprehensive evaluations of the user's skin state.

The presentation unit may display the chart image together with information relating to a life habit of the user.

The presentation unit may display the chart image arranged above an image of a bar shape having a height corresponding to a comprehensive evaluation of the user's skin state above a boundary image representing a boundary of areas and displays a graph image representing the life habit of the user using a bar graph at a position with the boundary image on an extending line of the image having the bar shape interposed therebetween.

The presentation unit may display a plurality of the chart images representing measurement results of skin states of mutually-different users on a same screen.

The presentation unit may display the plurality of the chart images to be aligned in order of better measurement results of the skin states.

The areas configuring the chart image may be areas having approximately petal shapes.

According to one embodiment of the present technology, information representing measurement results of a user's skin state is acquired, and a chart image is displayed which is configured by arranging a plurality of areas, to which a plurality of items of the measurement results are assigned, having a same shape and a same size in respective directions with a predetermined position used as the center and arranging score images representing scores of the items inside each of the areas so as to have sizes corresponding to the scores and to expand from the predetermined position.

Advantageous Effects of Invention

According to an embodiment of the present technology, a result of the measurement of a skin state can be checked in an intuitive and easy manner.

The effects described here are not necessarily limited thereto, but an effect disclosed in the present disclosure may be present.

BRIEF DESCRIPTION OF DRAWINGS

FIG. 1 is a diagram that illustrates an example of the configuration of a skin analyzing system according to an embodiment of the present technology.

FIG. 53 is a diagram that illustrates another example of the configuration of the skin analyzing system.

DESCRIPTION OF EMBODIMENTS

Figure 2A:
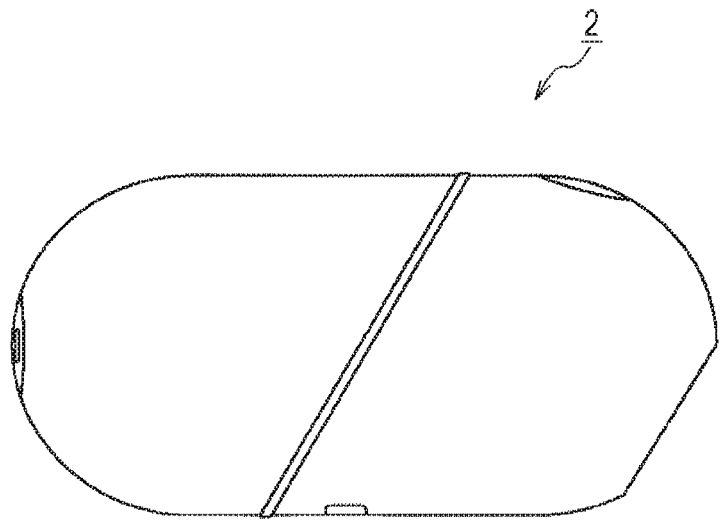
FIGS. 2A and 2B are diagrams that illustrate the external view of a skin measuring instrument.

Hereinafter, embodiments of the present technology will be described. The description will be presented in the following order.

First Embodiment (Example in Which Skin State Is Analyzed by Server)
1. Configuration of Skin Analyzing System
2. Example of Display of Measurement Result Display Screen.
3. Configuration of Each Apparatus
4. Operation of Each Apparatus
Second Embodiment (Example in Which Skin State Is Analyzed by Information Processing Terminal)
Third Embodiment (Example in Which Measurement Result of Plurality of Users Is Displayed)
Modified Example
1. Example of Display Executed in Another Equipment
2. Other Example
«First Embodiment»
<1. Configuration of Skin Analyzing System>

FIG. 1 is a diagram that illustrates an example of the configuration of a skin analyzing system according to an embodiment of the present technology.

The skin analyzing system illustrated in FIG. 1 is configured by: an information processing terminal 1; a skin measuring instrument 2; and an analysis server 3. The information processing terminal 1 and the analysis server 3 are interconnected through a network 4 such as the Internet. The information processing terminal 1 is connected to the network 4 through a relay apparatus 4A such as a Wi-Fi (registered trademark) router.

The information processing terminal 1 and the skin measuring instrument 2 are interconnected through wireless communication such as a wireless Local Area Network (LAN). The information processing terminal 1 and the skin measuring instrument 2 may be interconnected through wired communication using a Universal Serial Bus (USB) cable or the like. In addition, the skin measuring instrument 2 may be directly connected to the network 4 so as to enable the skin measuring instrument 2 and the analysis server 3 to be communicable with each other.

The skin analyzing system illustrated in FIG. 1 is used by a user, mainly by himself, for measuring his skin state and checking a measurement result. The user is a person measuring the skin state and is a measurement target person as well. The measurement of the skin state may be taken through a third-party person such as a beauty advisor.

The information processing terminal 1 is a tablet-type mobile terminal. In a casing of the information processing terminal 1, a display such as a Liquid Crystal Display (LCD) is disposed. In the display, a touch panel is disposed. The user can operate the display by directly touching a button or the like displayed on the display using his finger. Any other mobile terminal such as a personal computer, a smartphone, a mobile phone, or a Head Mounted Display (HMD) may be configured to be used as the information processing terminal 1.

The information processing terminal 1 acquires a skin image captured by the skin measuring instrument 2. The skin image is an image in which a skin of a predetermined position such as a user's face is projected in an enlarged scale. A skin image of a point to be measured such as a forehead, a cheek, or a mouth is acquired by the information processing terminal 1.

Not a narrow range such as a forehead, a cheek, or a mouth but the whole face may be set as a measurement point. In such a case, an image, in which the user's whole face is projected, that is captured by a camera that capable of imaging the whole face is acquired by the information processing terminal 1 as a skin image.

The skin measuring instrument 2 is an electronic device of a degree of a size that can be held by a user using one hand. In a skin measuring instrument 2, various sensors such as an imaging device and a body temperature sensor are disposed. Here, the configuration of the skin measuring instrument 2 will be described.

Figure 2B:
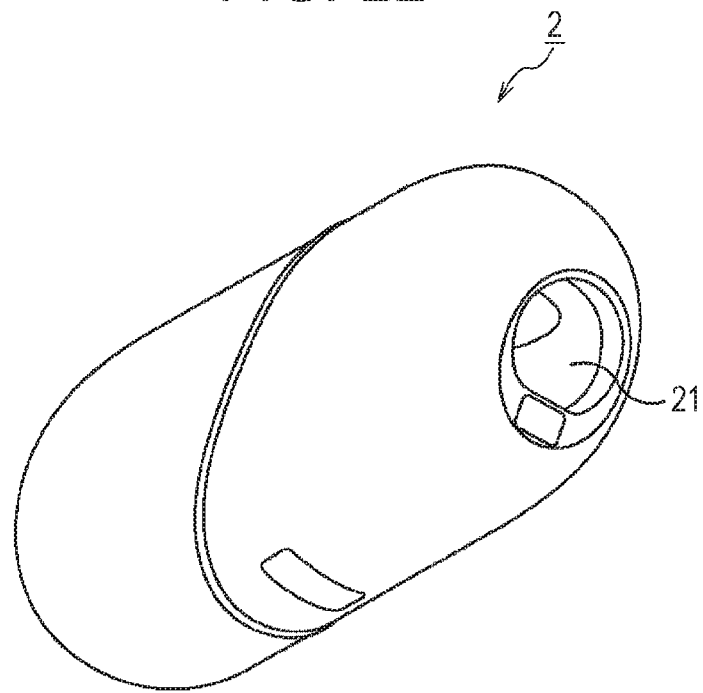

FIGS. 2A and 2B are diagrams that illustrate the external view of the skin measuring instrument 2.

As illustrated in FIG. 2A, the skin measuring instrument 2 has a casing having a horizontally-long elliptic shape when seen in a side view. At a position slightly deviating from an apex of the right end of the casing, a flat face is formed, and, in this flat face, as illustrated in FIG. 2B, a hole portion 21 having an approximately circular shape is formed. A portion of the casing of the skin measuring instrument 2 other than the periphery of the hole portion 21 is formed as a curved face as a whole.

Inside the hole portion 21, a lighting unit that emits light toward the outer side of the hole portion 21, an imaging device that receives reflected light and executes imaging, and the like are disposed. A user, when measuring his skin state, executes imaging by bringing hole portion 21 into contact with a measurement portion.

Figure 3:
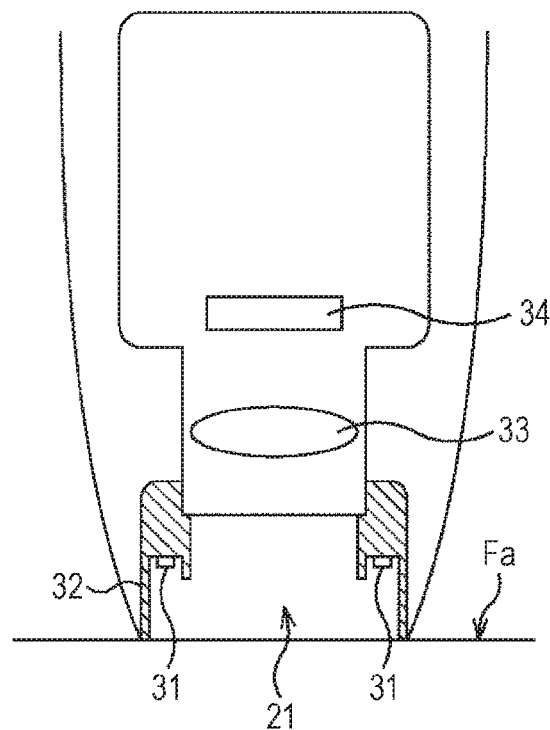
FIG. 3 is a cross-sectional view that illustrates an example of the internal configuration of the skin measuring instrument.

FIG. 3 is a cross-sectional view that illustrates an example of the internal configuration of the skin measuring instrument 2.

The skin measuring instrument 2 includes: lighting units 31; a cylinder unit 32; a lens 33; and an imaging device 34. The lens 33 and the imaging device 34 are disposed inside a casing. The lighting units 31 are disposed inside the cylinder unit 32.

Light emitted from the lighting units 31 arrives at a skin surface Fa. In addition, light reflected by the skin surface Fa passes through the lens 33 and arrives at the imaging device

34. At this time, in a case where the cylinder unit 32 is tightly brought into contact with the skin surface Fa, light emitted from the lighting units 31 can be prevented from leaking to the outside of the skin measuring instrument 2. In addition, light entering the inside of the skin measuring instrument 2 is prevented from arriving at the imaging device 34.

Figure 4:
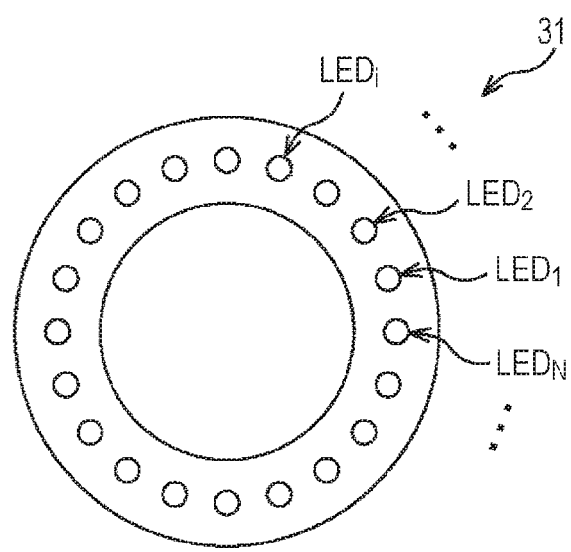
FIG. 4 is a diagram that illustrates an example of the configuration of a lighting unit.

FIG. 4 is a diagram that illustrates an example of the configuration of the lighting unit 31.

The lighting unit 31 is configured by arranging Light Emitting Diode $(LED)_1$ to $LED_N$, which are a plurality of light sources, in a ring pattern. However, the kind of light sources is not limited to the LED. By appropriately arranging a polarizing filter or the like in each LED, imaging can be performed at a different imaging condition such as a changed wavelength.

The information processing terminal 1 illustrated in FIG. 1 transmits a skin image acquired from the skin measuring instrument 2 having such a configuration to the analysis server 3, thereby analyzing the skin state. A plurality of skin images captured at mutually-different conditions are transmitted to the analysis server 3.

The analysis server 3 measures the skin state of a user based on the skin images transmitted from the information processing terminal 1. The analysis server 3 transmits information representing a result of the measurement of the skin state to the information processing terminal 1. For example, states of a plurality of items of the skin such as a texture, a pore, a spot, and a tone are measured. The analysis server 3 analyzes the skin images through image processing and serves as an information processing apparatus that measures a skin state.

The information processing terminal 1 receives information transmitted from the analysis server 3 and displays a measurement result display screen on the display. The measurement result display screen is a screen that displays a result of the measurement of a skin state. As will be described later, the information processing terminal 1 may be configured to perform the measurement of a skin state and display a measurement result display screen.

<2. Example of Display of Measurement Result Display Screen>

2-1. Example in which One Chart Image is Displayed

Figure 5:
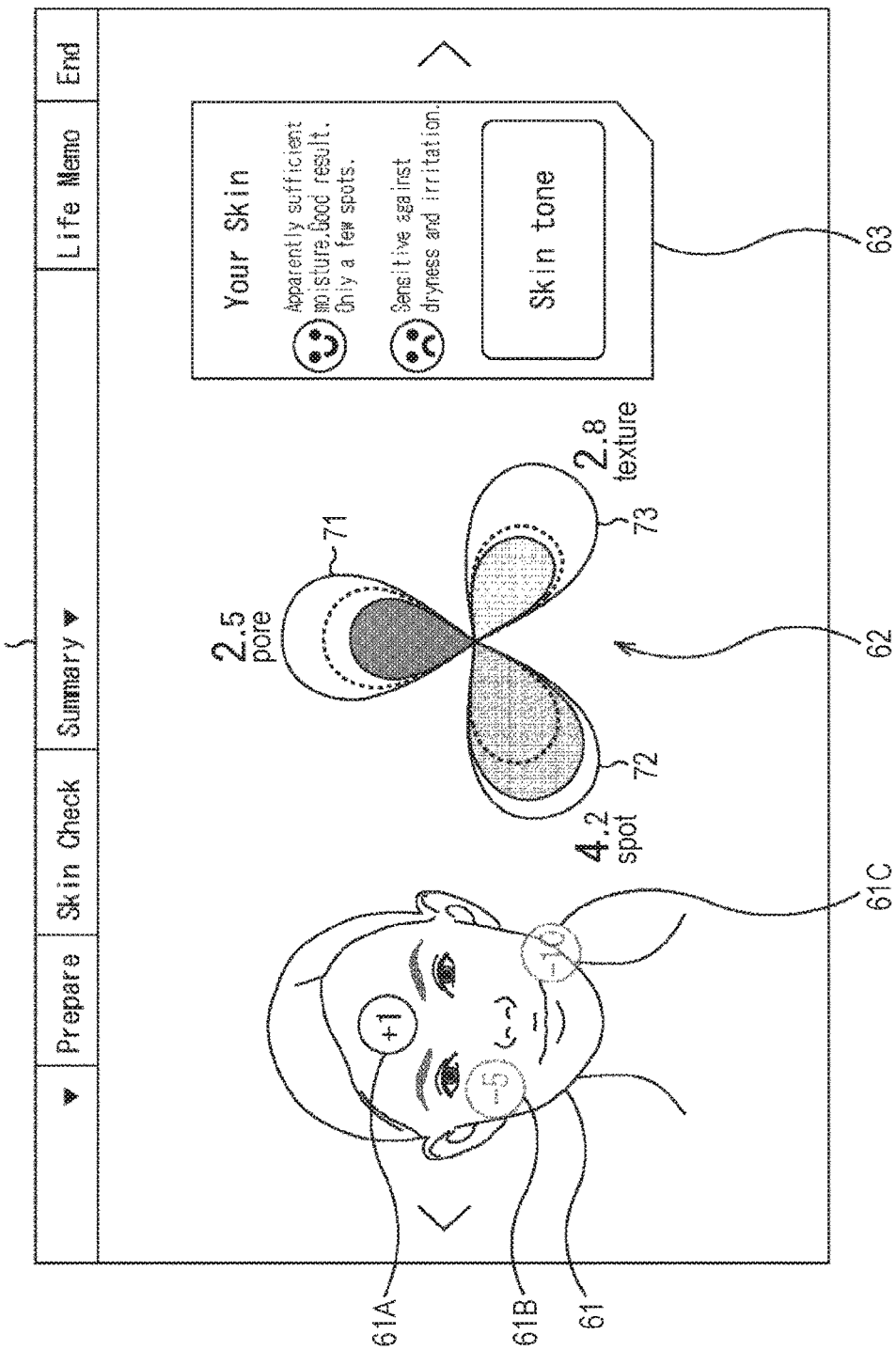
FIG. 5 is a diagram that illustrates a first display example of a measurement result display screen.

FIG. 5 is a diagram that illustrates a first display example of the measurement result display screen.

The measurement result display screen illustrated in FIG. 5 is a screen that is displayed on a display 51 of the information processing terminal 1. The layout of elements configuring the measurement result display screen can be appropriately changed.

On a left side on the measurement result display screen, an illustration 61 of a face of a person facing the front side is displayed. At a position of the forehead on the illustration 61, an icon 61A is displayed, and, at a position of the cheek, an icon 61B is displayed. In addition, at a position of the mouth, an icon 61C is displayed. In the icons 61A to 61C, for example, numbers representing skin ages as a result of the measurement of the skin state of each position are displayed.

When skin images are captured, on the display 51, a screen guiding that the skin images are captured, for example, in order of the forehead, the cheek, and the mouth is displayed. By capturing the skin images according to the screen, the information processing terminal 1 and the analysis server 3 can specify that a certain skin image is acquired by imaging a skin of a certain position.

In the example illustrated in FIG. 5, the skin age measured based on the skin image of the forehead is represented as an age of +1 with respect to the actual age. Before the measurement of the skin, a user registers information of his actual age and the like. In the example illustrated in FIG. 5, a skin age measured based on the skin image of the cheek and a skin age measured based on the skin image of the mouth are respectively represented to be ages of −5 and −10 with respect to the actual age.

At the approximate center of the measurement result display screen, a petal chart 62 that is an image representing the measurement results of items of the skin in a chart form is displayed. The petal chart 62 illustrated in FIG. 5 is an image representing measurement results of a pore state, a spot state, and a texture state. According to the petal chart 62, measurement results of specific positions of the forehead, the cheek, and the mouth may be represented, or a measurement result of the whole face may be represented.

The petal chart 62 is configured by forming petal areas 71 to 73, which are approximately petal-shaped areas, toward three directions. The petal areas 71 to 73 are areas to which measurement results of the pore state, the spot state, and the skin state are assigned.

Above the petal area 71, a number of "2.5" representing a measurement result of the pore state is displayed. On the lower left side of the petal area 72, a number of "4.2" representing a measurement result of the spot state is displayed. On the lower right side of the petal area 73, a number of "2.8" representing a measurement result of the texture state is displayed. As the number is larger, a better measure result is represented. The numbers representing the measurement results may not be displayed. The petal chart 62 will be described later in detail.

On the right side on the measurement result display screen, an area 63 having an approximately vertically-long rectangular shape is formed, and a comment relating to the measurement results and the like are displayed therein. Here, the shape of the area 63 may be configured to have another shape.

Figure 6:
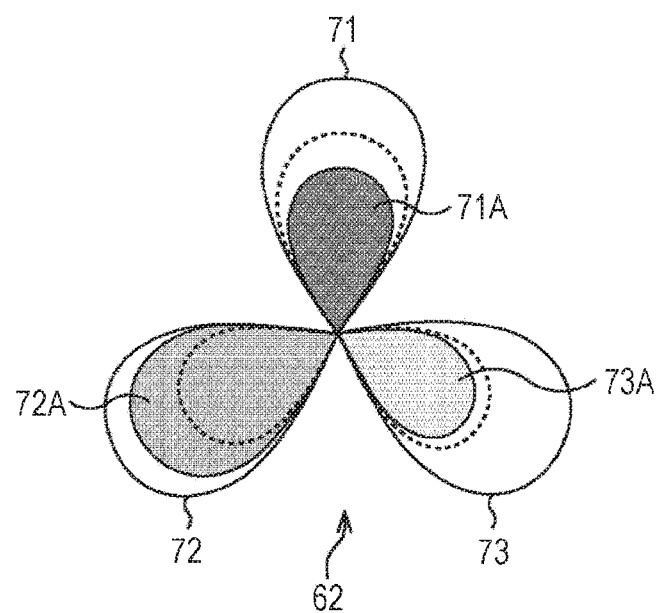
FIG. 6 is a diagram that illustrates a petal chart in an enlarged scale.

FIG. 6 is a diagram that illustrates the petal chart 62 in an enlarged scale.

As described above, the petal chart 62 has the approximately same shape of a petal shape and is configured by forming the petal areas 71 to 73, which are areas having an approximately same size toward three directions with the position of the center of the petal chart 62 used as the reference.

Inside the petal area 71 to which the measurement result of the pore state is assigned, a score image 71A that is an image representing the score (evaluation value) of the pore state is displayed. The score image 71A is an image that is approximately similar to the shape of the petal area 71 and is arranged to expand from the position of the center of the petal chart 62. The score image 71A is displayed in a size corresponding to the score of the pore state. The higher the score is, the larger the score image 71A is displayed.

A dotted line illustrated on the outer side of the score image 71A represents a reference score of the pore state. A score acquired at the time of the previous measurement, a target score set in advance by a user, an average score by age, or the like is displayed as the dotted line as the reference score. In the example illustrated in FIG. 6, the measurement result of the pore state of this time is lower than the reference score.

Figure 7A:
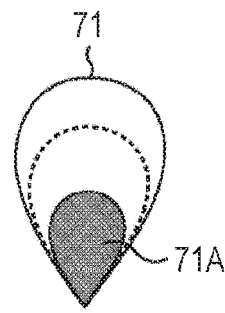
FIGS. 7A, 7B and 7C are diagrams that illustrate an example of display of a score image.
Figure 7B:
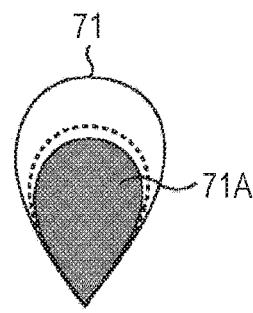
Figure 7C:
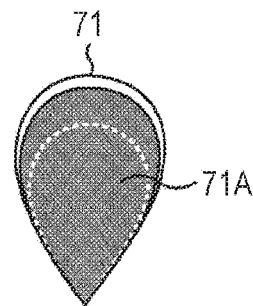

FIGS. 7A, 7B and 7C are diagrams that illustrate an example of display of the score image 71A.

In a case where the same size as that of the petal area 71 is set as a maximal score such as five points, and the score of the pore state, for example, is two points, as illustrated in FIG. 7A, the score image 71A is displayed in a size that is 2/5 of the size of the petal area 71.

In addition, in a case where the score of the pore state is three points, as illustrated in FIG. 7B, the score image 71A is displayed in a size that is 3/5 of the size of the petal area 71. In a case where the score of the pore state is 4.9 points, as illustrated in FIG. 7C, the score image 71A is displayed in a size that is 4.9/5 of the size of the petal area 71.

The display of each of the petal area 72 and the petal area 73 is similar to the display of the petal area 71. In other words, inside the petal area 72 to which the measurement result of a spot state is assigned, a score image 72A is displayed in a size corresponding to the score of the spot state. In the example illustrated in FIG. 6, a measurement result of the pore state of this time represented by the score image 72A is higher than a reference score.

Inside the petal area 73 to which the measurement result of a texture state is assigned, a score image 73A is displayed in a size corresponding to the score of the texture state. In the example illustrated in FIG. 6, a measurement result of the texture state of this time represented by the score image 73A is lower than a reference score.

In a case where the scores of the pore, the spot, and the texture are compared with each other, the petal chart 62 illustrated in FIG. 6 represents that the score of the spot state is the highest, and the score of the pore state and the score of the texture state are almost the same.

For example, the score images 71A to 73A are respectively displayed in mutually-different colors such as a red-based color, a blue-based color, and a green-based color. However, the score images 71A to 73A may be configured to be displayed in a same color. In addition, the petal areas 71 to 73 may be displayed in colors respectively acquired by softening the colors of the score images 71A to 73A or may be displayed in a same color such as a grey color.

Figure 8A:
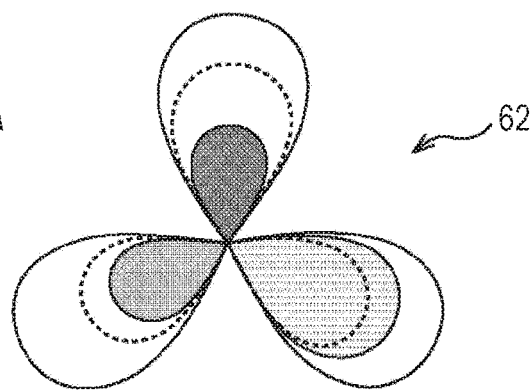
FIGS. 8A, 8B and 8C are diagrams that illustrate an example of display of a petal chart.
Figure 8B:
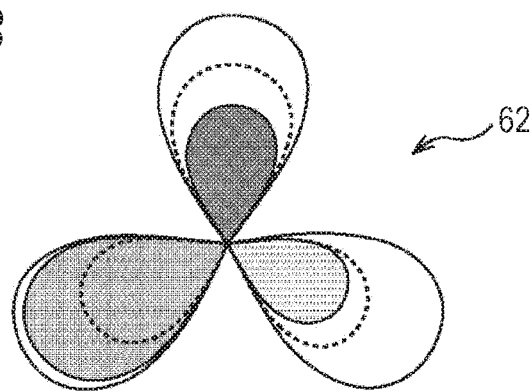
Figure 8C:
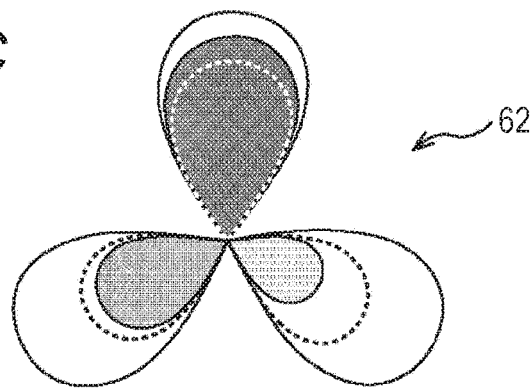

FIGS. 8A, 8B and 8C are diagrams that illustrate an example of display of the petal chart 62.

The petal chart 62 illustrated in FIG. 8A represents that the score of the texture state is the highest, and the score of the pore state and the score of the spot state are almost the same. The petal chart 62 illustrated in FIG. 8B, similarly to that illustrated in FIG. 6, represents that the score of the spot state is the highest, and the score of the pore state and the score of the texture state are almost the same. The petal chart 62 illustrated in FIG. 8C represents that the score of the pore state is the highest, and the score of the spot state and the score of the texture state are almost the same.

In this way, on the measurement result display screen, a petal chart that gives an impression of one flower as a whole to the user and represents a measurement result of each item of the skin state using the size of a petal is displayed. The petal chart represents the measurement results of the skin state using the sizes of petals that are familiar to many users and enables intuitive association of "The flower opens wide"="good result".

Accordingly, the user can check the skin state more intuitively and simply than in a case where the measurement results are displayed simply using numbers, bar graphs or the like. A representation indicating measurement results using numbers, bar graphs, or the like is an inorganic matter, and while there is a possibility that some persons may unconsciously avoid detail checking of the measurement results, by using a representation that becomes easily familiar, such a case can be prevented.

In addition, by using the representation that becomes easily familiar, user's motivation for continuously performing the measurement of the skin state can be raised.

Figure 9:
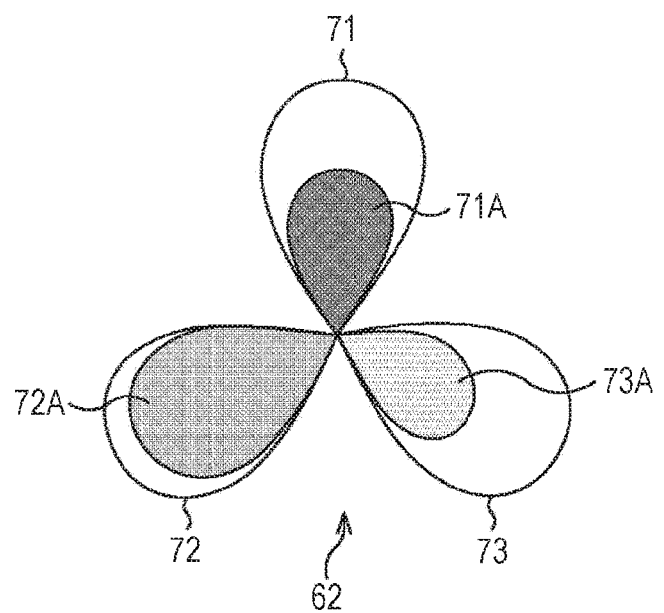
FIG. 9 is a diagram that illustrates an example of display of a petal chart.

In the description presented above, while the reference scores are represented in the petal areas, as illustrated in FIG. 9, the reference scores may be configured not to be displayed.

Figure 10:
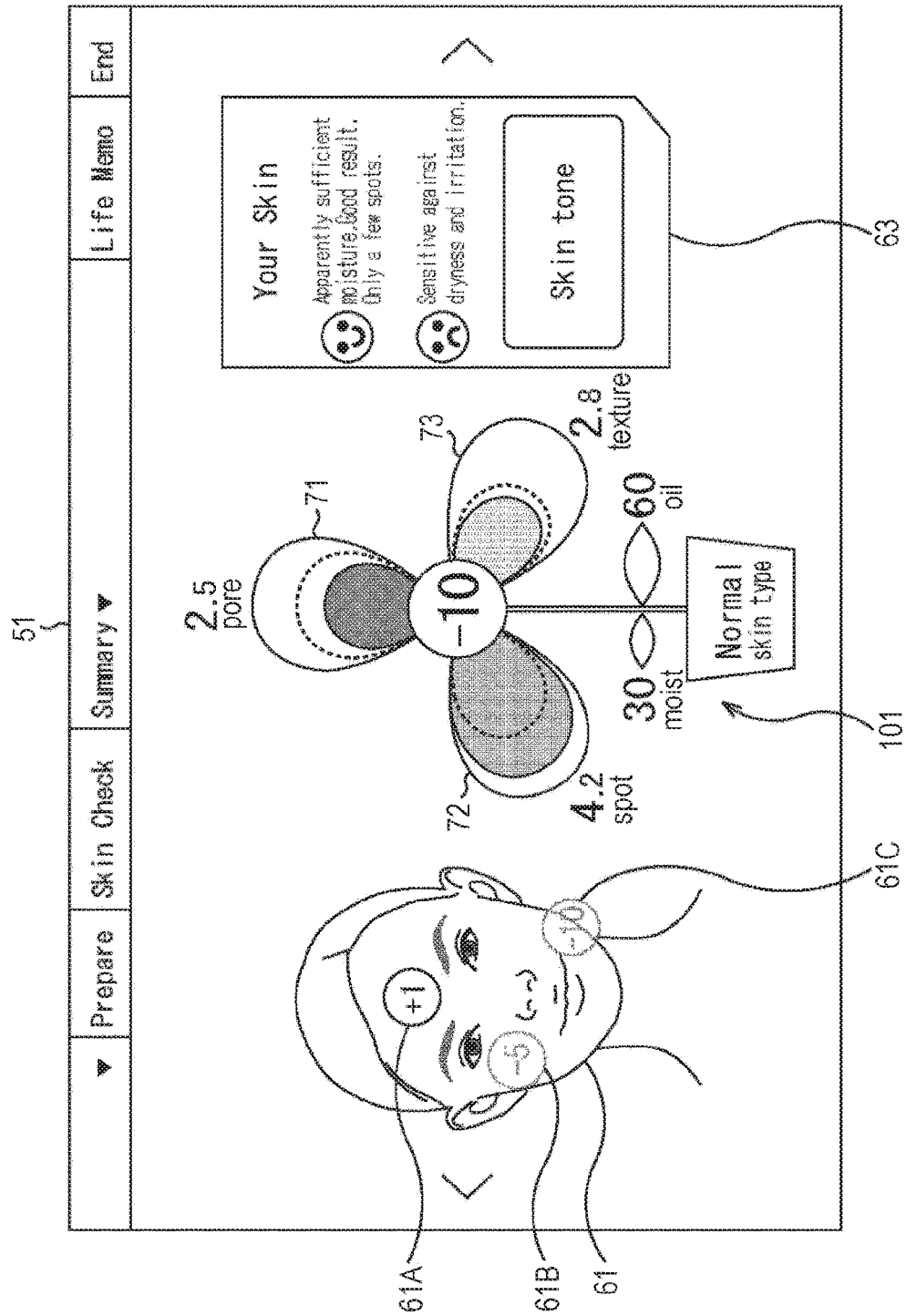
FIG. 10 is a diagram that illustrates a second display example of the measurement result display screen.

FIG. 10 is a diagram that illustrates a second display example of the measurement result display screen.

On the measurement result display screen illustrated in FIG. 10, instead of the petal chart 62 illustrated in FIG. 5, an image 101 is displayed. The image 101 is an image that gives a user an impression of a potted flower.

Among configurations illustrated in FIG. 10, the same reference numeral is assigned to each configuration that is the same as that illustrated in FIG. 5. This similarly applies to FIG. 11 and subsequent drawings. Duplicate description will not be presented as is appropriate.

Figure 11:
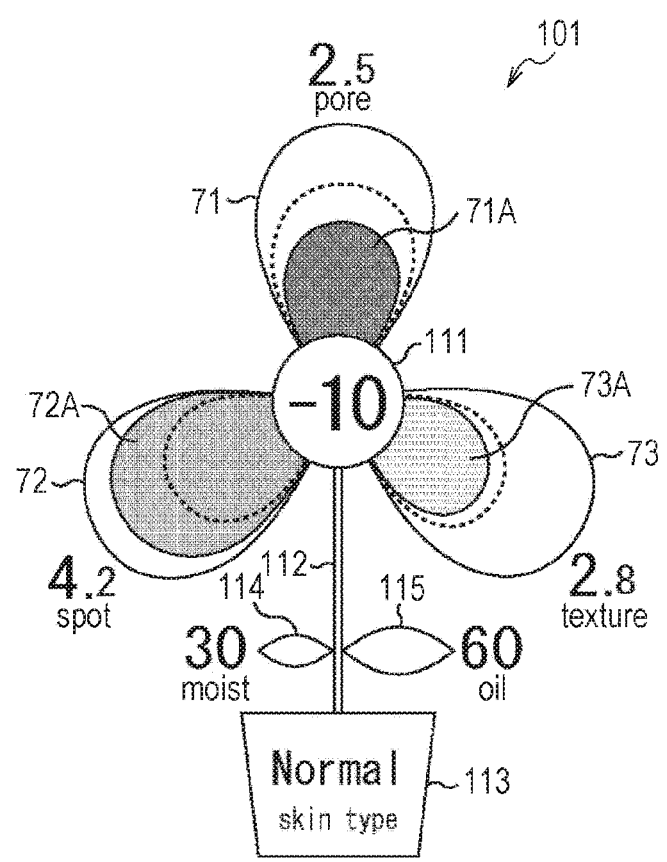
FIG. 11 is a diagram that illustrates an image displayed on the measurement result display screen illustrated in FIG. 10 in an enlarged scale.

FIG. 11 is a diagram that illustrates the image 101 in an enlarged scale.

As illustrated in FIG. 11, petal areas 71 to 73 are formed to have the position of a flower head area 111, which is a circular area smaller than the petal areas 71 to 73, as its center. The flower head area 111 is an area corresponding to a flower head of a flower and, for example, information representing a comprehensive evaluation of the skin state is displayed therein. As above, the petal chart may be configured by the petal areas 71 to 73 and the flower head area 111.

In the example illustrated in FIG. 11, as the information representing the comprehensive evaluation of the skin state, a number of "−10" representing that user's skin age is an age of −10 with respect to the actual age is displayed in the flower head area 111. Here, information other than the skin age may be configured to be displayed, or information displayed in the flower head area 111 may be sequentially switched to other information.

Under the flower head area 111, a stem image 112 that is an image having a bar shape extending in the vertical direction is displayed. Under the stem image 112, a pot image 113 that is an image having a reverse trapezoid shape representing a pot is displayed. In the pot image 113, for example, information of user's skin type is displayed. As skin types, there are a normal skin, an oily skin, a dry skin, a mixed skin, and the like.

At positions close to the pot image 113 that are located to the left and right sides of the stem image 112, leaf images 114 and 115 each having a leaf shape are respectively displayed. The leaf image 114 represents a measurement result of the moist amount of the skin and is displayed in a size corresponding to the moist amount. In the example illustrated in FIG. 11, the measurement result of the moist amount of the skin is assumed to be "30". On the other hand, the leaf image 115 represents a measurement result of the oil amount of the skin and is displayed in a size corresponding to the oil amount. In the example illustrated in FIG. 11, the measurement result of the oil amount of the skin is assumed to be "60".

Generally, the states of the pore, the spot, and the texture change based on states of items such as a moist amount, an oil amount, and the like changing day by day. In other words, the states of the pore, the spot, and the texture are influenced by the states of items such as a moist amount, an oil amount, and the like changing day by day. By displaying the measurement results of the items influencing the states of the pore, the spot, and the texture in forms imitating leaves and displaying the measurement results of the states of the pore, the spot, and the texture using petals, relation among the items can be represented to be easily understood.

In addition, the moist amount and the oil amount of the skin have close relation with the skin type. By arranging the leaf images representing the moist amount and the oil amount of the skin near that image imitating the pot in which the information of the skin type is displayed, such relation can be represented to be easily understood.

Figure 12:
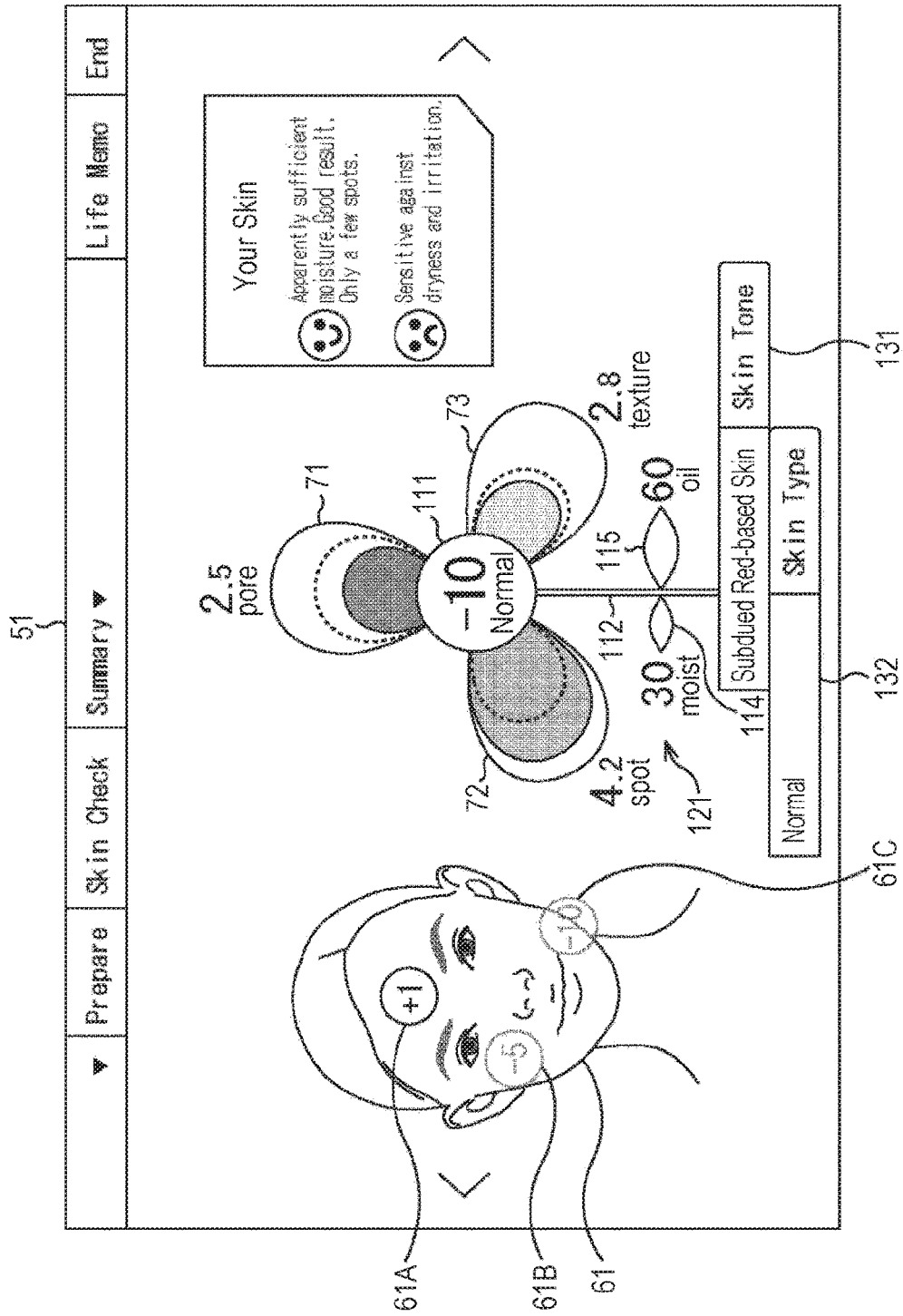
FIG. 12 is a diagram that illustrates a third display example of the measurement result display screen.

FIG. 12 is a diagram that illustrates a third display example of the measurement result display screen.

In an image 121 illustrated in FIG. 12, instead of the pot image 113, areas 131 and 132 that are horizontally-long rectangular areas are arranged to have positions deviating from each other, which is different from the image 101 illustrated in FIG. 10. In the area 131, information relating to a measurement result of the tone of the skin is displayed. In addition, in the area 132, information relating to the measurement result of the skin type is displayed.

Figure 13:
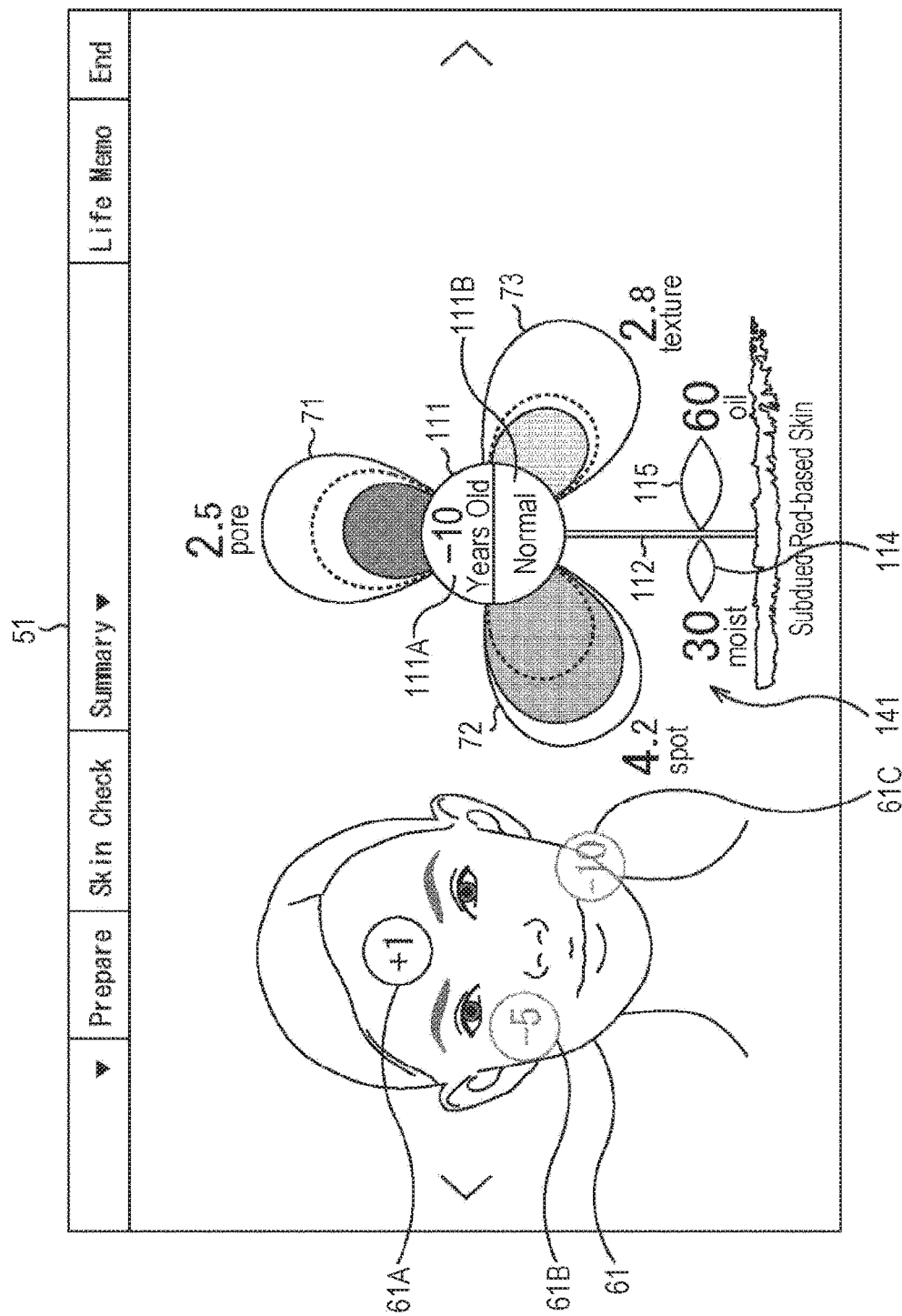
FIG. 13 is a diagram that illustrates a fourth display example of the measurement result display screen.

FIG. 13 is a diagram that illustrates a fourth display example of the measurement result display screen.

In an image 141 illustrated in FIG. 13, instead of the pot image 113, an image representing the ground of soil is displayed, which is different from the image 101 illustrated in FIG. 10. The image representing the ground of the soil, for example, is displayed in a color corresponding to a measurement result of the tone of the skin. In addition, a flower head area 111 of the image 141 is vertically divided into areas 111A and 111B that are semicircular areas. In the area 111A, information relating to a skin age is displayed. In addition, in the area 111B, information relating to the skin type is displayed.

Figure 14:
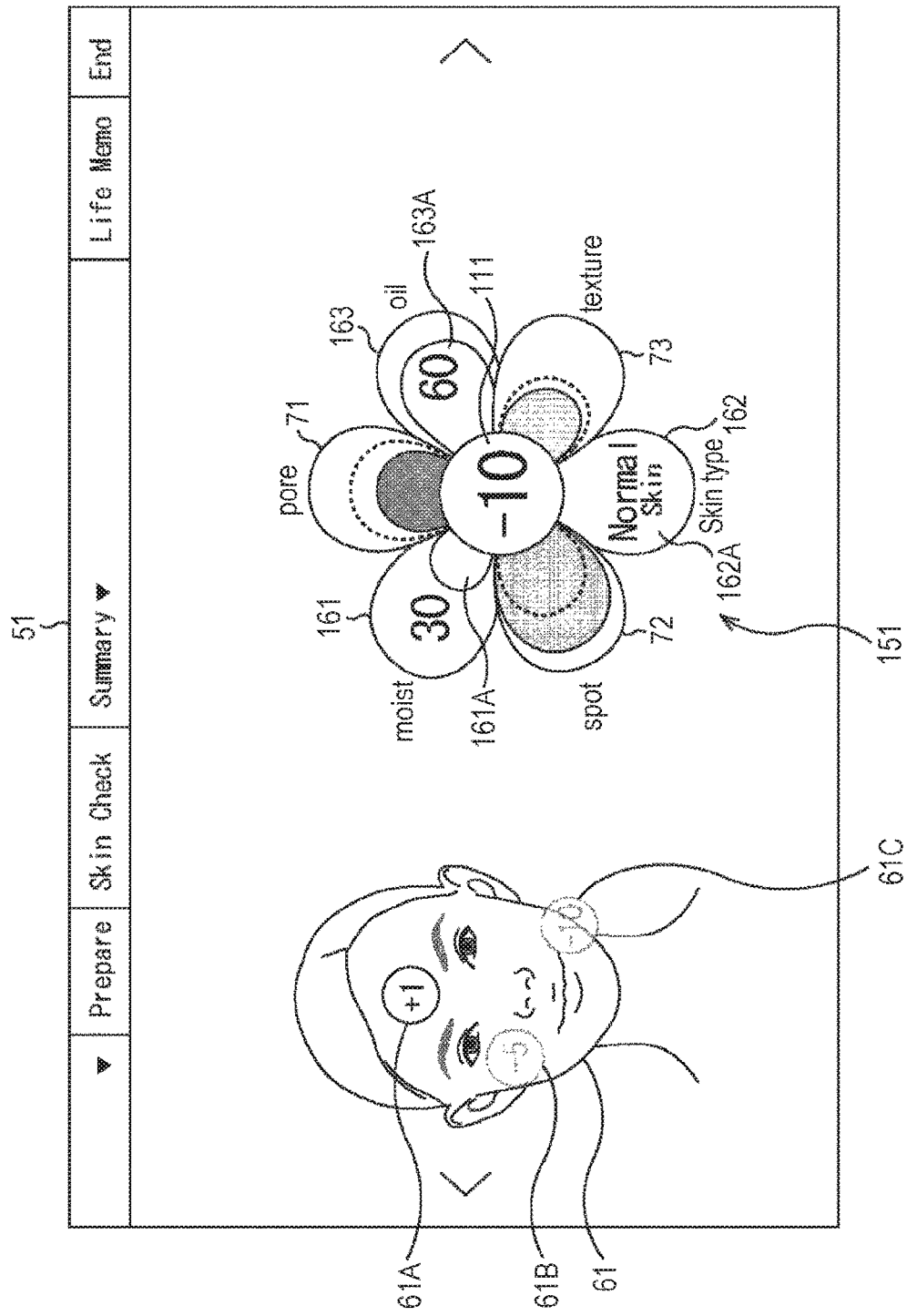
FIG. 14 is a diagram that illustrates a fifth display example of the measurement result display screen.

FIG. 14 is a diagram that illustrates a fifth display example of the measurement result display screen.

A petal chart 151 illustrated in FIG. 14 is configured by forming areas 161 to 163 between a petal area 71 and a petal area 72, between a petal area 72 and a petal area 73, and between a petal area 73 and a petal area 71. The areas 161 to 163 correspond to sepals of a flower. For example, the areas 161 to 163 are displayed in a color different from the colors of the petal areas 71 to 73.

The areas 161 to 163 are areas to which measurement results of the moist amount, the skin type, and the oil amount are assigned. Inside of the area 161, a score image 161A representing a score of the state of the moist amount and a number of "30" representing the score are displayed. Inside the area 162, characters representing a measurement result of the skin type are displayed. Inside the area 163, a score image 163A representing a score of the state of the oil amount and a number of "60" representing the score are displayed.

By displaying the measurement results of items influencing the states of the pore, the spot, and the texture in forms imitating sepals and displaying the measurement results of the states of the pore, the spot, and the texture using petals, as described above, relation among the items can be represented to be easily understood.

Figure 15:
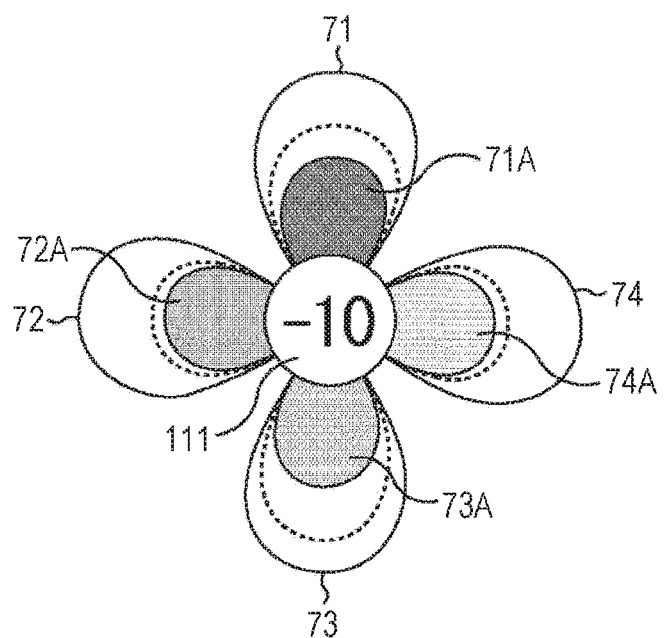
FIG. 15 is a diagram that illustrates an example of display of a petal chart.

FIG. 15 is a diagram that illustrates an example of display of a petal chart.

As illustrated in FIG. 15, the number of items of measurement results represented by one petal chart may be configured to be three or more.

The petal chart illustrated in FIG. 15 is configured, for example, by adding a petal area 74 that is an area to which a measurement result of the state of wrinkles is assigned to petal areas 71 to 73. The petal areas 71 to 74 are arranged toward four directions with the position of a flower head area 111 as the reference. Inside the petal area 74, a score image 74A representing a score of the state of wrinkles is displayed.

The number of items of which measurement results are displayed may be configured to be settable by a user. In such a case, the number of petal areas configuring a petal chart changes according to user's setting.

Figure 16:
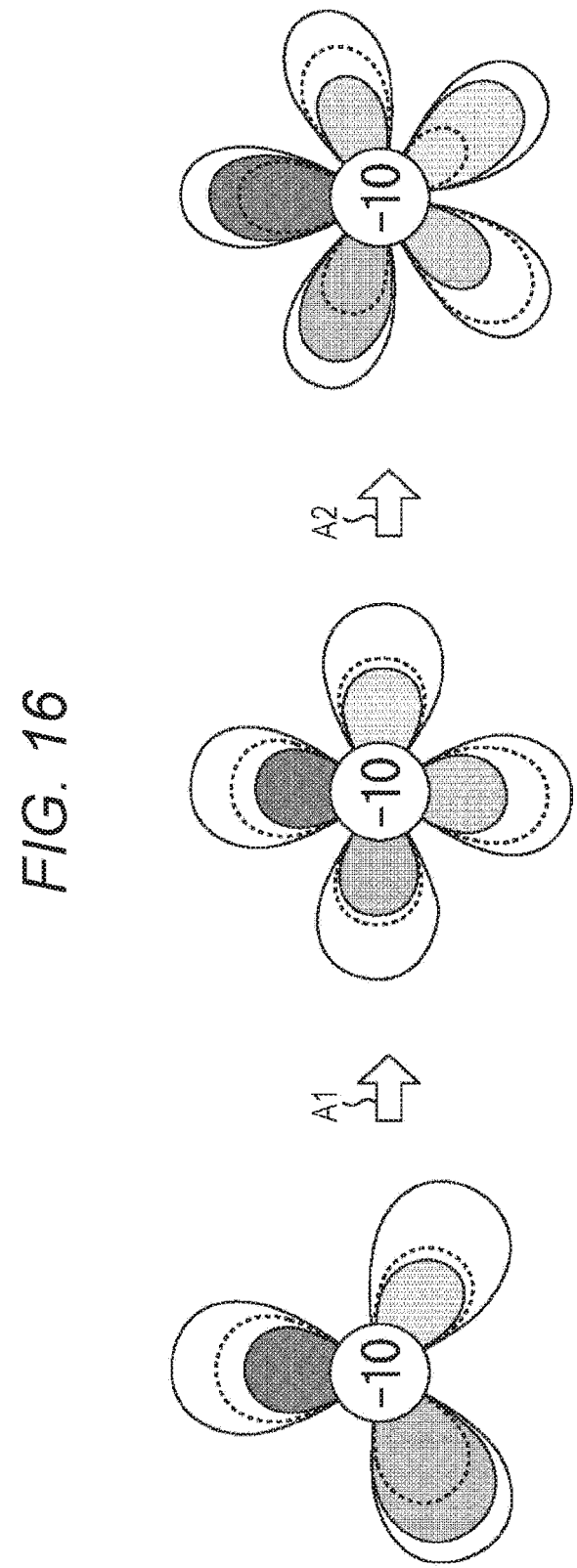
FIG. 16 is a diagram that illustrates an example of conversion of the number of petal areas.

FIG. 16 is a diagram that illustrates an example of conversion of the number of petal areas.

For example, as illustrated on the left side in FIG. 16, in a case where measurement results of three items are set to be displayed, in a case where the number of items is set to be increased by one, as illustrated at the tip of an arrow A1, the petal chart is switched to an image that is configured by four petal areas.

In addition, in a case where measurement results of four items are set to be displayed, in a case where the number of items is set to be increased by one, as illustrated at the tip of an arrow A2, the petal chart is switched to an image that is configured by five petal areas.

The setting of items of which the measurement results are displayed, for example, is performed using a setting menu. On the setting menu, a check box for each item is prepared, and the setting is performed by switching on/off of each check box.

In this way, the number of petal areas configuring the petal chart can be appropriately changed. Accordingly, the user can display and check measurement results of arbitrary items.

Figure 17:
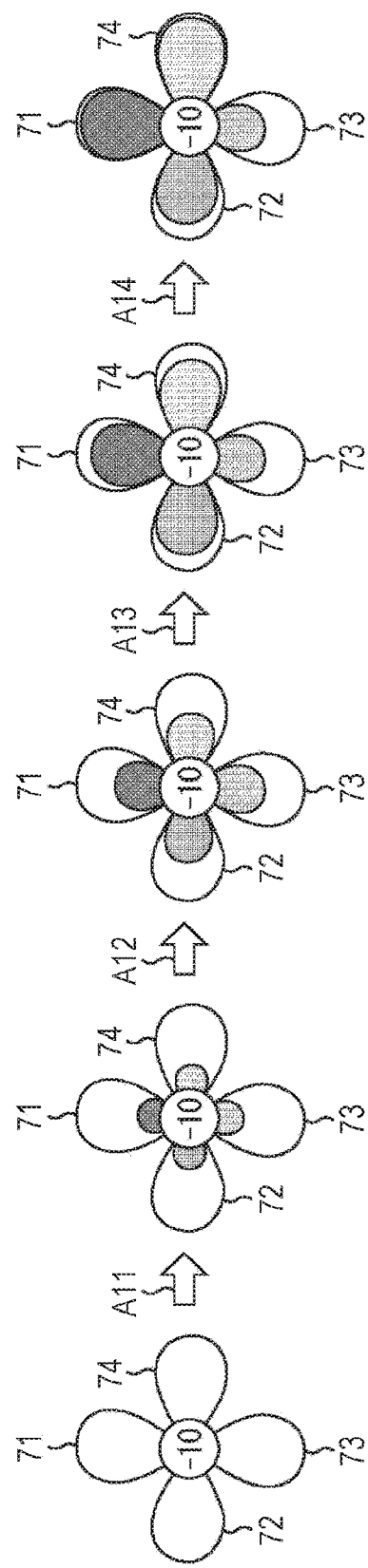
FIG. 17 is a diagram that illustrates an example of an animation immediately after the start of display of a petal chart.

FIG. 17 is a diagram that illustrates an example of an animation immediately after the start of display of a petal chart.

The display of score images immediately after the start of display of the measurement result display screen may be configured to be display of an animation. Here, the display of score images in the petal chart configured by four petal areas will be described.

In this case, as illustrated at the tips of arrows A11 to A14 illustrated in FIG. 17, four score images are displayed to be gradually enlarged until the sizes thereof respectively become sizes corresponding to the scores. A petal chart illustrated at the left end illustrates a state immediately after the start of display. After a predetermined time elapses after the start of display, the score images are in a state illustrated at the tip of the arrow A11.

In addition, when a predetermined time elapses after the display of the petal chart illustrated at the tip of the arrow A11, the states of the score images are in a state illustrated at the tip of the arrow A12. When a predetermine time further elapses from the state, the states of the score images are in a state illustrated at the tip of the arrow A13. When a predetermined time elapses after the display of the petal chart illustrated at the tip of the arrow A13, the states of the score images are in a state illustrated at the tip of the arrow A14.

In this example, the score image 71A of a petal area 71 and the score image 74A of a petal area 74 are gradually enlarged up to the state illustrated at the tip of the arrow A14. In addition, the score image 72A of a petal area 72 is gradually enlarged up to the state illustrated at the tip of the arrow A13. The score image 73A of a petal area 73 is gradually enlarged up to the state illustrated at the tip of the arrow A12.

In FIG. 17, while changes in the state of each score image are illustrated in a stepped manner, actually, the states are continuously changed.

2-2. Example in which Plurality of Petal Charts are Displayed

Figure 18:
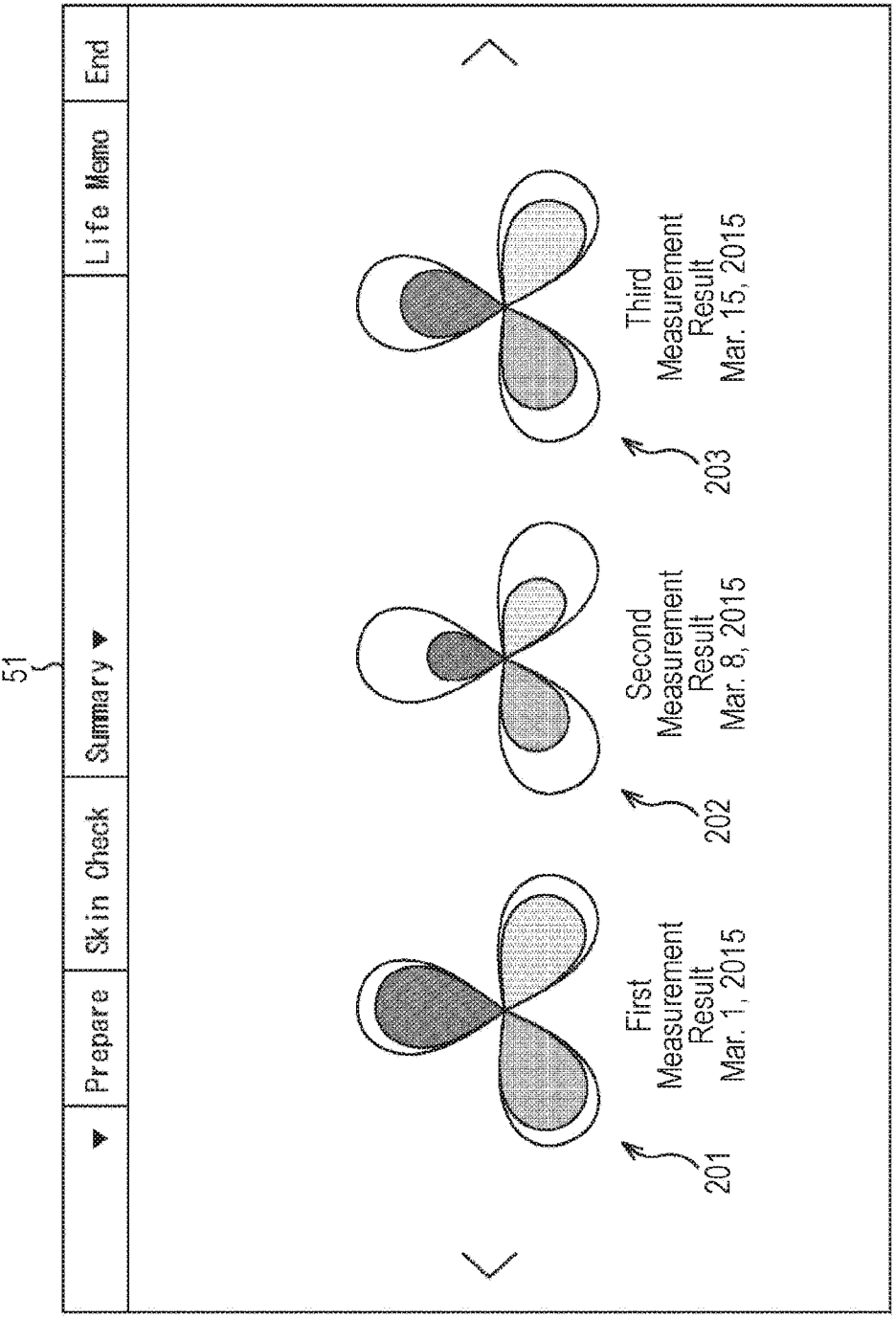
FIG. 18 is a diagram that illustrates a sixth display example of the measurement result display screen.

FIG. 18 is a diagram that illustrates a sixth display example of the measurement result display screen.

On the measurement result display screen illustrated in FIG. 18, a petal chart 201 displayed on the left side is a petal chart that illustrates a measurement result at the first measurement taken on Mar. 1, 2015. A petal chart 202 displayed at the center is a petal chart that illustrates a measurement result at the second measurement taken on Mar. 8, 2015 that is one week later. A petal chart 203 displayed on the right side is a petal chart that illustrates a measurement result at the third measurement taken on Mar. 15, 2015.

In this way, petal charts illustrating measurement results of a plurality of times may be arranged and displayed in order of a time series. From the analysis server 3 to the information processing terminal 1, information representing the measurement results of the plurality of times is transmitted.

A user can check a transition of the skin state based on a change in the size of each score image.

Figure 19:
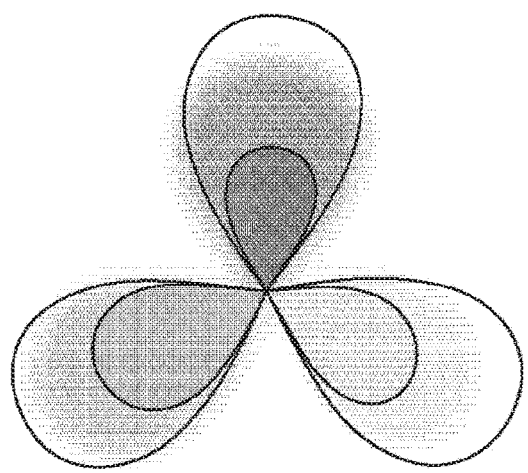
FIG. 19 is a diagram that illustrates an animation of a petal chart.

As illustrated in FIG. 19, measurement results of a plurality of times may be displayed by changing the display of one petal chart by using an animation.

For example, one petal chart is switched from a state representing a first measurement result to a state representing a second measurement result and is additionally switched to a state representing a third measurement result. In FIG. 19, a color represented to be shaded off illustrates that the display of the score image of each petal area is changed. Also in this way, the user can check a transition of his skin state.

Figure 20:
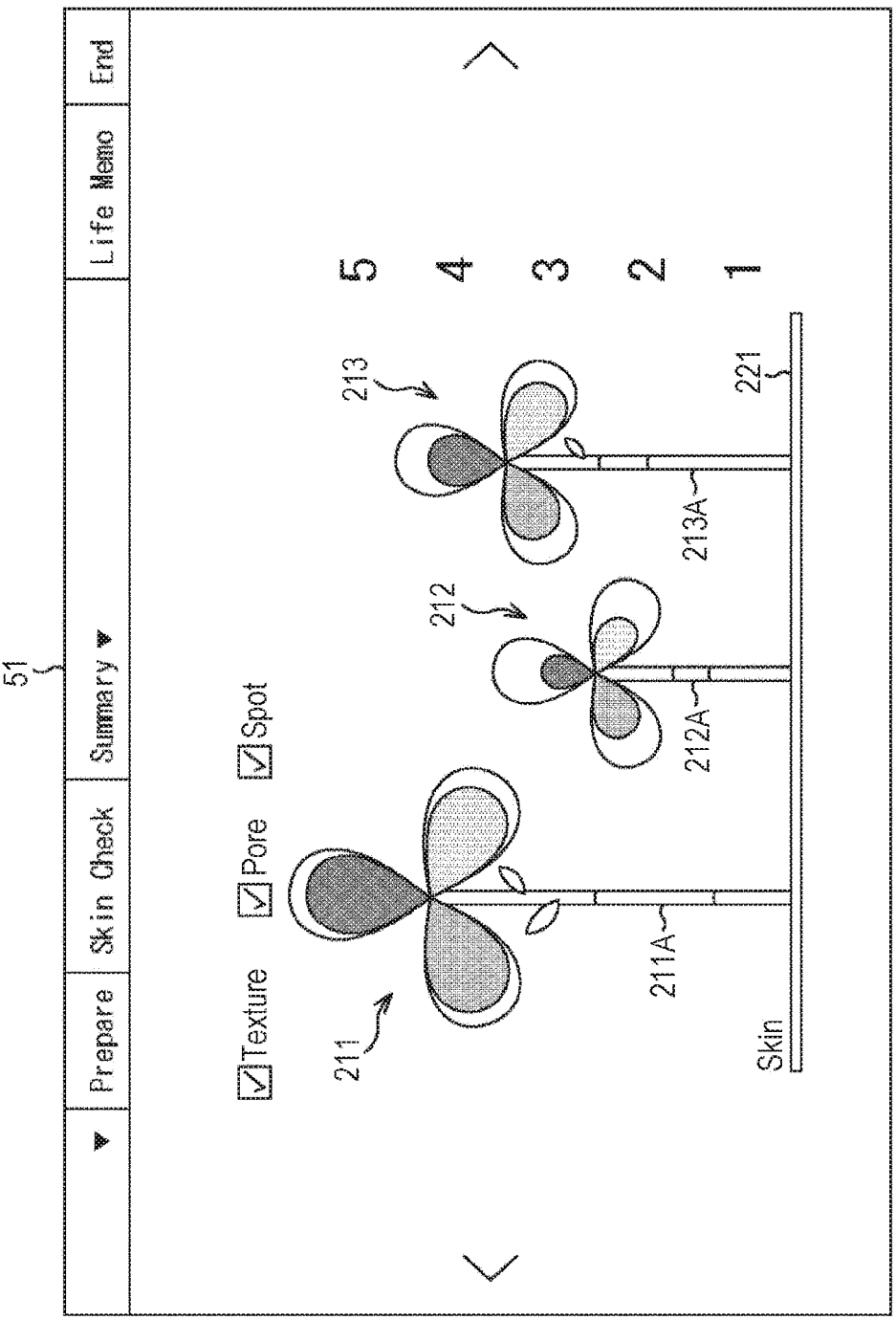
FIG. 20 is a diagram that illustrates a seventh display example of the measurement result display screen.

FIG. 20 is a diagram that illustrates a seventh display example of the measurement result display screen.

In the example illustrated in FIG. 20, petal charts 211 to 213 having mutually-different sizes are aligned and displayed. Similarly to the measurement result display screen illustrated in FIG. 18, a petal chart 211 disposed on the left side represents a first measurement result, and a petal chart 202 disposed at the center illustrates a second measurement result. A petal chart 203 disposed on the right side illustrates a third measurement result.

On the measurement result display screen illustrated in FIG. 20, check boxes of the texture, the pore, and the spot as items of the skin state are horizontally aligned and displayed on the upper side, and all the check boxes are checked as On. Each petal chart illustrates measurement results of the states of the texture, the pore, and the spot.

Under the petal charts 211 to 213, stem images 211A to 213A having mutually-different heights are respectively displayed. The lower ends of the stem images 211A to 213A are in contact with a boundary image 221 that is an image having a shape of a horizontal line.

The sizes of the petal charts 211 to 213 and the heights of the stem images 211A to 213A change according to the measurement results. The sizes of the petal charts 211 to 213, for example, represent differences from previous measurement results.

In this case, the petal chart 212 being smaller than the petal chart 211 represents that a measurement result represented by the petal chart 212 is worse than a measurement result represented by the petal chart 211. In addition, the petal chart 213 being larger than the petal chart 212 represents that a measurement result represented by the petal chart 213 is better than a measurement result represented by the petal chart 212.

The size of the petal chart may be configured to represent a comprehensive evaluation of the skin state.

The heights of the stem images 211A to 213A represent a comprehensive evaluation of the skin state and the like. The higher the comprehensive evaluation of the skin state is, or the higher the evaluation of the skin age is, the higher the heights of the stem images 211A to 213A are displayed.

As the size or the height of the flower changes, a user can intuitively perceive a transition of the skin state. In addition, since a transition of the skin state is represented by the growth of a flower having familiarity, the user can have a feeling of joy or the like when the flower grows. In addition, based on a desire for growing the flower, the user tries to improve the skin state, whereby the motivation can be raised.

Figure 21:
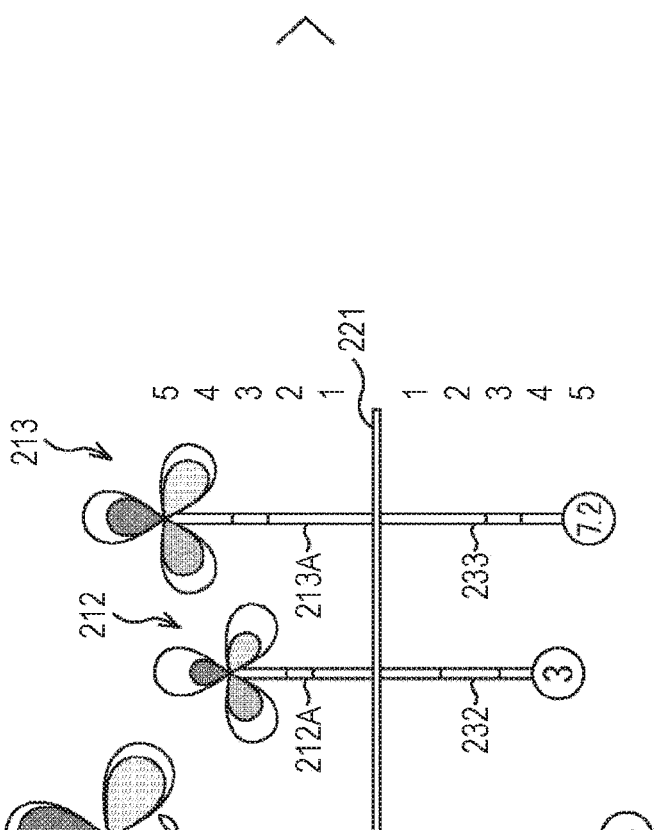
FIG. 21 is a diagram that illustrates an eighth display example of the measurement result display screen.

FIG. 21 is a diagram that illustrates an eighth display example of the measurement result display screen.

In the example illustrated in FIG. 21, on an extending line of a stem image 211A, a root image 231 that is an image having a bar shape corresponding to a root of a flower is displayed with the boundary image 221 described with reference to FIG. 20 being interposed therebetween. Under a stem image 212A, a root image 232 is displayed, and, under a stem image 213A, a root image 233 is displayed. The root images 231 to 233 represent the states of items considered to influence the skin state such as a life habit, a feeling mood, and an environment. Hereinafter, as the items influencing the skin state, the life habit and the feeling mood will be used for description.

Below the measurement result display screen illustrated in FIG. 21, check boxes of sleep, meals, exercise, and stress as items of the life habit are horizontally aligned and displayed, and the check boxes of the sleep, the meals, and the exercise among them are checked as On.

For example, the root image 231 represents the states of the sleep, the meals, and the exercise before a first measurement. In addition, the root image 232 represents the states of the sleep, the meals, and the exercise before a second measurement after the first measurement. The root image 233 represents the states of the sleep, the meals, and the exercise before a third measurement after the second measurement.

Figure 22:
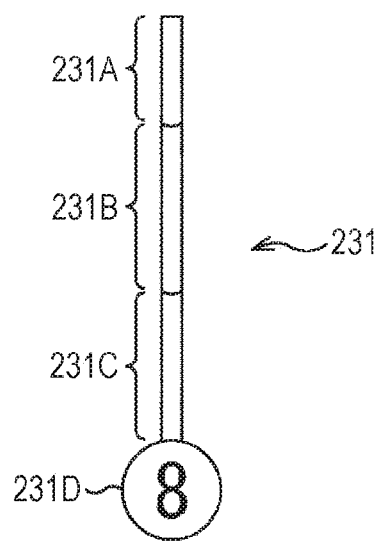
FIG. 22 is a diagram that illustrates a root image in an enlarged scale.

FIG. 22 is a diagram that illustrates the root image 231 in an enlarged scale.

The root image 231 is configured by aligning areas 231A to 231C and arranging a circular area 231D at the end of the area 231C. The areas, for example, are displayed in mutually-different colors.

The areas 231A to 231C respectively represent the scores of the sleep, the meals, and the exercise using lengths thereof. For example, as the state of the sleep is better, and the score thereof is higher, the length of the area 231A to which the item of the sleep is assigned becomes longer. The root image 231 is an image that represents the scores of the life habits in the form of a bar graph.

In this way, the score is acquired for each item of the life habit. In the area 231D, for example, the score of an item of the life habit having a highest score is displayed in a highlighted manner. The area 231D may be displayed in a size corresponding to the score. In addition, a total score of the life habits may be configured to be displayed in the area 231D.

Generally, the skin state is influenced by life habits and a feeling mood and changes according to the life habits and the feeling mood. By representing the skin state as a flower and representing states of items influencing the skin as roots as a group of graphics, the user can observe a casual relation between the skin state and life habits and the like.

In related art, commonly, a measurement result of the skin and information of life habits and the like are displayed without being associated with each other, and, in such display, it is difficult for a user to comprehensively evaluate the skin state including relation with the life habits. By using the representation as illustrated in FIG. 21, the skin state including the relation with the life habits and the like can be comprehensively evaluated.

The scores of items influencing the skin such as life habits, a feeling mood, and the like may be displayed using stem images. Hereinafter, appropriately, information such as life habits, user's feeling mood, and the like considered to influence the skin state will be referred to as a life-log altogether. The life-log may be manually input by the user using a screen displayed on the display 51 or be measured by a wearable device mounted by a user to his body. The life-log measured by the wearable device is transmitted to the information processing terminal 1 and is acquired therein.

Figure 23:
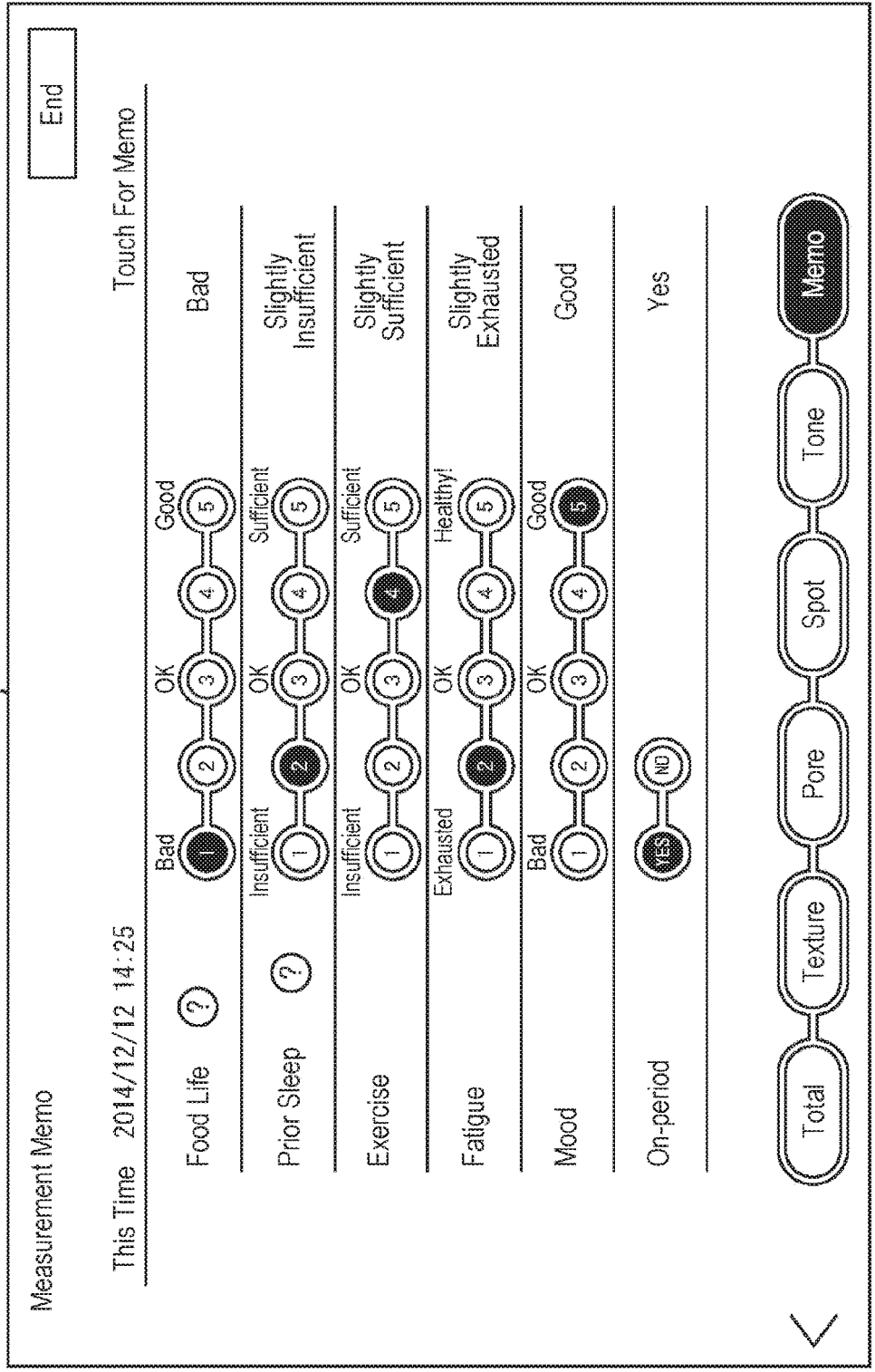
FIG. 23 is a diagram that illustrates an example of an input screen of a life-log.
Figure 24A:
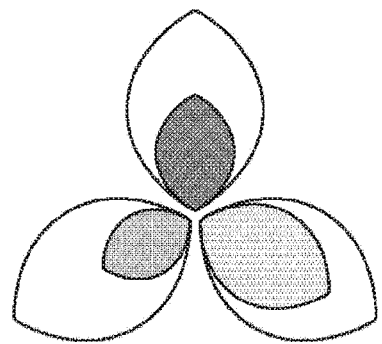
FIGS. 24A, 24B and 24C are diagrams that illustrate modified examples of the petal chart.
Figure 24B:
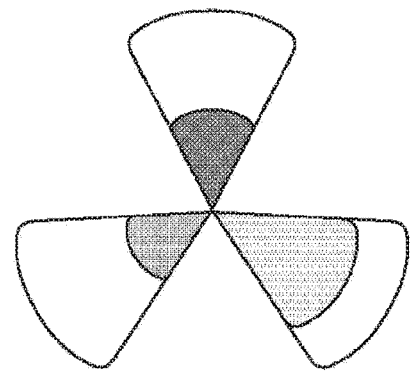
Figure 24C:
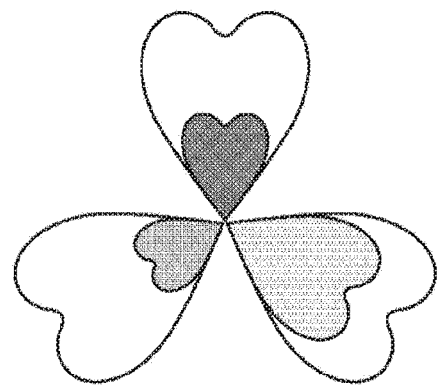

FIG. 23 is a diagram that illustrates an example of an input screen of the life-log.

On the input screen illustrated in FIG. 23, it is configured such that a user can select a score of each of items of a food life (meal), sleep, exercise, fatigue, and a feeling mood. In addition, it can be selected whether or not the user is having her period.

Information relating to the life-log input using such a screen is transmitted from the information processing terminal 1 to the analysis server 3 and is used for an evaluation of life habits and the like. In addition, in a case where scores of life habits and the like are displayed together with the skin state, the life-log may be acquired by the information processing terminal 1 and be transmitted to the analysis server 3.

2-3. Modified Example of Petal Chart

FIGS. 24A, 24B, 24C and 25 are diagrams that illustrate modified examples of the petal chart.

Figure 25A:
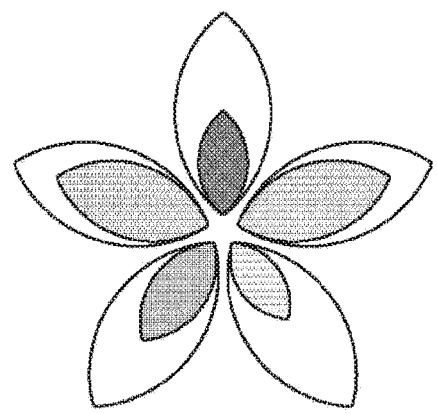
FIGS. 25A and 25B are diagrams that illustrate modified examples of the petal chart.
Figure 25B:
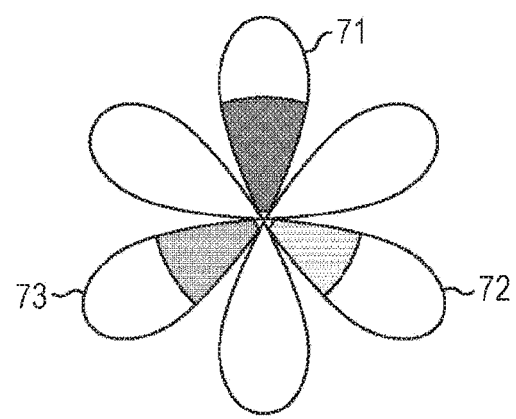

As the shapes of petal areas configuring the petal chart, the shapes of other petals as illustrated in FIGS. 24A, 24B and 24C and FIGS. 25A and 25B may be used. In addition, as illustrated in FIGS. 25A and 25B, the number of petal areas configuring one petal chart may be appropriately changed.

For example, a petal chart illustrated in FIG. 25B is configured by six petal areas, and score images are displayed in petal areas 71 to 73 that are three areas among them. In the petal areas 71 to 73, score images of mutually-different colors are displayed.

Figure 26A:
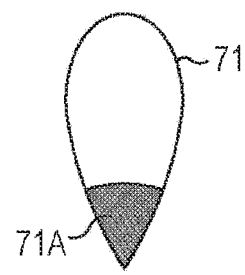
FIGS. 26A, 26B and 26C are diagrams that illustrate examples of display of the petal chart illustrated in FIG. 25B.
Figure 26B:
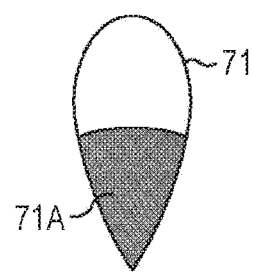
Figure 26C:
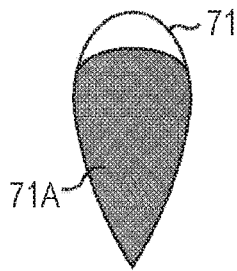

FIGS. 26A, 26B and 26C are diagrams that illustrate examples of display of the score images illustrated in FIG. 25B.

Similarly to the example illustrated in FIGS. 7A, 7B and 7C, the item of the pore is assumed to be assigned to the petal area 71. A size that is the same as the size of the petal area 71 is set as a maximal score such as five points, and, for example, in a case where the score of the pore state is one point, as illustrated in FIG. 26A, a score image 71A is displayed to fill up a 1/5 range of the petal area 71 on the lower side.

In a case where the score of the pore state is 2.5 points, as illustrated in FIG. 26B, the score image 71A is displayed to fill up a 2.5/5 range of the petal area 71 on the lower side. In a case where the score of the pore state is 4 points, as illustrated in FIG. 26C, the score image 71A is displayed to fill up a 4/5 range of the petal area 71 on the lower side.

In other words, in this example, instead of displaying an image having an approximately same shape as the shape of the petal area 71 as the score image 71A, in a sense, the score image 71A is displayed in a form in which liquid is filled inside a sealed cylinder.

Figure 27:
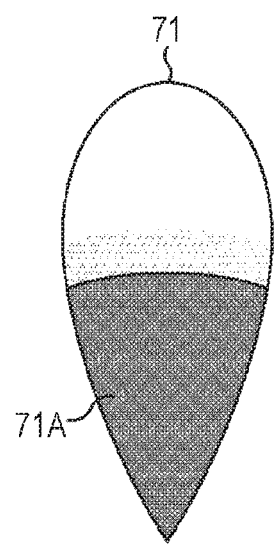
FIG. 27 is a diagram that illustrates an example of display of the petal chart illustrated in FIG. 25B.
Figure 28A:
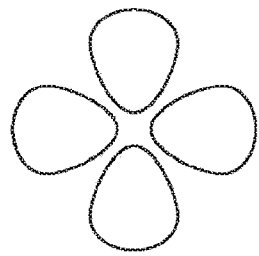
FIGS. 28A, 28B, 28C, 28D, 28E, 28F and 28G are diagrams that illustrate other modified examples of the petal chart.
Figure 28E:
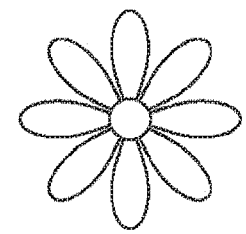
Figure 28B:
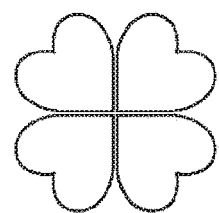
Figure 28F:
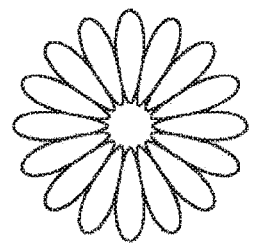
Figure 28C:
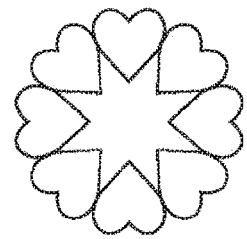
Figure 28G:
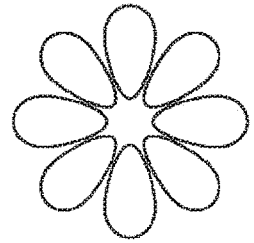
Figure 28D:
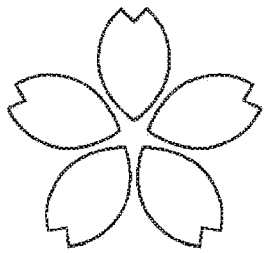

In this way, a score image having a shape different from the shape of the petal area may be configured to be displayed. A reference score, as illustrated in FIG. 27, may be displayed not in a dotted line but in a color acquired by adding transparency to the color of the score image 71A. In FIG. 27, a portion represented in a light color is a portion displayed in a color to which transparency is added, and an upper limit thereof represents a reference score. As described above, a score that is used as the reference includes a score of the previous measurement, a target score set in advance by the user, an average score by age, and the like.

FIGS. 28A, 28B, 28C, 28D, 28E, 28F and 28G are diagrams that illustrate other modified examples of the petal chart.

The measurement results of the skin state may be displayed using petal charts as illustrated in FIGS. 28A, 28B, 28C, 28D, 28E, 28F and 28G. The kind of petal chart may be appropriately changed like a case where the kind of flower, the shape of petal areas, the number of petal areas, or a method for overlapping petal areas is changed.

Conditions for changing the kind of petal chart are as below. Seasons such as spring, summer, fall, and winter and a period User's age and user's attribute such as a community group Result of classification of user's external view such as the skin or a face type Classification result of the user's inside such as a feeling mood or a taste FIG. 29 is a diagram that illustrates a further another modified example of the petal chart.

Figure 29:
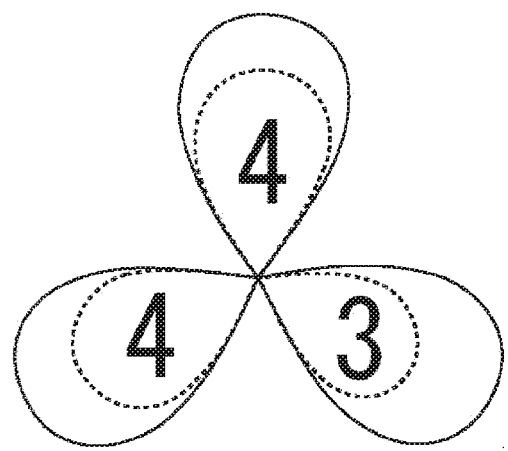
FIG. 29 is a diagram that illustrates a further another modified example of the petal chart.

As illustrated in FIG. 29, numbers respectively representing the scores of items assigned to petal areas may be displayed in the petal areas without displaying any score image.

Figure 30A:
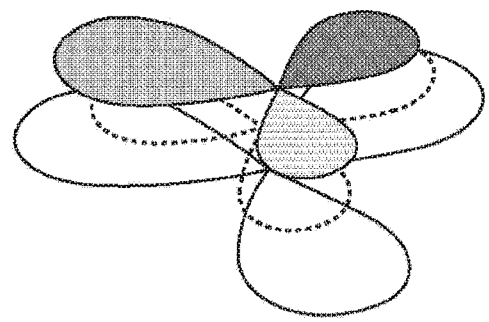
FIGS. 30A and 30B are diagrams that illustrate examples of display of the petal chart.
Figure 30B:
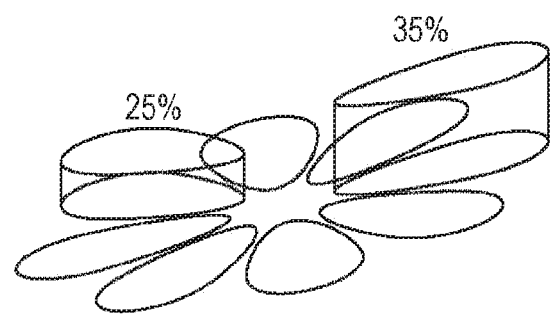

FIGS. 30A and 30B are diagrams that illustrate examples of display of the petal chart.

As illustrated in FIG. 30A, a petal chart that is in a squint-eyed state may be displayed in which petal areas configuring the petal chart, dotted lines representing scores that are used as references, and score images are configured as information of mutually-different layers. A score that is used as the reference includes a score of the previous measurement, a target score set in advance by the user, an average score by age, and the like.

As illustrated in FIG. 30B, an image having the same shape as the petal area may be displayed on the petal area of an item of which the score has been increased. In such a case, the image having the same shape as the petal area is displayed at a position corresponding to the increase rate.

Figure 31:
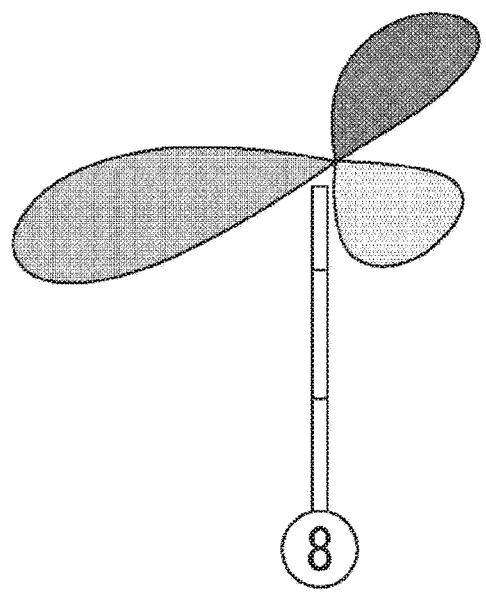
FIG. 31 is a diagram that illustrates another example of display of the petal chart.

FIG. 31 is a diagram that illustrates another example of display of the petal chart.

In a state in which a petal chart that is in the front-viewing state is displayed, as illustrated in FIG. 31, the viewpoint of the petal chart may be configured to be switchable. The petal chart illustrated in FIG. 31, for example, is acquired by switching the viewpoint of one petal chart illustrated in FIG. 21. The switching between viewpoints of the petal chart, for example, is performed through a touch operation for a touch panel disposed on the surface of the display 51.

Figure 32:
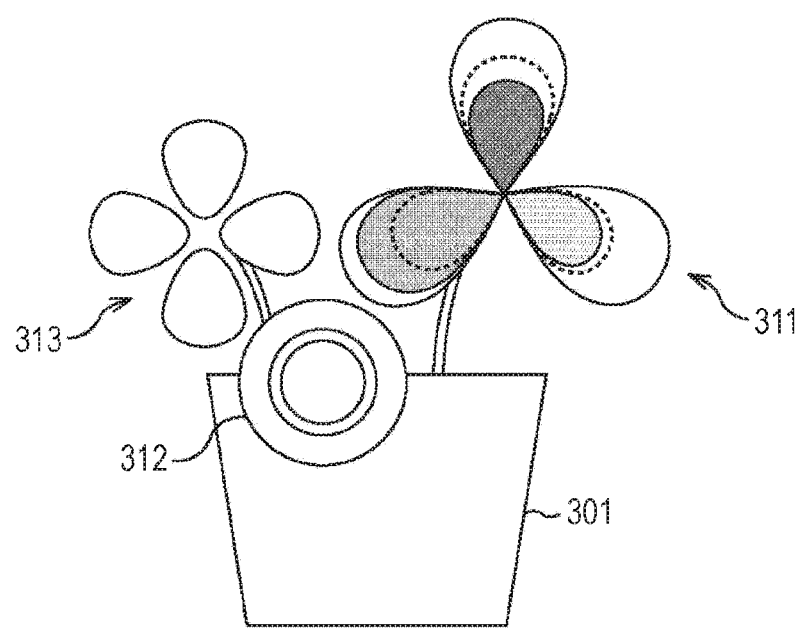
FIG. 32 is a diagram that illustrates another example of display of the petal chart.

FIG. 32 is a diagram that illustrates another example of display of the petal chart.

The information of items influencing the skin state such as life habits and a feeling mood may be displayed using images of flowers instead of displaying the information using the stem images or the root images.

An image illustrated in FIG. 32 is an image that represents a state in which three flowers grow in a pot represented by an image 301. The image illustrated in FIG. 32 is displayed on the measurement result display screen.

A petal chart 311 illustrated in FIG. 32 represents a measurement result of the skin state of the user. A flower image 312 imitating a circular flower, for example, represents the state of a feeling mood of the user. The flower image 312 is displayed in a color and a size corresponding to the feeling mood of the user.

A petal chart 313 configured by four petal areas, for example, represents scores of items of the life habit of the user. In each of the petal areas configuring the petal chart 313, score images representing the scores of the life habit and the feeling mood are displayed.

Also based on the image illustrated in FIG. 32, the user can freely check the casual relation between the skin state and the life habit and the feeling mood in a form having no psychological load. The scores of the items of the skin state may be displayed by using images of mutually-different flowers like a case where a flower representing a pore state, a flower representing a texture state, and a flower representing a spot state are displayed.

Figure 33A:
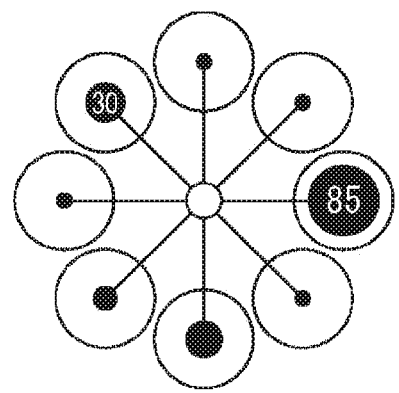
FIGS. 33A and 33B are diagrams that illustrate examples of display of a measurement result.
Figure 33B:
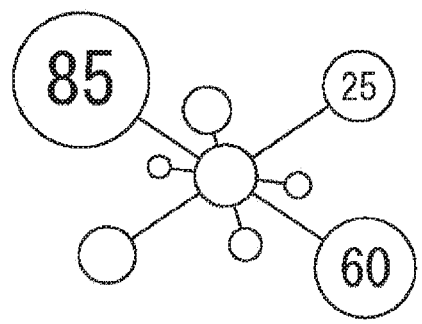

In the description presented above, while a measurement result of the skin state is represented by an image imitating a flower, as illustrated in FIGS. 33A and 33B, the measurement result may be represented by using images other than an image imitating a flower.

The images illustrated in FIGS. 33A and 33B are similar to the petal chart described above in that circular areas to which the items of the skin state are respectively assigned are formed in directions with a predetermined position set as the center. A center circle and circular areas disposed on the periphery thereof are respectively connected to each other using straight lines. In the circular areas to which the items of the skin state are assigned, colored circular images of sizes corresponding to the scores of the items assigned to the areas are displayed. In each circular area, a number appropriately representing a corresponding score is also displayed.

The processes of the information processing terminal 1 and the analysis server 3 realizing the display as described above will be described later with reference to a flowchart.

<3. Configuration of Each Apparatus>

3-1. Configuration of Skin Measuring Instrument 2

Figure 34:
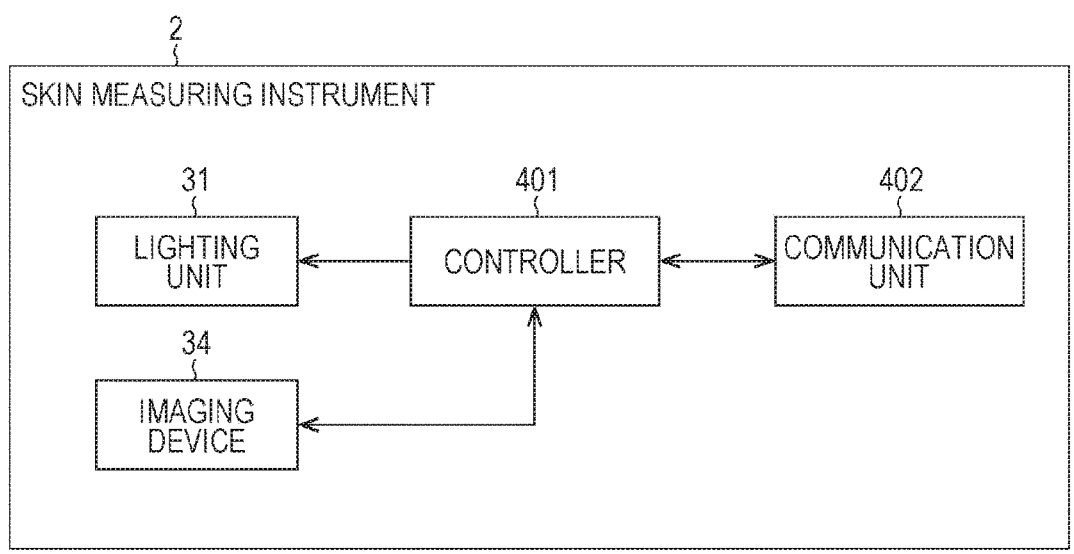
FIG. 34 is a block diagram that illustrates an example of the configuration of a skin measuring instrument.

FIG. 34 is a block diagram that illustrates an example of the configuration of the skin measuring instrument 2. A same reference sign is assigned to each configuration that is the same as that illustrated in FIG. 3. Duplicate description will not be presented as is appropriate.

The skin measuring instrument 2 is configured by: a lighting unit 31; an imaging device 34; a controller 401; and a communication unit 402.

The lighting unit 31 emits visible light to the skin when a skin image is captured. In addition, the lighting unit 31 emits light of a predetermined wavelength that is used for measuring melanin or the like.

The imaging device 34 is an imaging device such as a Complementary Metal Oxide Semiconductor (CMOS) image sensor. The imaging device 34 detects reflected light of the light emitted by the lighting unit 31 and performs a photoelectric conversion and the like. The imaging device 34 outputs data of a skin image acquired by performing the photoelectric conversion or the like to the controller 401.

The controller 401 communicates with the information processing terminal 1 through the communication unit 402 and controls each unit of the skin measuring instrument 2, for example, under the control of the information processing terminal 1. The controller 401 transmits the data of the skin image supplied from the imaging device 34 from the communication unit 402 to the information processing terminal 1.

The communication unit 402 is a communication module of a predetermined standard such as wireless LAN. The communication unit 402 communicates with the information processing terminal 1. The communication unit 402 outputs information transmitted from the information processing terminal 1 to the controller 401 and transmits information supplied from the controller 401 to the information processing terminal 1.

3-2. Configuration of Information Processing Terminal

Figure 35:
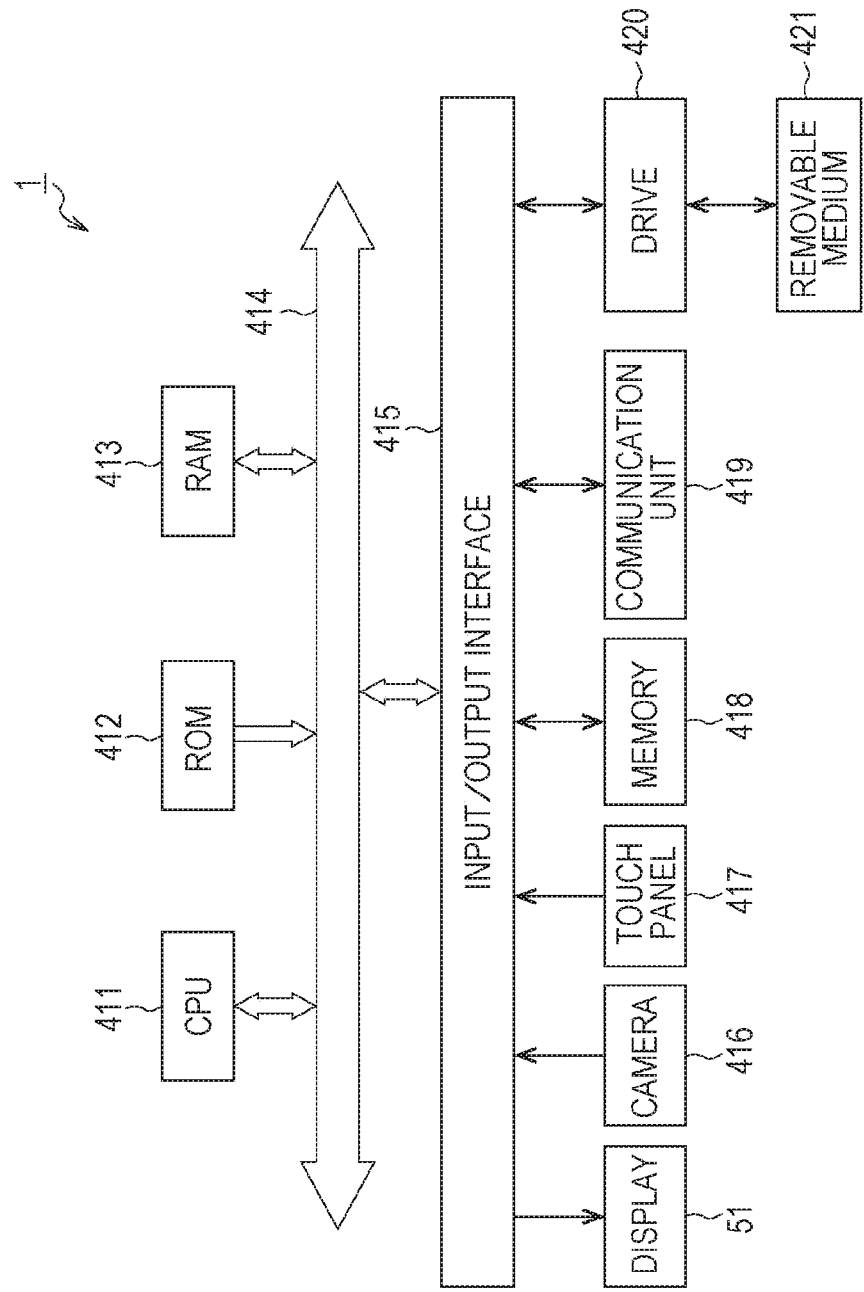
FIG. 35 is a block diagram that illustrates an example of the hardware configuration of an information processing terminal.

FIG. 35 is a block diagram that illustrates an example of the hardware configuration of the information processing terminal 1.

A Central Processing Unit (CPU) 411, a Read Only Memory (ROM) 412, and a Random Access Memory (RAM) 413 are interconnected through a bus 414.

In addition, an input/output interface 415 is connected to the bus 414. A display 51, a camera 416, a touch panel 417, a memory 418, a communication unit 419, and a drive 420 are connected to the input/output interface 415.

The touch panel 417 is disposed to overlap the display 51. The touch panel 417 detects a user's operation and outputs information representing the content of the operation to the CPU 411.

The memory 418 is configured by a flash memory or the like. The memory 418 records various kinds of information such as information representing measurement results of the skin state that has been transmitted from the analysis server 3. The information recorded in the memory 418 is appropriately read by the CPU 411.

The communication unit 419 is a communication module of a predetermined standard such as wireless LAN. The communication unit 419 communicates with the skin measuring instrument 2. The communication unit 419 is connected to a relay apparatus 4A and communicates with the analysis server 3 connected through the network 4 and the like.

The drive 420 reads data recorded in a removable medium 421 and records data into the removable medium 421. The removable medium 421 is a recording medium such as a memory card installed to a slot disposed in the information processing terminal 1 or a USB memory installed to a terminal of the information processing terminal 1.

Figure 36:
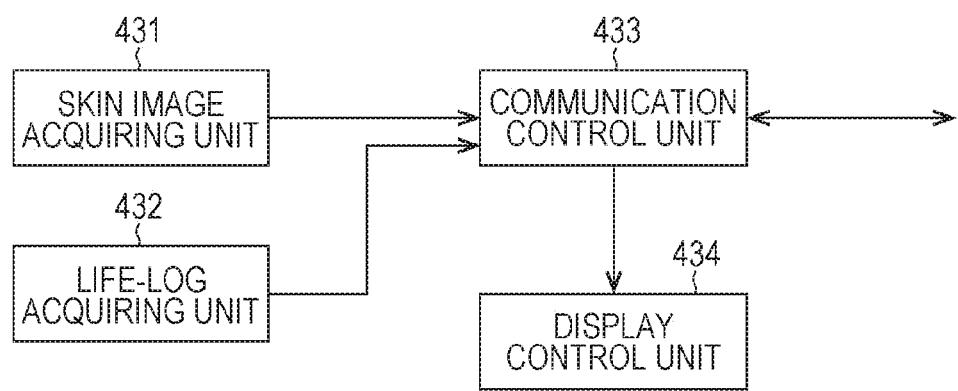
FIG. 36 is a block diagram that illustrates an example of the functional configuration of an information processing terminal.

FIG. 36 is a block diagram that illustrates an example of the functional configuration of the information processing terminal 1.

At least some of the functional units illustrated in FIG. 36 are realized by executing a predetermined program using the CPU 411 illustrated in FIG. 35.

As illustrated in FIG. 36, in the information processing terminal 1, a skin image acquiring unit 431, a life-log acquiring unit 432, a communication control unit 433, and a display control unit 434 are realized.

The skin image acquiring unit 431 acquires skin images captured by the skin measuring instrument 2 and received by the communication unit 219. For example, a plurality of skin images captured by changing the wavelength are acquired for each one measurement position. The skin image acquiring unit 431 outputs the acquired skin images to the communication control unit 433.

The life-log acquiring unit 432 acquires a life-log that is information of a life habit, a feeling mood, and the like of a user. The life-log acquiring unit 432 acquires a life-log input by the user using the input screen illustrated in FIG. 23 or acquires a life-log by communicating with a wearable terminal worn by the user by controlling the communication unit 419. The life-log acquiring unit 432 outputs the acquired life log to the communication control unit 433.

The communication control unit 433 transmits the skin images supplied from the skin image acquiring unit 431 and the life-log supplied from the life-log acquiring unit 432 to the analysis server 3 by controlling the communication unit 219. In addition, the communication control unit 433 receives information representing measurement results transmitted from the analysis server 3. The communication control unit 433 functions as an acquisition unit that receives and acquires information representing measurement results of the skin state. The communication control unit 433 outputs the information representing the measurement results to the display control unit 434.

The display control unit 434 displays a measurement result display screen on the display 51 based on the information supplied from the communication control unit 433 and presents the measurement results of the skin state to the user. The display control unit 434 functions as a presentation unit that presents measurement results of the skin state to the user. In addition, the display control unit 434 appropriately performs switching of the display of the measurement result display screen in accordance with a user's operation.

3-3. Configuration of Analysis Server 3

Figure 37:
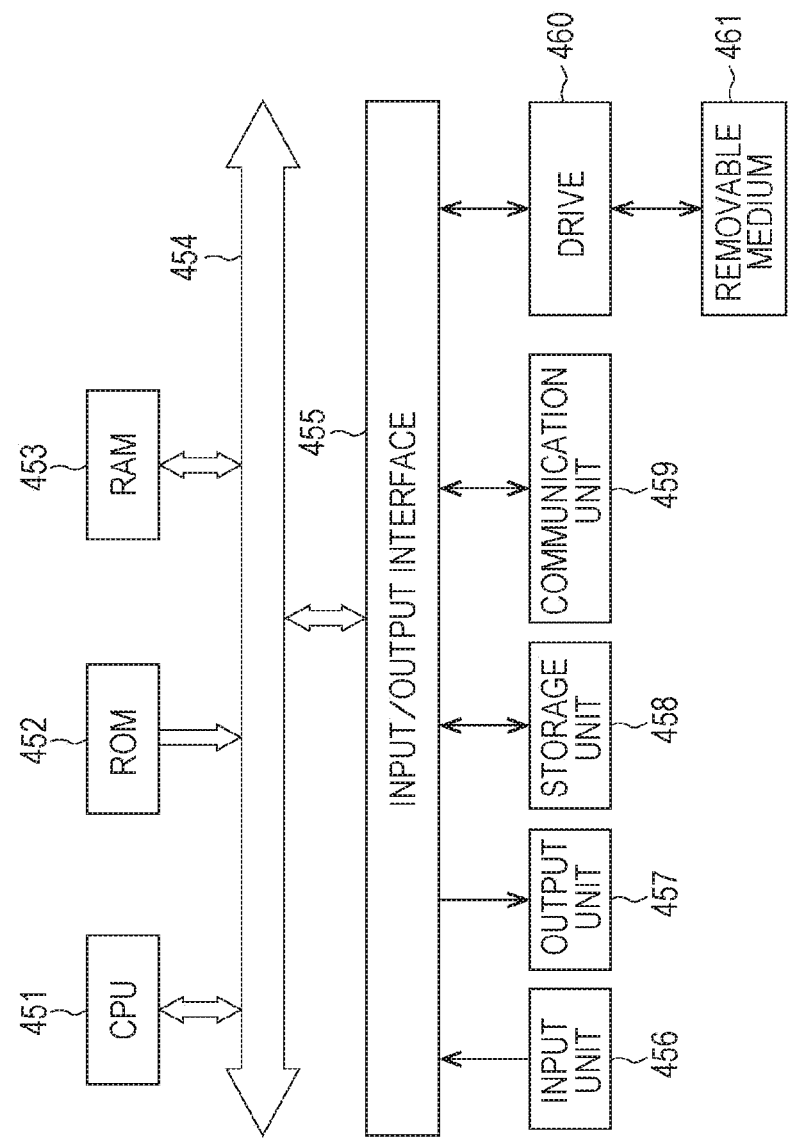
FIG. 37 is a block diagram that illustrates an example of the hardware configuration of an analysis server.

FIG. 37 is a block diagram that illustrates an example of the hardware configuration of the analysis server 3.

The CPU 451, a ROM 452, and a RAM 453 are interconnected through a bus 454. In addition, an input/output interface 455 is connected to the bus 454.

An input unit 456 such as a keyboard or a mouse and an output unit 457 such as a display are connected to the input/output interface 455. A storage unit 458 such as a hard disk and a communication unit 459 that communicates with various apparatuses such as the information processing terminal 1 through the network 4 are connected to the input/output interface 455.

In addition, a drive 460 is connected to the input/output interface 455. The drive 460 reads data recorded in a removable medium 461 and records data into the removable medium 461.

Figure 38:
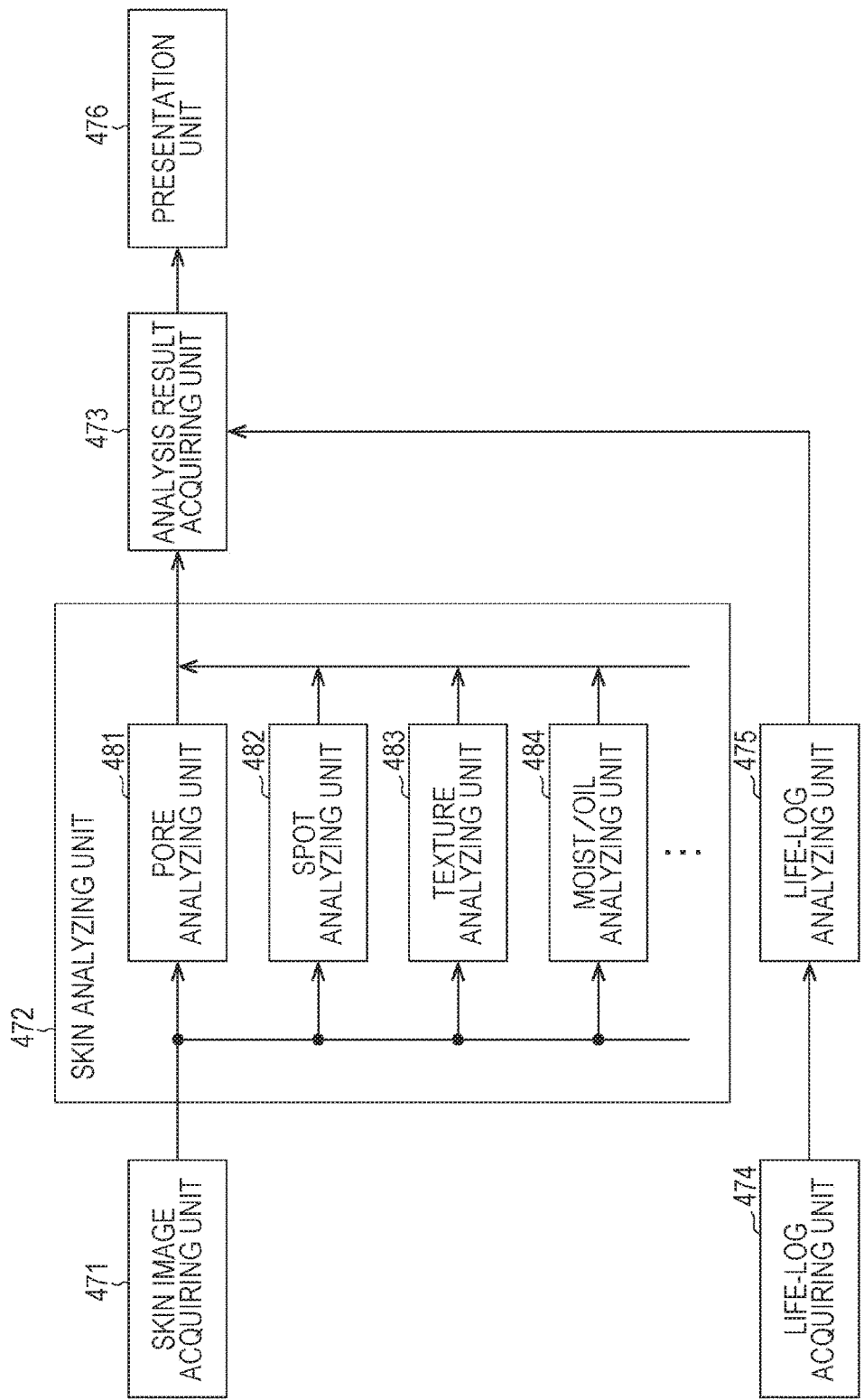
FIG. 38 is a block diagram that illustrates an example of the functional configuration of an analysis server.

FIG. 38 is a block diagram that illustrates an example of the functional configuration of the analysis server 3.

At least some of functional units illustrated in FIG. 38 are realized by executing a predetermined program by using the CPU 451 illustrated in FIG. 37.

As illustrated in FIG. 38, in the analysis server 3, a skin image acquiring unit 471, a skin analyzing unit 472, an analysis result acquiring unit 473, a life-log acquiring unit 474, a life-log analyzing unit 475, and a presentation unit 476 are realized. In the skin analyzing unit 472, a pore analyzing unit 481, a spot analyzing unit 482, a texture analyzing unit 483, and a moist/oil analyzing unit 484 are included.

The skin image acquiring unit 471 acquires skin images transmitted from the information processing terminal 1 by controlling the communication unit 459. The skin image acquiring unit 471 outputs the acquired skin images to each unit of the skin analyzing unit 472.

The pore analyzing unit 481 of the skin analyzing unit 472 performs image processing of the skin images supplied from the skin image acquiring unit 471 and analyzes the pore state. The pore analyzing unit 481, for example, outputs information representing the opening state of the pore and information representing the darkening state of the pore as information representing a result of the analysis of the pore.

The spot analyzing unit 482 performs image processing of skin images supplied from the skin image acquiring unit 471 and analyzes the spot state. The spot analyzing unit 482, for example, outputs information representing a red spot state and information representing a melanin spot state as information representing a result of the analysis of the spot.

The analysis of the pore state that is executed by the pore analyzing unit 481 and the analysis of the spot state that is executed by the spot analyzing unit 482 will be described later in detail.

The texture analyzing unit 483 performs image processing of skin images supplied from the skin image acquiring unit 471 and analyzes the texture state. For example, by analyzing the skin images, the texture analyzing unit 483 detects cristae cutis that makes texture and specifies the area, the shape, and the direction of the cristae cutis. The texture analyzing unit 483, for example, specifies the fineness of the skin by comparing the area of the cristae cutis with a threshold. In addition, the texture analyzing unit 483 determines whether or not the cristae cutis is aligned with regularity based on the shape and the direction of the cristae cutis and specifies the alignment state of the skin. The texture analyzing unit 483 outputs information of the fineness of the skin and the information of the alignment state.

A method of evaluating the skin state, for example, is disclosed in JP 2012-239768A.

The moist/oil analyzing unit 484 performs image processing of skin images supplied from the skin image acquiring unit 471 and analyzes the moist amount and the oil amount of the skin. For the analysis of the moist amount and the oil amount, skin images captured by emitting light of wavelengths used for detecting the moist amount and the oil amount to the skin are used. In a case where a sensor used for measuring the moist amount and the oil amount is disposed in the skin measuring instrument 2, the moist amount and the oil amount measured by the sensor may be acquired by the moist/oil analyzing unit 484. The moist/oil analyzing unit 484 outputs information of the moist amount and the oil amount.

The analysis result acquiring unit 473 acquires information representing analysis results output from each unit of the skin analyzing unit 472 and acquires a score representing the skin state. In the analysis result acquiring unit 473, information associating an analysis result supplied from the skin analyzing unit 472 and a score with each other is prepared.

For example, the analysis result acquiring unit 473 evaluates the opening state of the pore and the darkening state of the pore based on the information supplied from the pore analyzing unit 481 and acquires a score representing the pore state. In addition, the analysis result acquiring unit 473 evaluates a red spot state and a melanin spot state based on the information supplied from the spot analyzing unit 482 and acquires a score representing the spot state. The analysis result acquiring unit 473 evaluates the fineness and the alignment state of the skin based on the information supplied from the texture analyzing unit 483 and acquires a score representing the skin state.

In addition, the analysis result acquiring unit 473 acquires the information of the moist amount and the oil amount supplied from the moist/oil analyzing unit 484 and classifies the skin into one skin type among normal skin, oily skin, dry skin and mixed skin. For example, in a case where the moist amount is 30 or more, and the oil amount is less than 70, the analysis result acquiring unit 473 classifies the skin type into the "normal skin".

The analysis result acquiring unit 473 outputs information representing the scores of the pore, the spot, and the texture, the skin type, and the moist amount and the oil amount to the presentation unit 476 as information representing measurement results of the skin state. In addition, the analysis result acquiring unit 473 outputs the scores of the life habit and the feeling mood supplied from the life-log analyzing unit 475 to the presentation unit 476.

The life-log acquiring unit 474 acquires the life-log transmitted from the information processing terminal 1 by controlling the communication unit 459. The life-log acquiring unit 474 outputs the acquired life-log to the life-log analyzing unit 475.

The life-log analyzing unit 475 analyzes the life-log supplied from the life-log acquiring unit 474 and acquires the scores of the life habit and the feeling mood of the user before the measurement of the skin state of this time.

For example, in a case where, before the measurement of this time, the input of a life-log using the input screen illustrated in FIG. 23 is performed a plurality of times, the life-log analyzing unit 475 acquires an average value of input values of each of the items of the "meals", the "sleep", and the "exercise" as the scores of the meals, the sleep, and the exercise that are items of the life habit. In addition, the life-log analyzing unit 475 acquires an average value of input values of the item of the "feeling mood" as the score of the feeling mood. The score of the feeling mood may be acquired by using a combination of the input values of the items of the "fatigue" and "having a period". The life-log analyzing unit 475 outputs the scores of the life habit and the feeling mood to the analysis result acquiring unit 473.

The presentation unit 476 transmits the information supplied from the analysis result acquiring unit 473 to the information processing terminal 1 by controlling the communication unit 459 and presents the measurement results of the skin state to the user. It may be configured such that a measurement result display screen is generated by the analysis server 3, and information of the generated measurement result display screen is transmitted from the analysis server 3 to the information processing terminal 1.

Figure 39:
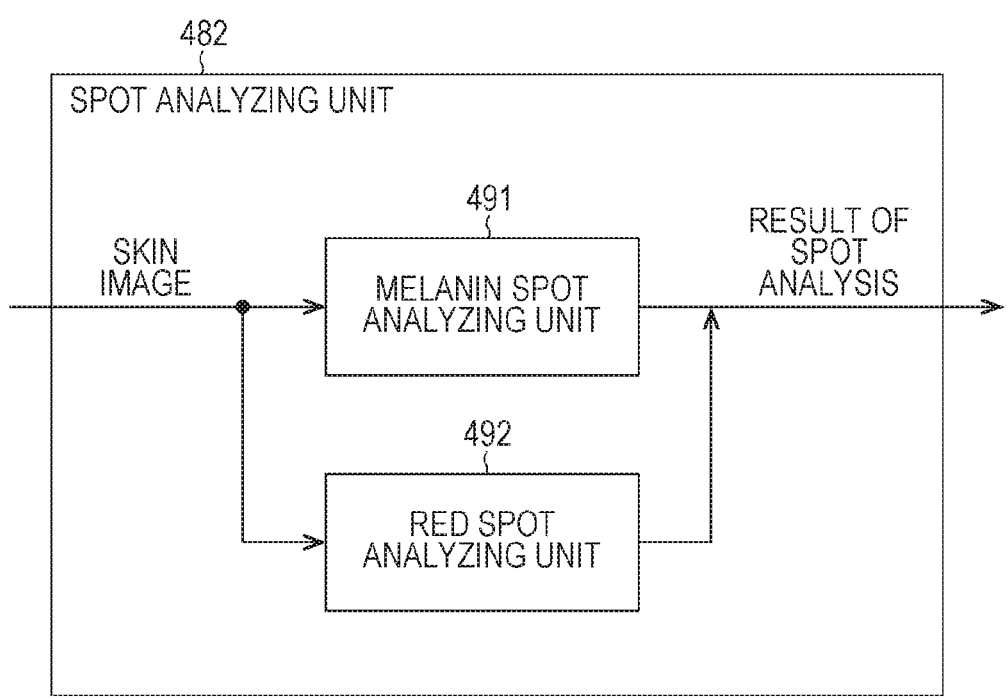
FIG. 39 is a block diagram that illustrates an example of the configuration of a spot analyzing unit.

Spot Analyzing Unit 482 FIG. 39 is a block diagram that illustrates an example of the configuration of the spot analyzing unit 482.

The spot analyzing unit 482 is configured by a melanin spot analyzing unit 491 and a red spot analyzing unit 492. The skin image output from the skin image acquiring unit 471 is input to the melanin spot analyzing unit 491 and the red spot analyzing unit 492.

The melanin spot analyzing unit 491 performs image processing of the skin image and analyzes the melanin spot state. The melanin spot analyzing unit 491 outputs information representing a result of the analysis.

The red spot analyzing unit 492 performs image processing of the skin image and analyzes the red spot state. The red spot analyzing unit 492 outputs information representing a result of the analysis.

Figure 40:
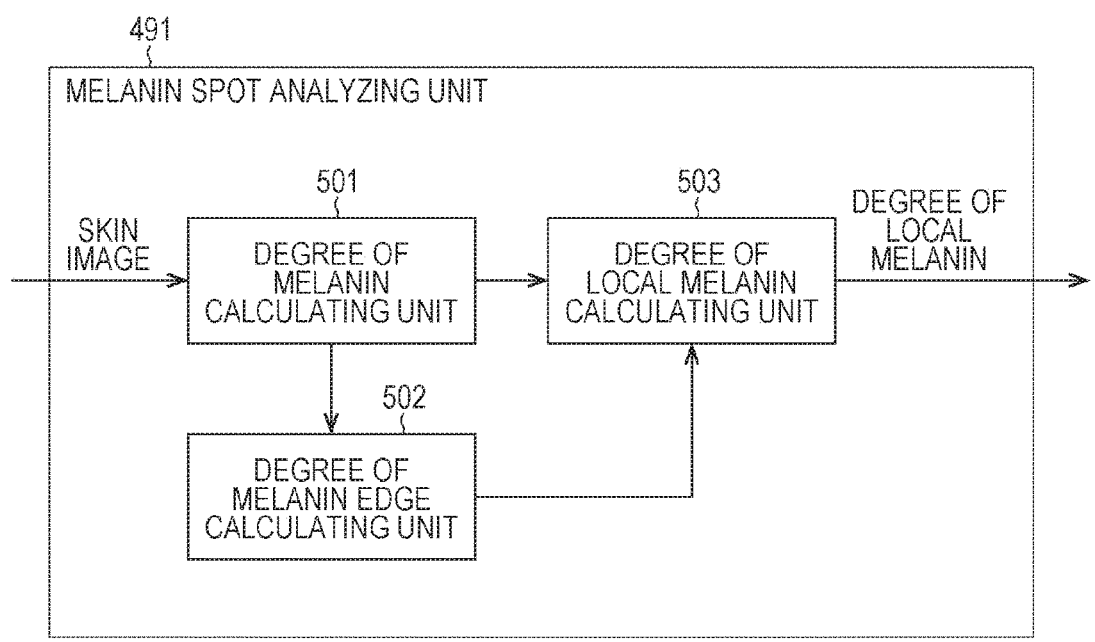
FIG. 40 is a block diagram that illustrates an example of the configuration of a melanin spot analyzing unit.

FIG. 40 is a block diagram that illustrates an example of the configuration of the melanin spot analyzing unit 491 illustrated in FIG. 39.

The melanin spot analyzing unit 491 is configured by: a melanin degree calculating unit 501; a melanin edge degree calculating unit 502; and a local melanin degree calculating unit 503. The melanin spot analyzing unit 491 has a function for detecting a melanin component of the skin.

Figure 41:
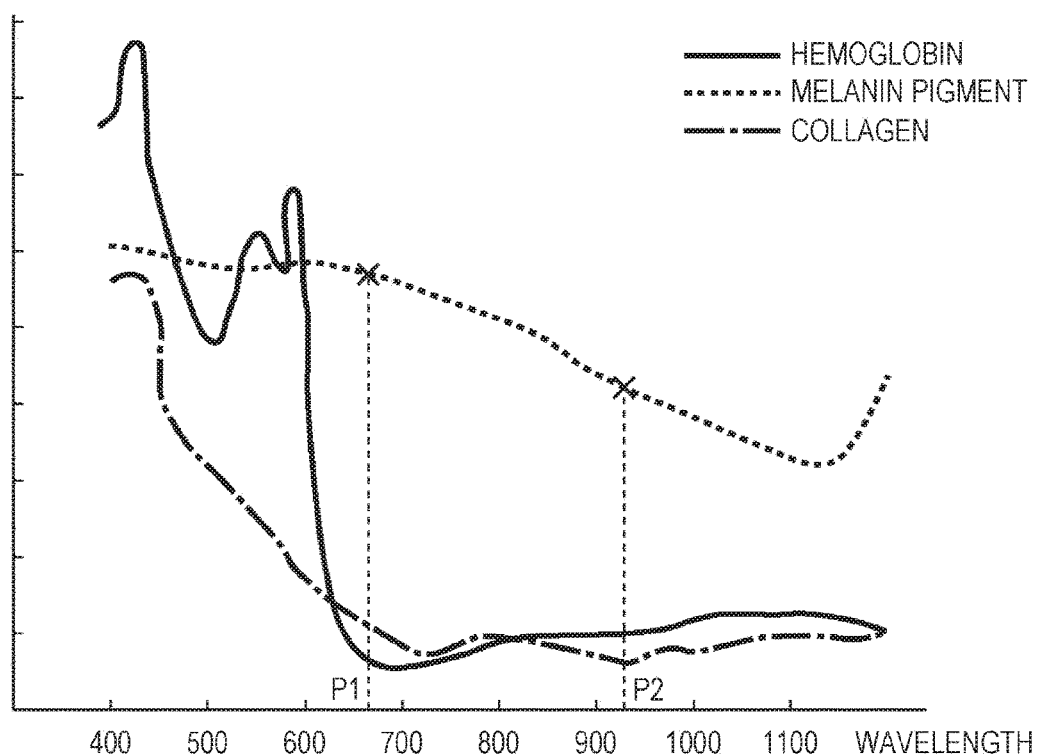
FIG. 41 is a diagram that illustrates light absorption characteristics of melanin.

The melanin degree calculating unit 501 analyzes the skin image and acquires a melanin amount (a distribution of the melanin component) at each position. As illustrated in FIG. 41, melanin exhibits a light absorption characteristic of descending toward the right side between a wavelength zone of red denoted by a position P1 and a wavelength zone of near infrared light denoted by a position P2.

The melanin degree calculating unit 501 acquires a melanin amount MX(x, y) based on a skin image captured under a red light source and a skin image captured under a near infrared light source by using the light absorption characteristic of melanin. The melanin amount MX(x, y) is represented using the following Equation (1).

[Mathematical Formula 1]

$$MX(x,y) = A_{MX}(\log(I_{IR}(x,y)) - \log(I_R(x,y))) + B_{MX} \ldots \quad (1)$$

In Equation (1), $I_{IR}(x, y)$ represents the brightness (for example, an R pixel value) of the skin image captured under the near infrared light source at a position (x, y). In addition, $I_R(x, y)$ represents the brightness (for example, an R pixel value) of the skin image captured under the red light source at a position (x, y).

Figure 42:
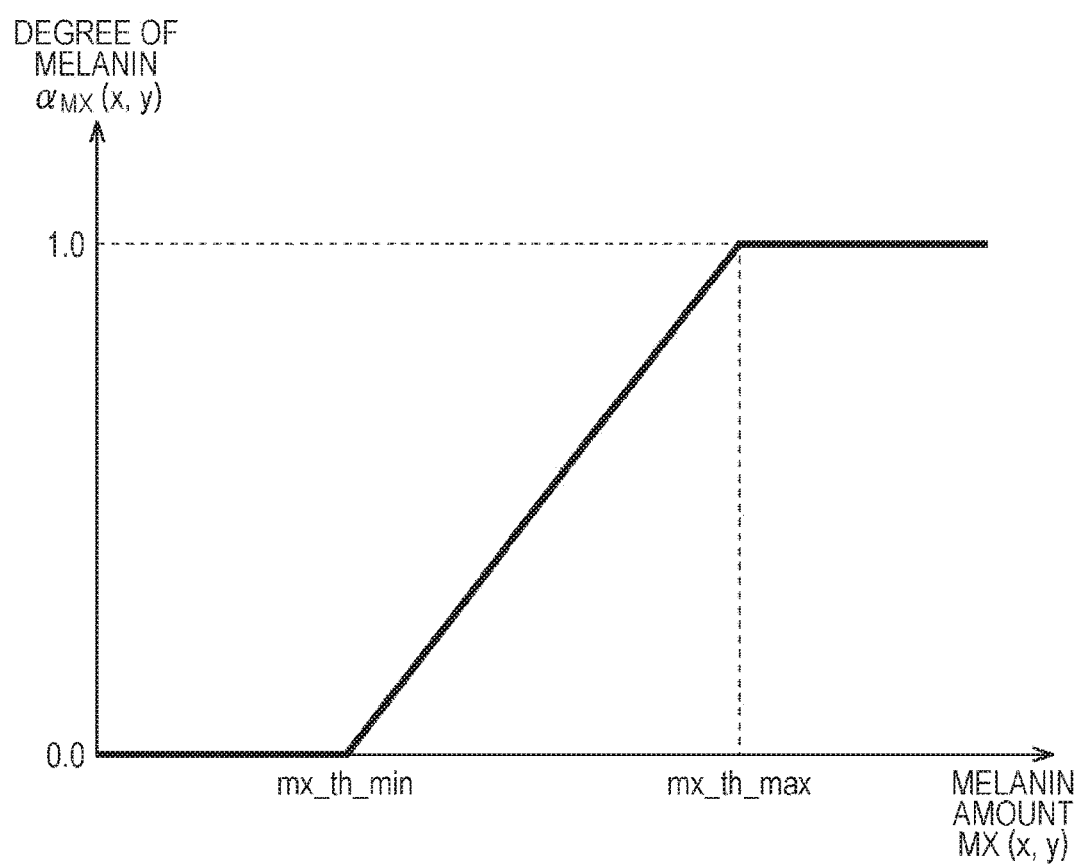
FIG. 42 is a diagram that illustrates an example of a normalized function.

In addition, $A_{MX}$ and $B_{MX}$ are parameters used for calculating a melanin amount. The melanin degree calculating unit 501 adjusts the contrast of the melanin distribution by normalizing the melanin amount MX(x, y) of each position into a value in the range of [0, 1] based on a normalization function illustrated in FIG. 42. The melanin degree calculating unit 501 outputs information representing the melanin amount MX(x, y) to the melanin edge degree calculating unit 502 and outputs a value representing a melanin amount of each position after the normalization to the local melanin degree calculating unit 503 as a melanin degree $\alpha_{MX}(x, y)$.

The melanin edge degree calculating unit 502 calculates a melanin edge degree based on the melanin amount MX(x, y) of each position acquired by the melanin degree calculating unit 501. The melanin edge degree is a value that represents the degree of locality of melanin.

The melanin edge degree calculating unit 502 generates an edge image that is an image representing a difference between the melanin amount of each position and a melanin amount of the periphery thereof. As a method for generating an edge image, for example, there is a method using a line extracting filter. The line extracting filter is a filter that is used for detecting the contour. Here, the value of the edge image at each position will be represented as mx_edge(x, y).

Figure 43:
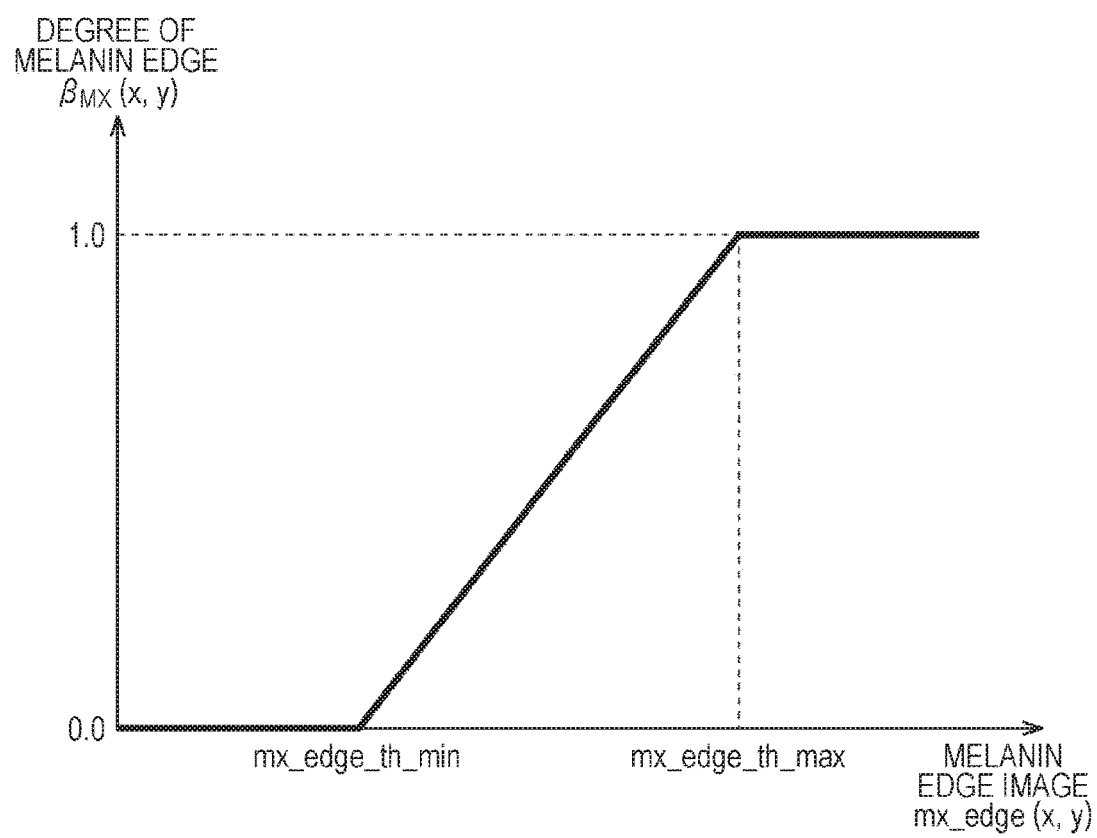
FIG. 43 is a diagram that illustrates an example of another normalized function.

The value of mx_edge(x, y) is high at a portion at which the melanin amount is locally higher than that of the periphery or a portion at which the melanin amount is locally lower than that of the periphery. The melanin edge degree calculating unit 502 normalizes mx_edge(x, y) into a value in the range of [0, 1] based on the normalization function represented in FIG. 43 and outputs a value after the normalization to the local melanin degree calculating unit 503 as a melanin edge degree $\beta_{MX}(x, y)$.

The local melanin degree calculating unit 503 calculates a local melanin degree $\gamma_{MX}(x, y)$ by performing multiplication of the melanin degree $\alpha_{MX}(x, y)$ acquired by the melanin degree calculating unit 501 and the melanin edge degree $\beta_{MX}(x, y)$ acquired by the melanin edge degree calculating unit 502. The local melanin degree $\gamma_{MX}(x, y)$ at a position at which the melanin degree is higher than that of the periphery has a high value. The local melanin degree calculating unit 503 outputs information representing the local melanin degree $\gamma_{MX}(x, y)$ as a result of the analysis of a melanin spot.

In addition, in a case where an area in which the melanin degree is high is relatively wide, only the local melanin degree of the periphery of the area has a high value, and the local melanin degree of the center portion has a low value.

In order to prevent this, the local melanin degree calculating unit 503, for example, performs a binarization process and performs a process of filling up a detected closed area with a value of the periphery portion.

Figure 44:
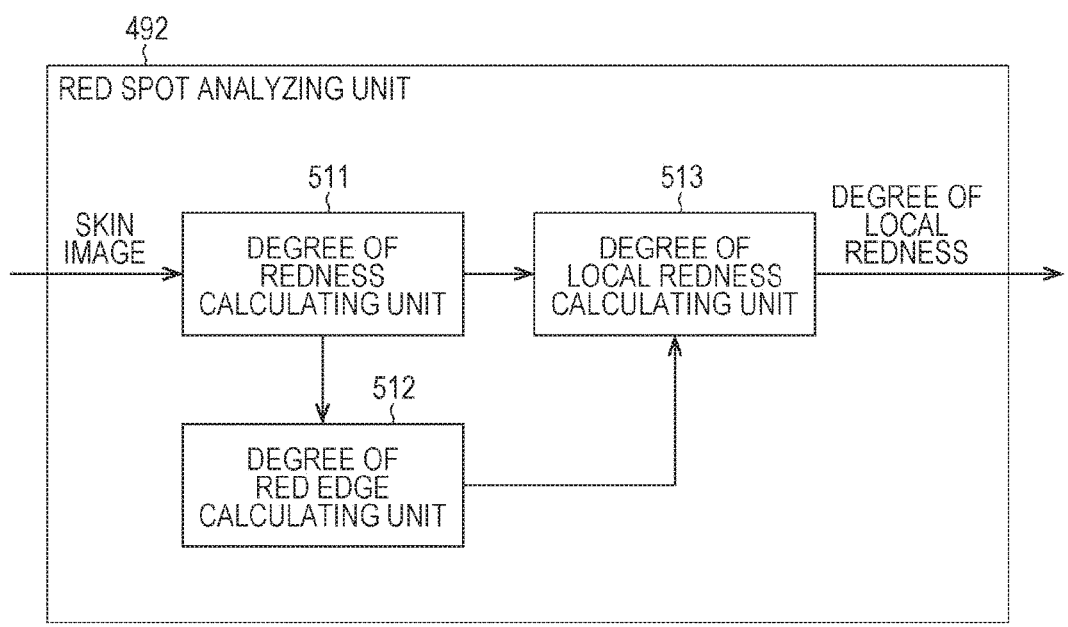
FIG. 44 is a block diagram that illustrates an example of the configuration of a red spot analyzing unit.

FIG. 44 is a block diagram that illustrates an example of the configuration of the red spot analyzing unit 492 illustrated in FIG. 39.

The red spot analyzing unit 492 is configured by: a red degree calculating unit 511; a red edge degree calculating unit 512; and a local red degree calculating unit 513. The red spot analyzing unit 492 has a function for detecting a hemoglobin component (red component) of the skin.

Figure 45:
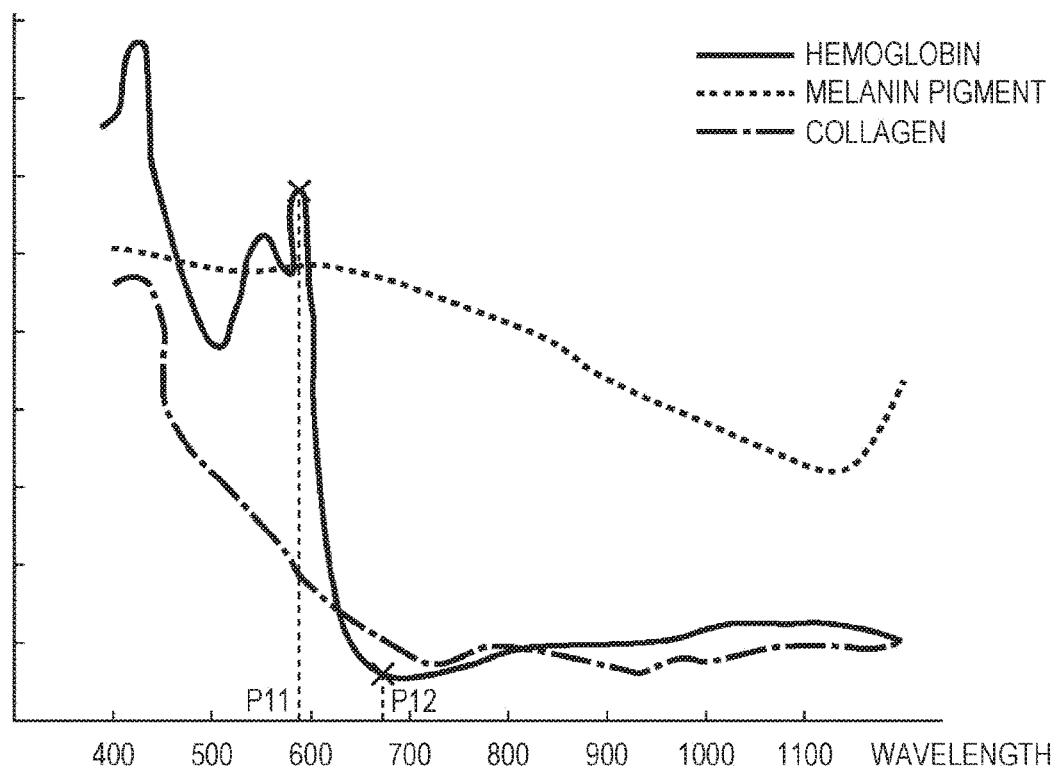
FIG. 45 is a diagram that illustrates light absorption characteristics of hemoglobin.

The red degree calculating unit 511 analyzes the skin image and acquires a hemoglobin amount (a distribution of the hemoglobin component) at each position. As illustrated in FIG. 45, hemoglobin exhibits a light absorption characteristic of descending toward the right side between a wavelength zone of green denoted by a position P11 and a wavelength zone of red denoted by a position P12.

The red degree calculating unit 511 acquires a red amount EX(x, y) based on a skin image captured under a green light source and a skin image captured under a red light source by using the light absorption characteristic of hemoglobin. The red amount EX(x, y) is represented using the following Equation (2).

[Mathematical Formula 2]

$$EX(x,y)=A_{EX}\cdot(\log(I_R(x,y))-\log(I_G(x,Y)))+B_{EX}\ldots \quad (2)$$

In Equation (2), $I_R(x, y)$ represents the brightness (for example, an R pixel value) of the skin image captured under the red light source at a position (x, y). In addition, $I_G(x, y)$ represents the brightness (for example, a G pixel value) of the skin image captured under the green light source at a position (x, y).

Figure 46:
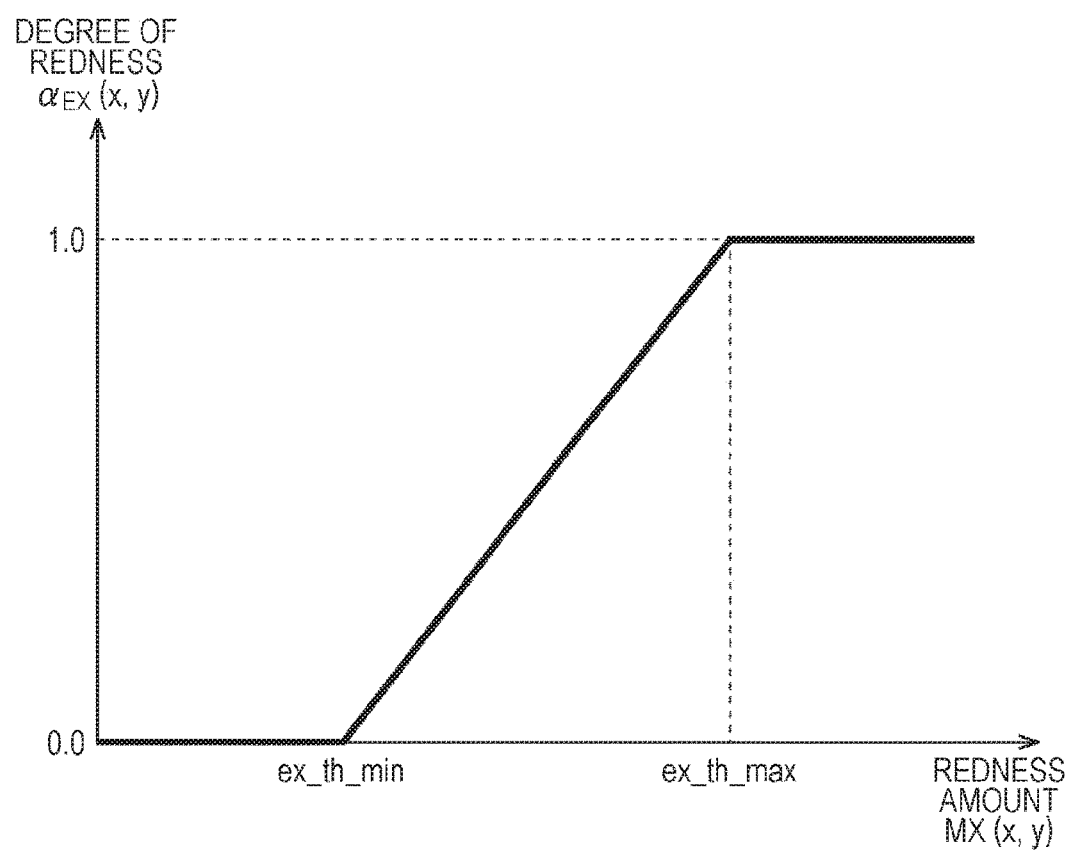
FIG. 46 is a diagram that illustrates an example of a normalized function.

In addition, $A_{EX}$ and $B_{EX}$ are parameters used for calculating a red amount. The red degree calculating unit 511 adjusts the contrast of the red mount by normalizing the red amount EX(x, y) of each position into a value in the range of [0, 1] based on a normalization function illustrated in FIG. 46. The red degree calculating unit 511 outputs information representing the red amount EX(x, y) to the red edge degree calculating unit 512 and outputs a value representing a red amount of each position after the normalization to the local red degree calculating unit 513 as a red degree $\alpha_{EX}(x, y)$.

The red edge degree calculating unit 512 calculates a red edge degree based on the red amount EX(x, y) of each position acquired by the red degree calculating unit 511. The red edge degree is a value that represents the degree of locality of red amount.

The red edge degree calculating unit 512 generates an edge image that is an image representing a difference between the red amount of each position and a red amount of the periphery thereof. As a method for generating an edge image, for example, there is a method using a line extracting filter. Here, the value of the edge image at each position will be represented as ex_edge(x, y).

Figure 47:
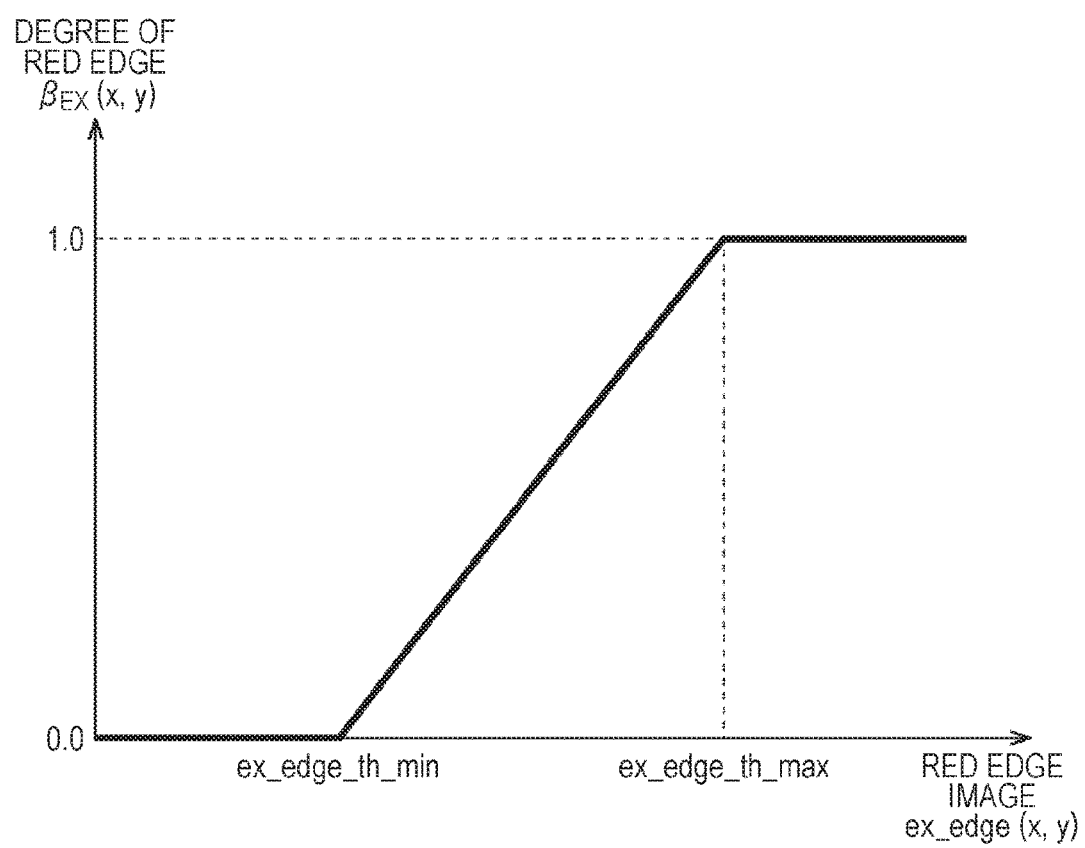
FIG. 47 is a diagram that illustrates another normalized function.

The value of ex_edge(x, y) is high at a portion at which the red amount is locally higher than that of the periphery or a portion at which the red amount is locally lower than that of the periphery. The red edge degree calculating unit 512 normalizes ex_edge(x, y) into a value in the range of [0, 1] based on the normalization function represented in FIG. 47 and outputs a value after the normalization to the local red degree calculating unit 513 as a red edge degree $\beta_{EX}(x, y)$.

The local red degree calculating unit 513 calculates a local red degree $\gamma_{EX}(x, y)$ by performing multiplication of the red degree $\alpha_{EX}(x, y)$ acquired by the red degree calculating unit 511 and the red edge degree $\beta_{EX}(x, y)$ acquired by the red edge degree calculating unit 512. The local red degree $\gamma_{EX}(x, y)$ at a position at which the red degree is higher than that of the periphery has a high value. The local red degree calculating unit 513 outputs information representing the local red degree $\gamma_{EX}(x, y)$ as a result of the analysis of a red spot.

In addition, in a case where an area in which the red degree is high is relatively wide, only the local red degree of the periphery of the area has a high value, and the local red degree of the center portion has a low value. In order to prevent this, the local red degree calculating unit 513, for example, performs a binarization process and performs a process of filling up a detected closed area with a value of the periphery portion.

In this way, the spot analyzing unit 482 calculates the distribution of each component for each of the melanin component and the hemoglobin component. In addition, the spot analyzing unit 482 specifies a position at which the amount of each component is locally high and generates information representing the amount of each component in an area including the specified position as a result of the analysis of the spot.

The methods of analyzing the states of the red spot and the melanin spot are not limited to the methods described above. For example, it may be configured such that the color of each area of a skin image captured by emitting only visible light is detected, an area of a color close to red is specified as an area of a red spot, and an area of a color close to brown is specified as an area of a melanin spot.

Pore Analyzing Unit 481

Figure 48:
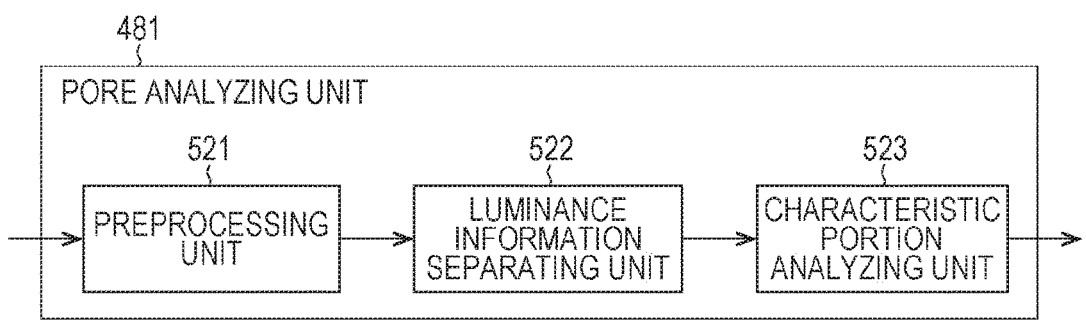
FIG. 48 is a block diagram that illustrates an example of the configuration of a pore analyzing unit.

FIG. 48 is a block diagram that illustrates an example of the configuration of the pore analyzing unit 481 illustrated in FIG. 38.

The pore analyzing unit 481 is configured by; a preprocessing unit 521; a luminance information separating unit 522; and a characteristic portion analyzing unit 523. A skin image output from the skin image acquiring unit 471 is input to the preprocessing unit 521.

The preprocessing unit 521 performs processes of noise elimination, a shading correction, contrast enhancement, and the like for the skin image as preprocessing. The preprocessing unit 521 outputs data of the skin image for which the preprocessing has been performed to the luminance information separating unit 522.

The luminance information separating unit 522 separates luminance information of the skin image after the preprocessing into global luminance information and local luminance information. The global luminance information is information that represents a lighting component included in an image or a structural component of the skin. On the other hand, the local luminance information is information that represents a fine shape of the skin such as texture. The separation of the luminance information, for example, is performed using a low-pass filter. The luminance information separating unit 522 outputs the global luminance information to the characteristic portion analyzing unit 523 together with the skin image.

The characteristic portion analyzing unit 523 calculates a characteristic amount from the skin image and analyzes a characteristic portion of the skin based on the calculated characteristic amount.

Figure 49:
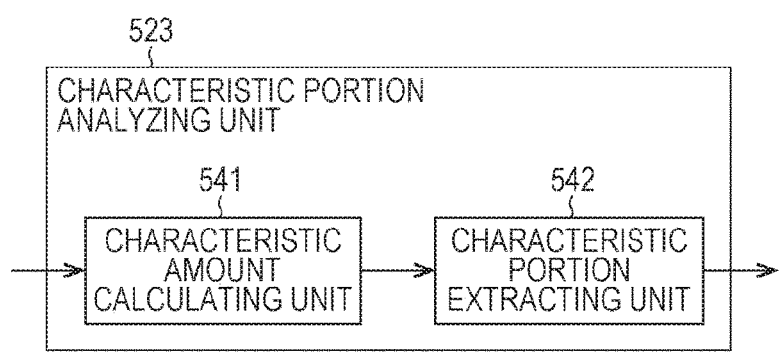
FIG. 49 is a block diagram that illustrates an example of the configuration of a characteristic portion analyzing unit.

FIG. 49 is a block diagram that illustrates an example of the configuration of the characteristic portion analyzing unit 523.

The characteristic portion analyzing unit 523 is configured by: a characteristic amount calculating unit 541; and a characteristic portion extracting unit 542.

The characteristic amount calculating unit 541 calculates a characteristic amount based on the global luminance information separated by the luminance information separating unit 522. For example, the characteristic amount calculating unit 541 calculates polarity relating to the gray scale of the skin image, a scale representing a pixel area having similar pixel values different from those of the periphery, and an intensity representing a signal difference between the image area of similar pixel values and the periphery as characteristic amounts.

For the calculation of characteristic amounts, techniques such as a Speeded Up Robust Feature (SURF) and a Scale Invariant Feature Transform (SIFT) are used. For example, in a case where the SURF is used, the characteristic amount calculating unit 541 searches for a point at which the matrix value of a Hessian matrix that is a characteristic point inside the image is maximum with a standard deviation σ of the Gaussian function being changed.

The characteristic portion extracting unit 542 extracts a pore portion as a characteristic portion based on the characteristic amount acquired by the characteristic amount calculating unit 541. For example, the characteristic portion extracting unit 542 extracts a portion of a characteristic point at which Laplacian representing the polarity relating to the gray scale of the skin image is "1". The Laplacian being "1" represents a characteristic that a black pixel is surrounded by white pixels.

In addition, the characteristic portion extracting unit 542 extracts a portion from which a scale of about 0.1 mm to 0.3 mm is calculated among portions of the characteristic points extracted based on the polarity as a pore portion. Generally, the size of the pore is about 0.1 mm to 0.3 mm.

The characteristic portion extracting unit 542 outputs information of a center position of the characteristic point extracted as the pore portion as information of the position of the pore. In addition, the characteristic portion extracting unit 542 outputs information of the scale of the characteristic point extracted as the pore portion as information representing the degree of opening of the pore. Furthermore, the characteristic portion extracting unit 542 outputs information of the intensity of the characteristic point extracted as the pore portion as information representing the degree of a black spot of the pore.

The information representing the position of the pore, the degree of opening, and the degree of the black spot, which has been output from the characteristic portion extracting unit 542, is supplied to the analysis result acquiring unit 473 as information representing a result of the analysis of the pore state.

The analysis of the pore state as described above is disclosed in Patent Application No. 2012-180861 that is an application filed by the present applicants. The method of analyzing the pore state is not limited to the methods described above.

<4. Operation of Each Apparatus>

Next, the processes of the information processing terminal 1 and the analysis server 3 having the configurations as described above will be described.

First, a skin image transmitting process executed by the information processing terminal 1 will be described with reference to a flowchart illustrated in FIG. 50.

Figure 50:
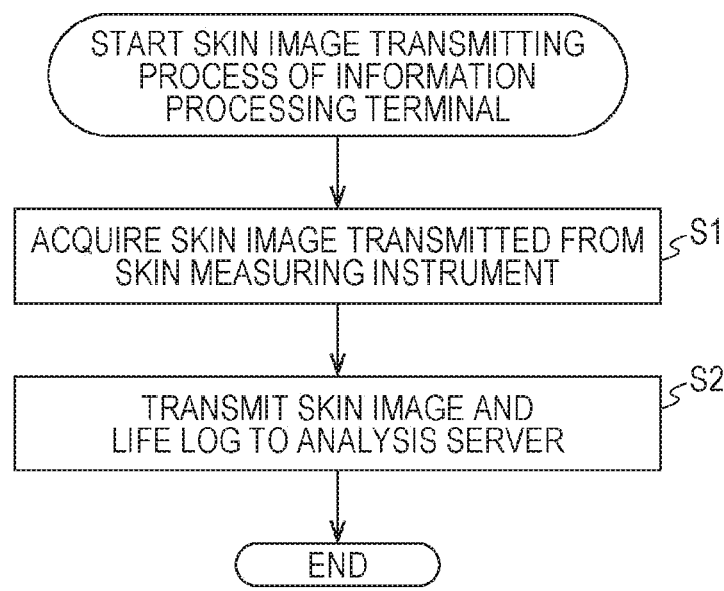
FIG. 50 is a flowchart that illustrates a skin image transmitting process executed by an information processing terminal.

The process illustrated in FIG. 50 is started when a user images his skin by using the skin measuring instrument 2, and a skin image acquired by the imaging process is transmitted from the skin measuring instrument 2. The input of a life-log is performed using an input screen as illustrated in FIG. 23, and the life-log is acquired by the life-log acquiring unit 432 at predetermined timing.

In step S1, the skin image acquiring unit 431 of the information processing terminal 1 acquires a skin image transmitted from the skin measuring instrument 2 by controlling the communication unit 419.

In step S2, the communication control unit 433 transmits the skin image acquired by the skin image acquiring unit 431 and the life-log acquired by the life-log acquiring unit 432 to the analysis server 3 by controlling the communication unit 419. Thereafter, until there is feedback of a result of the measurement of the skin state, the information processing terminal 1 stands by.

Next, a skin state analyzing process executed by the analysis server 3 will be described with reference to a flowchart illustrated in FIG. 51.

Figure 51:
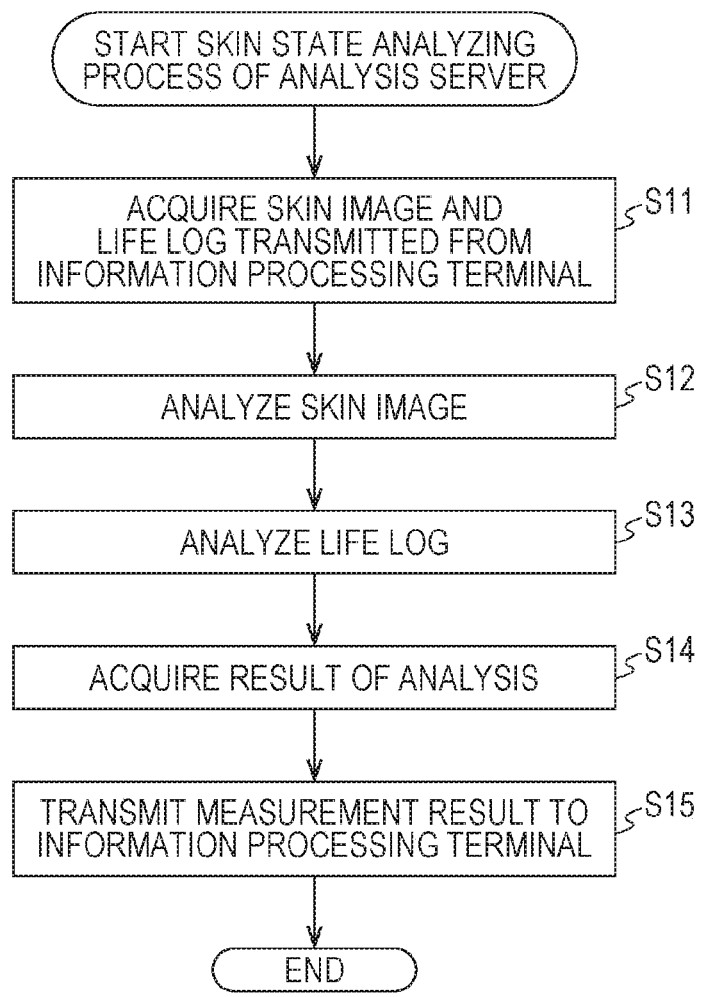
FIG. 51 is a flowchart that illustrates a skin state analyzing process executed by an analysis server.

The process illustrated in FIG. 51 is started when a skin image captured using the skin measuring instrument 2 is transmitted from the information processing terminal 1 together with a life-log.

In step S11, the skin image acquiring unit 471 acquires the skin image transmitted from the information processing terminal 1 by controlling the communication unit 459. In addition, the life-log acquiring unit 474 acquires the life-log transmitted from the information processing terminal 1 by controlling the communication unit 459.

In step S12, the skin analyzing unit 472 analyzes the skin image. In other words, the pore analyzing unit 481, the spot analyzing unit 482, and the texture analyzing unit 483 configuring the skin analyzing unit 472 respectively analyze the states of the pore, the spot, and the texture, as described above. In addition, the moist/oil analyzing unit 484 analyzes a moist amount and an oil amount.

In step S13, the life-log analyzing unit 475 analyzes the life-log and acquires the scores of the life habit and the feeling mood.

In step S14, the analysis result acquiring unit 473 acquires a result of the analysis performed by the skin analyzing unit 472 and acquires the scores of the pore state, the spot state, and the texture state. In addition, the analysis result acquiring unit 473 specifies a user's skin type based on the moist amount and the oil amount. The analysis result acquiring unit 473 acquires the scores of the life habit and the feeling mood acquired by the life-log analyzing unit 475.

In step S15, the presentation unit 476 transmits the information supplied from the analysis result acquiring unit 473 to the information processing terminal 1 as information representing a measurement result of the skin state. Thereafter, the process executed by the analysis server 3 ends.

Figure 52:
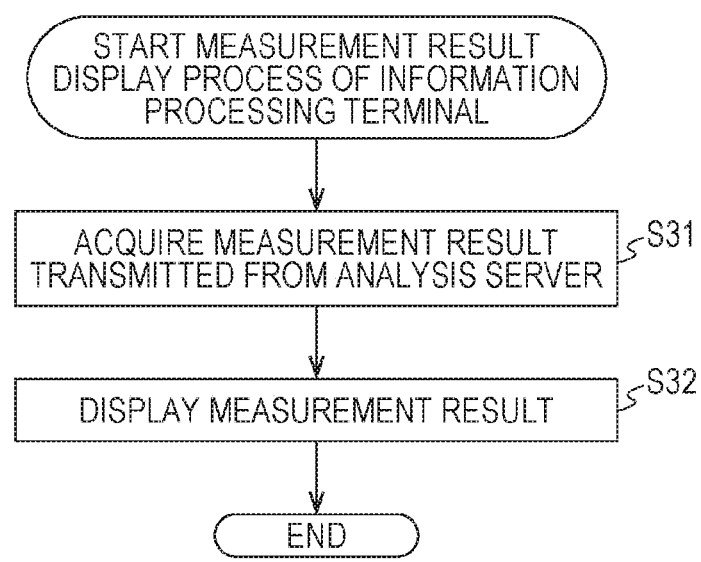
FIG. 52 is a flowchart that illustrates a measurement result display process executed by an information processing terminal.

Next, a measurement result displaying process executed by the information processing terminal 1 will be described with reference to a flowchart illustrated in FIG. 52.

In step S31, the communication control unit 433 of the information processing terminal 1 receives and acquires the information representing an analysis result transmitted from the analysis server 3.

In step S32, the display control unit 434 displays the measurement result display screen described with reference to FIG. 5 and the like on the display 51 based on the information acquired by the communication control unit 433. The display control unit 434 performs switching of the measurement result display screen in accordance with a user's operation. In a case where the measurement result display screen is directed to be closed, the process ends.

In a case where the information of the life habit and the feeling mood of the user are not displayed on the measurement result display screen, the information of the life habit and the feeling mood may not be transmitted from the analysis server 3 to the information processing terminal 1. In addition, while the information of the life habit and the feeling mood of the user is transmitted from the analysis server 3 to the information processing terminal 1, the information may not be used for the display of the measurement result display screen in the information processing terminal 1.

According to the series of the processes described above, the user can check the skin state more intuitively and simply than in a case where the measurement results are displayed simply using numbers, bar graphs or the like.

«Second Embodiment»

FIG. 53 is a diagram that illustrates another example of the configuration of the skin analyzing system.

The skin analyzing system illustrated in FIG. 53 is configured by: an information processing terminal 1; and a skin measuring instrument 2.

The information processing terminal 1 acquires a skin image captured by the skin measuring instrument 2 and analyzes user's skin state based on the acquired skin image. The information processing terminal 1 displays a measurement result display screen on a display 51 based on a result of the analysis. In addition, the life-log is appropriately acquired by the information processing terminal 1 and is used for analyzing the life habit and the feeling mood.

In other words, in the skin analyzing system illustrated in FIG. 53, the analysis of a skin state is performed by the information processing terminal 1, and the measurement result display screen is displayed. The information processing terminal 1 functions as an information processing apparatus performing image processing of the skin image and analyzing the skin state. The information processing terminal 1 has the same configuration as that illustrated in FIG. 38.

«Third Embodiment»

In the description presented above, while a petal chart representing a measurement result of the skin state of one user is displayed on the measurement result display screen, petal charts representing measurement results of skin states of a plurality of users may be displayed on the same measurement result display screen.

Figure 54:
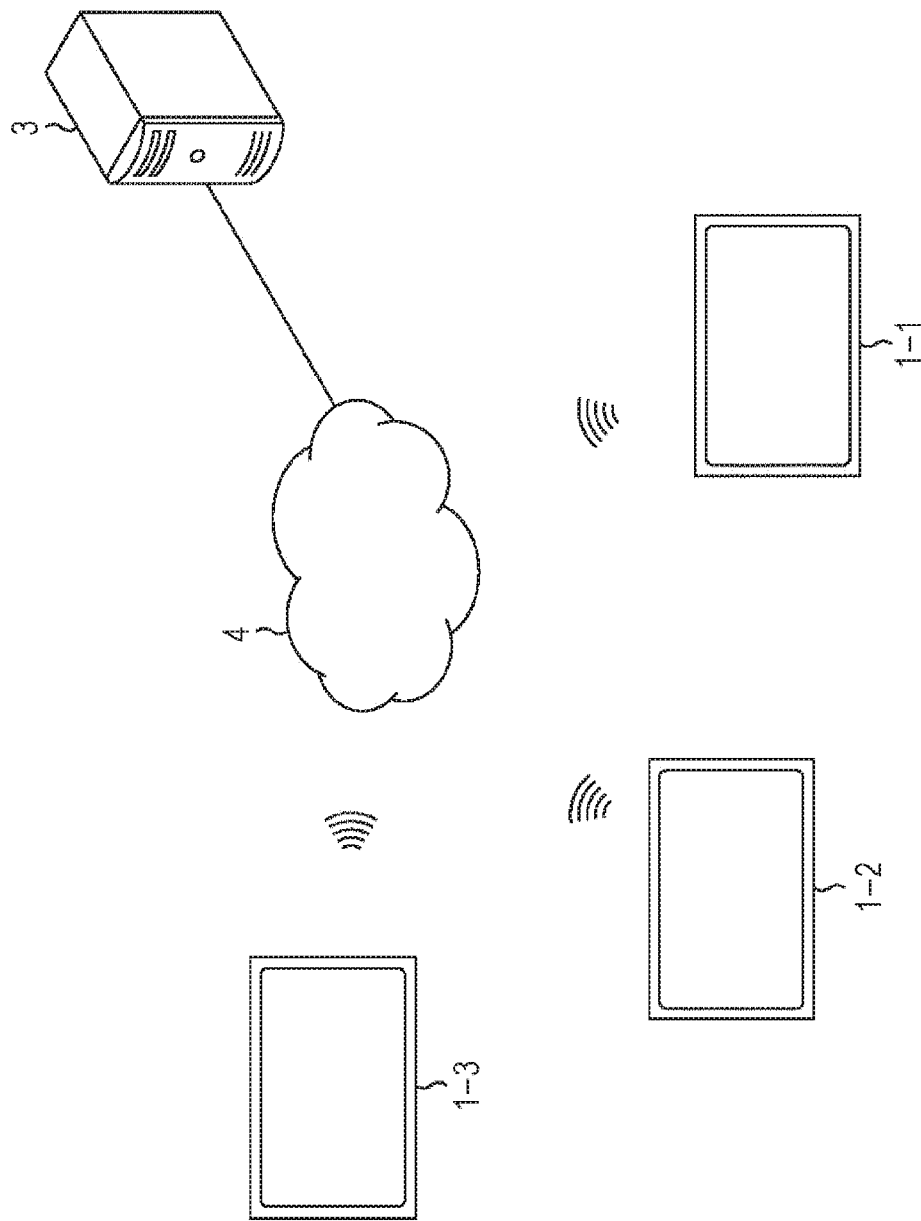
FIG. 54 is a diagram that illustrates further another example of the configuration of the skin analyzing system.

FIG. 54 is a diagram that illustrates further another example of the configuration of the skin analyzing system.

In the example illustrated in FIG. 54, information processing terminals 1-1 to 1-3 are connected to a network 4. Naturally, more information processing terminals are connected to the network 4.

The information processing terminals 1-1 to 1-3 are terminals used by mutually-different users. While not illustrated in the drawing, a skin measuring instrument similar to the skin measuring instrument 2 is connected to the information processing terminals 1-1 to 1-3. Each of the information processing terminals 1-1 to 1-3 acquires user's skin image together with information of the life-log and the like and transmits the acquired information to the analysis server 3.

The analysis server 3 acquires the information transmitted from the information processing terminals 1-1 to 1-3 and analyzes the skin states of the users using the information processing terminals 1-1 to 1-3. The analysis server 3 transmits the information representing measurement results of the skin states of a plurality of users to the information processing terminals 1-1 to 1-3 and displays the measurement result display screen on each display.

Figure 55:
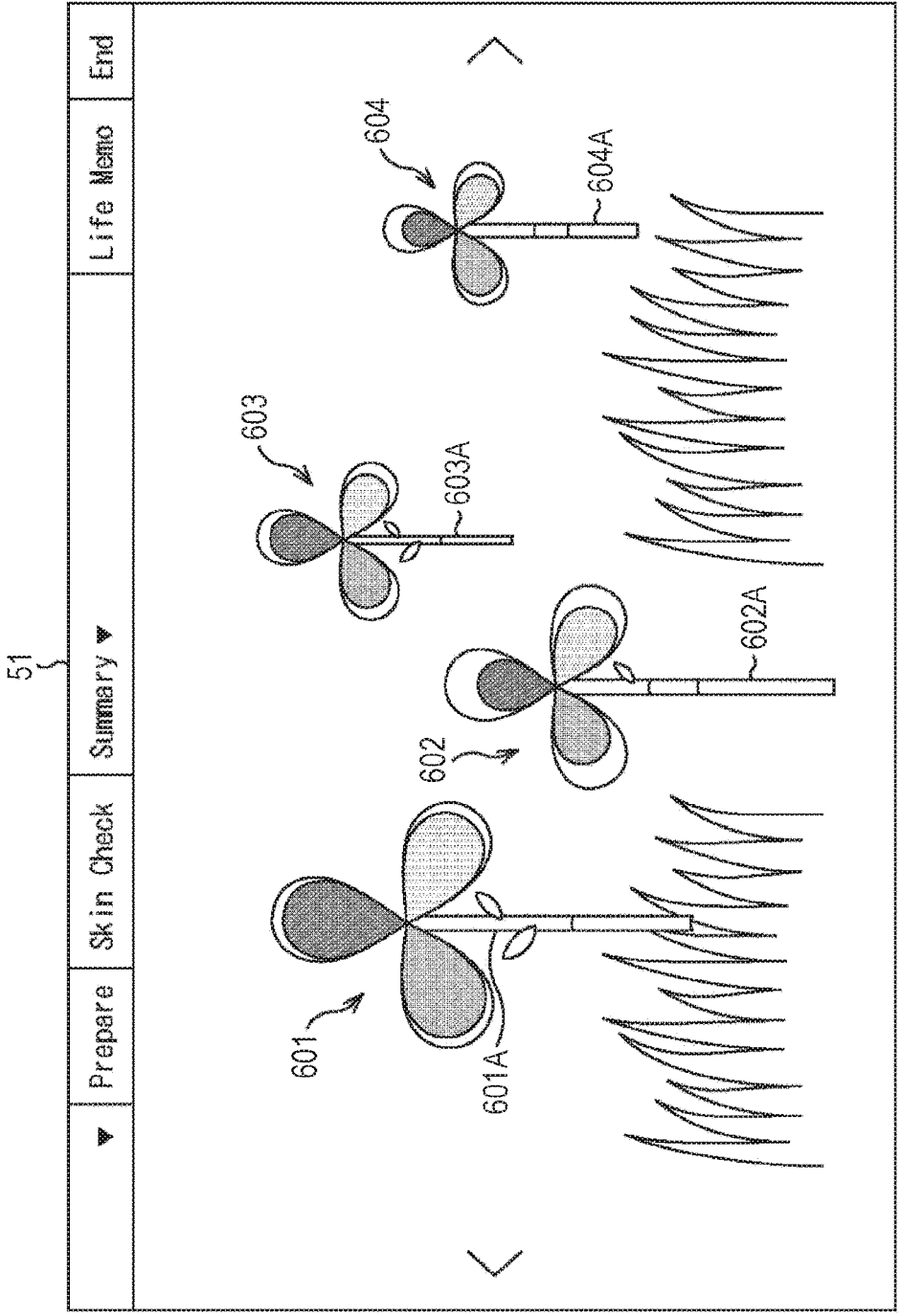
FIG. 55 is a diagram that illustrates a ninth display example of the measurement result display screen.

FIG. 55 is a diagram that illustrates a ninth display example of the measurement result display screen.

In the example illustrated in FIG. 55, four petal charts 601 to 604 representing the measurement results of the skin states of four users are displayed. Under the petal charts 601 to 604, stem images 601A to 604A are respectively displayed.

In this way, by displaying the petal charts representing the measurement results of the skin states of a plurality of users on the same screen, the user can compare his skin state with the skin states of the other users. In addition, since the flower is displayed to be larger as the skin state is better, a sense of comradeship operates with forming a pretty flower garden by growing the flowers altogether as a common object, and the motivation for the care of the skin can be maintained.

By using not only the petal charts and the stem images but also root images and the like, the information of the life habit and the feeling mood of each user may be displayed. Accordingly, the user can refer to the life habit and the feeling mood of another user having a good skin state.

By performing a predetermined operation in a state in which the measurement result display screen illustrated in FIG. 55 is displayed, the whole measurement result display screen or the petal chart representing his own skin state may be converted into images of icons or the like and be stored.

Figure 56:
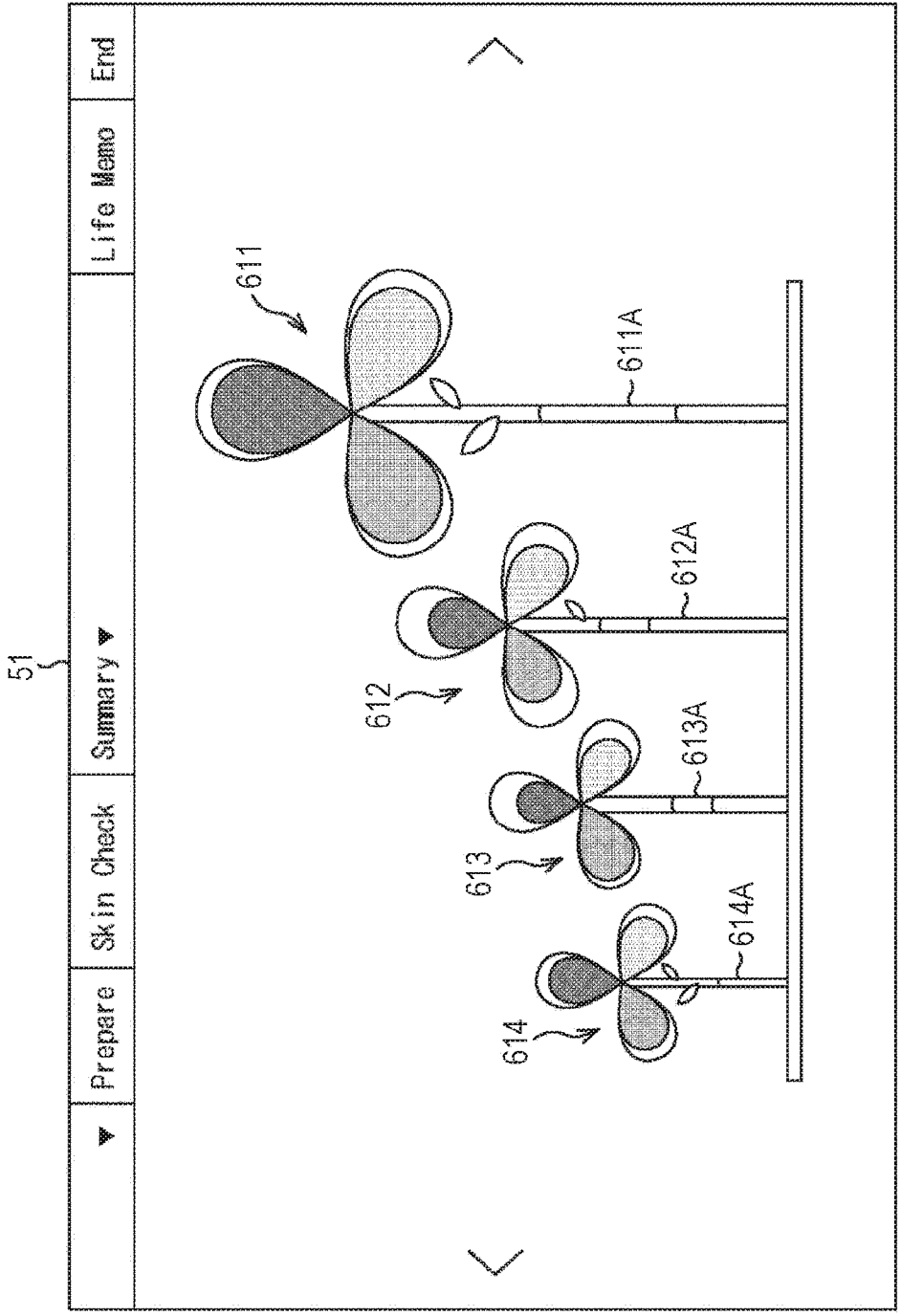
FIG. 56 is a diagram that illustrates a tenth display example of the measurement result display screen.

FIG. 56 is a diagram that illustrates a tenth display example of the measurement result display screen.

In the example illustrated in FIG. 56, four petal charts 611 to 614 representing measurement results of the skin states of four users are aligned and displayed in descending order from the right side of the screen. Under the petal charts 611 to 614, stem images 611A to 614A are respectively displayed.

The measurement result display screen illustrated in FIG. 56 is a screen representing the rank of the skin states in sizes of the petal charts. For example, near each petal chart, user's identification information is displayed. The analysis server 3 sets ranks based on analysis results of the skin states of the plurality of users and displays the petal charts according to the set ranks. Each of the petal charts may be displayed as a still image or be displayed using an animation.

Figure 57:
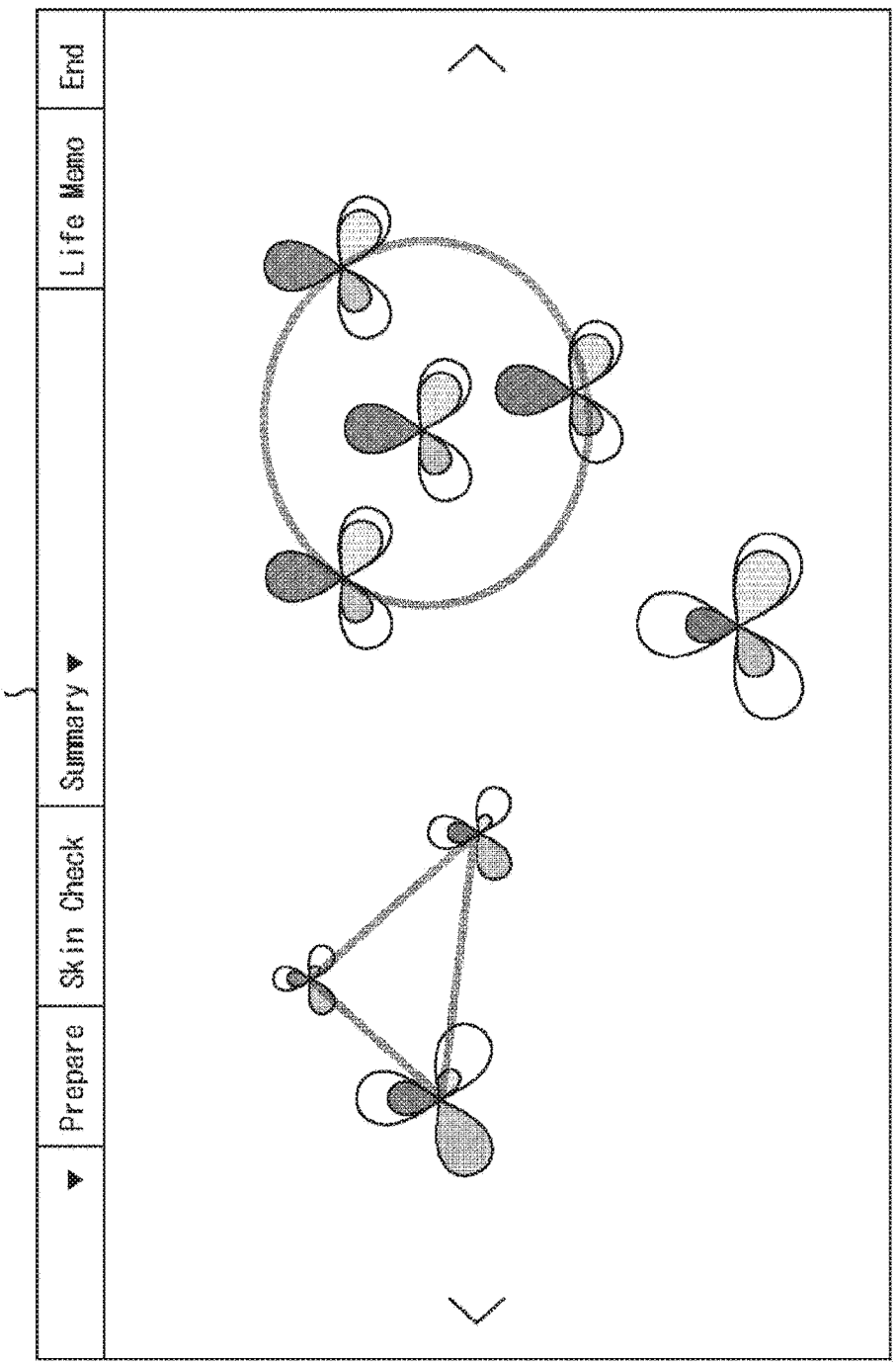
FIG. 57 is a diagram that illustrates an eleventh display example of the measurement result display screen.

FIG. 57 is a diagram that illustrates an eleventh display example of the measurement result display screen.

In the example illustrated in FIG. 57, eight petal charts representing measurement results of the skin states of eight users are displayed. Three petal charts are displayed together on the left side of the screen, and four petal charts are displayed together on the right side of the screen. One remaining petal chart is displayed on the lower center side of the screen.

For example, the petal charts are displayed at positions corresponding to the measurement results such that petal charts representing similar measurement results are arranged near. The analysis server 3 divides groups based on the analysis results of the skin states of the plurality of users and determines the display positions of the petal charts. The criterion used for the grouping may be arbitrarily changed like a case where measurement results of users having similar life habits or similar feeling moods are arranged near without depending on the similarity of the measurement results.

«Modified Example»

<1. Display Example in Another Apparatus>

As above, while a case has been described in which the measurement result display screen is displayed in the information processing terminal 1 that is a tablet-type terminal, the measurement result display screen may be displayed on the display of another terminal.

Figure 58:
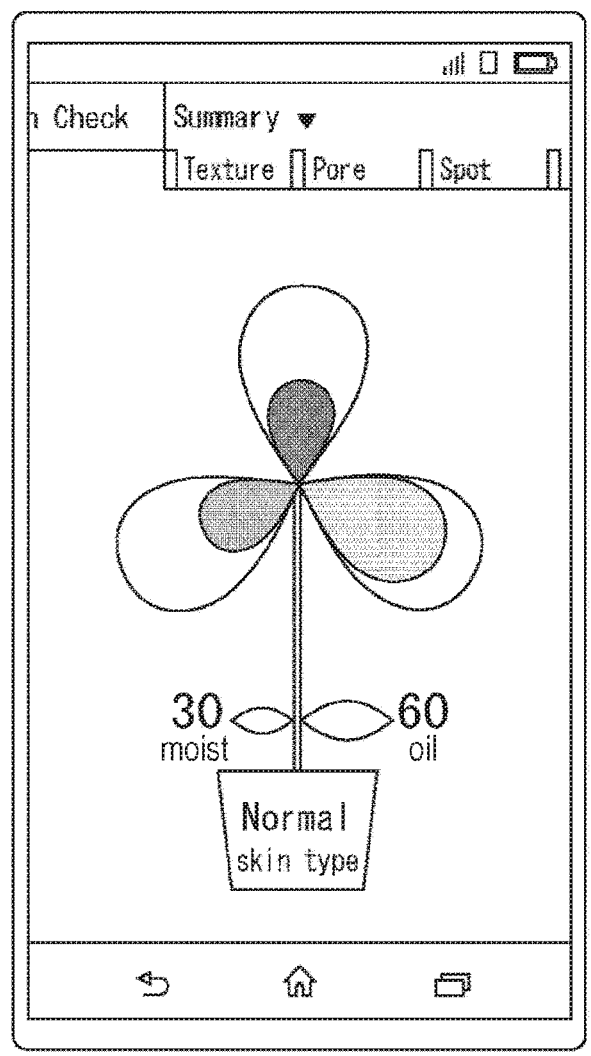
FIG. 58 is a diagram that illustrates an example of the display executed by a mobile telephone.

FIG. 58 is a diagram that illustrates an example of the display executed in a mobile telephone.

In the example illustrated in FIG. 58, an image including petal charts is displayed on the display of a so-called smartphone. An image illustrated in FIG. 58 is an image similar to the image illustrated in FIG. 11 except that the flower head area 111 is not arranged FIGS. 59 to 62 are diagrams that illustrate other examples of the display executed by a mobile telephone.

Figure 59:
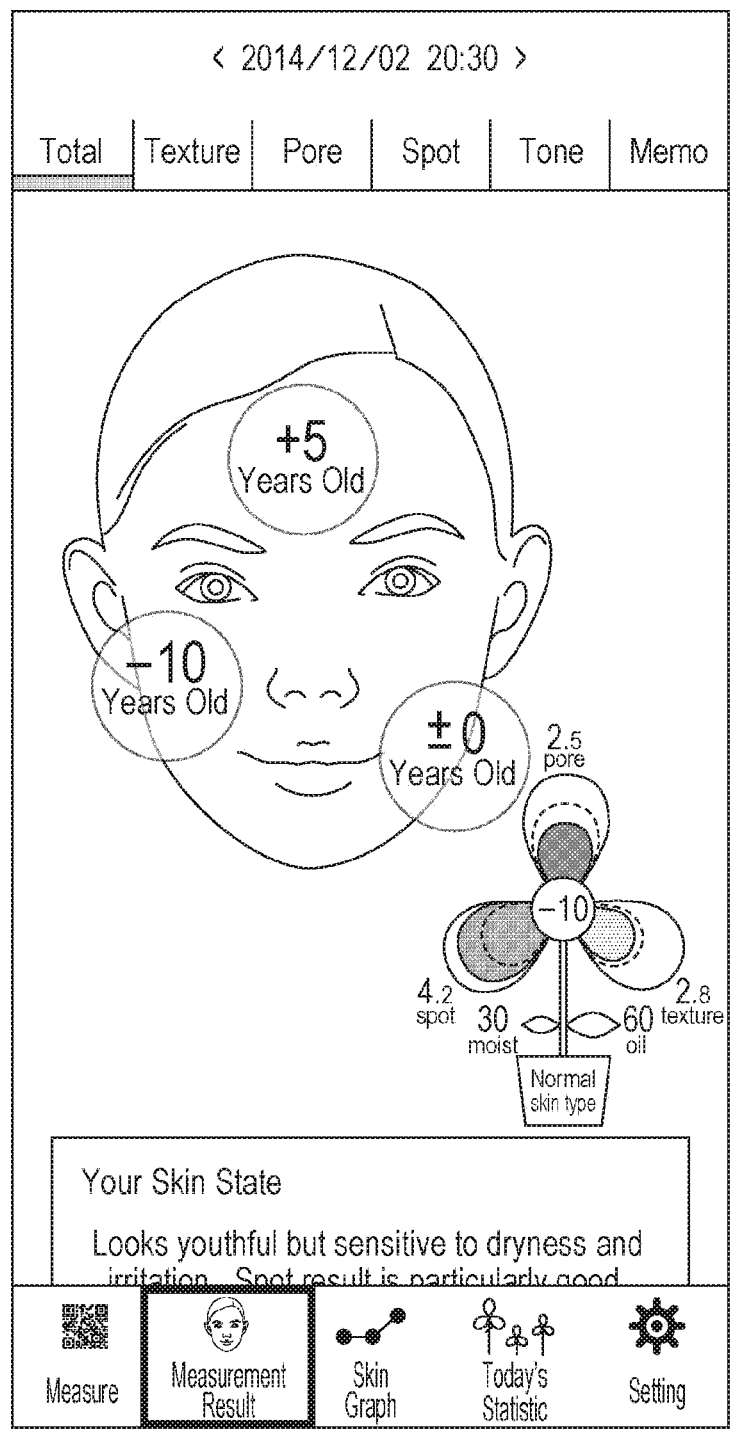
FIG. 59 is a diagram that illustrates an example of the display executed in a mobile telephone.
Figure 60:
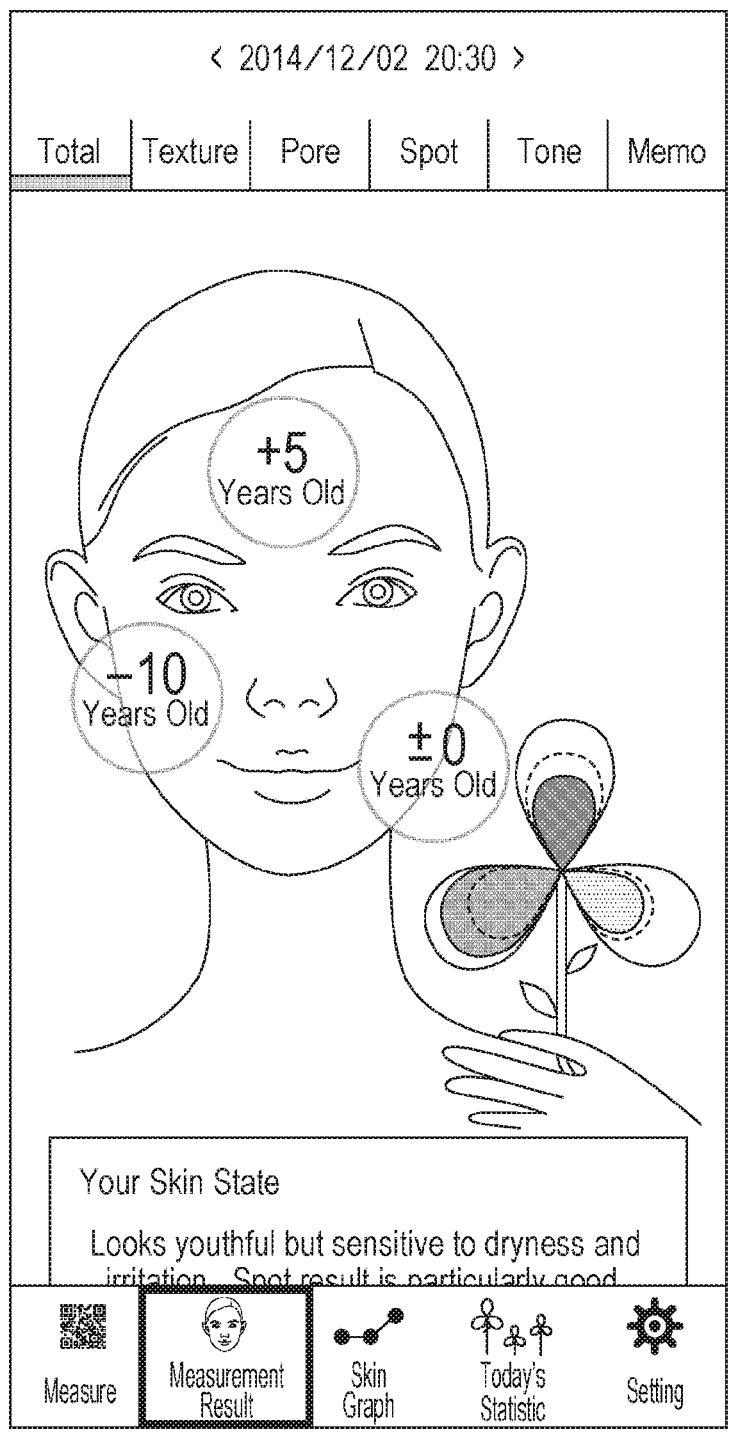
FIG. 60 is a diagram that illustrates an example of the display executed in a mobile telephone.
Figure 61:
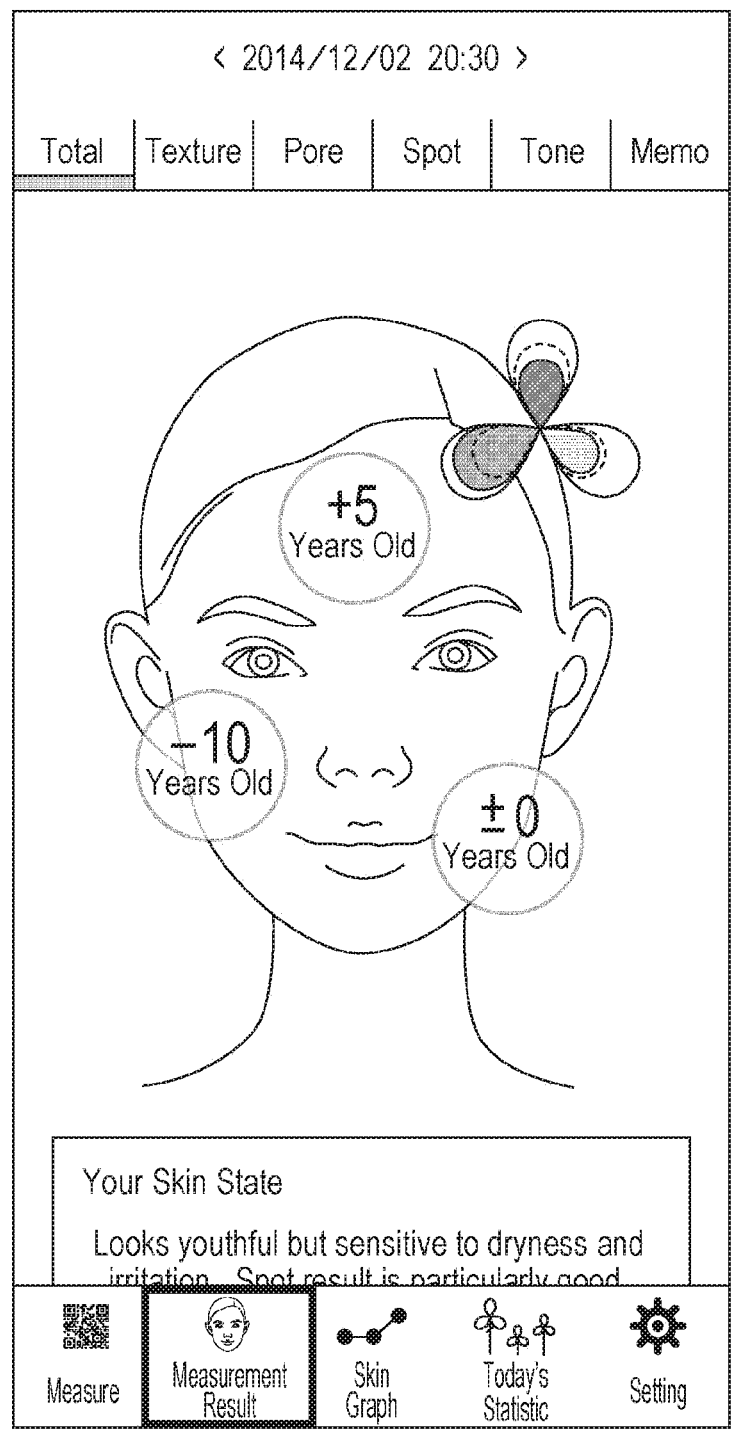
FIG. 61 is a diagram that illustrates an example of the display executed in a mobile telephone.

In the examples illustrated in FIGS. 59 to 61, a petal chart is displayed together with an illustration 61 (FIG. 5) of a face of a person facing the front side. In the forehead, the cheek, and the mouth of the illustration 61, icons each representing the skin age of each position are displayed. The user can align the petal charts in accordance with the skin ages of the positions.

Figure 62:
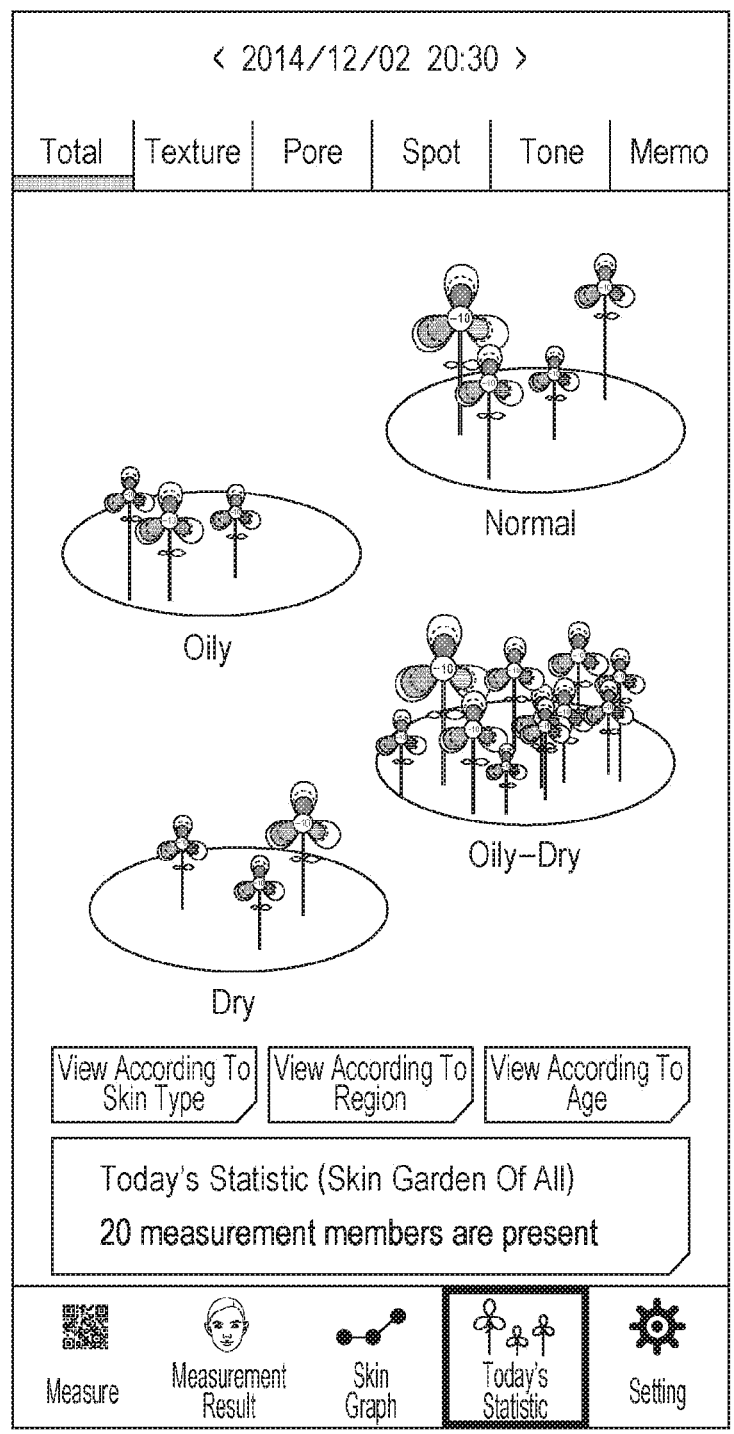
FIG. 62 is a diagram that illustrates an example of the display executed in a mobile telephone.

On the other hand, in the example illustrated in FIG. 62, a plurality of petal charts are displayed with being arranged for each skin type of users.

In this way, not only the measurement result display screen including a petal chart representing a measurement result of one user, but also the measurement result display screen including petal charts representing measurement results of a plurality of users may be displayed on the display of the mobile telephone. In addition, the measurement result display screen, for example, illustrated in FIG. 62, including petal charts representing measurement results of a plurality of users may be displayed on a screen unit of a projection system illustrated in FIG. 66 or a large display illustrated in FIG. 67, which will be described later.

Figure 63:
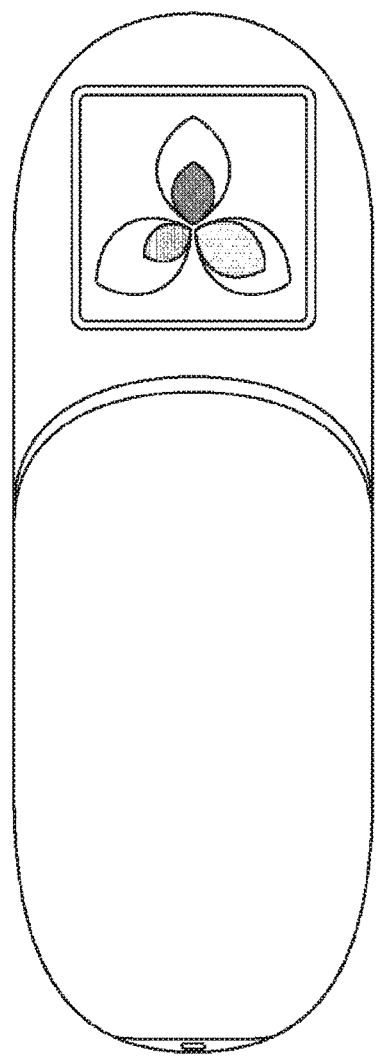
FIG. 63 is a diagram that illustrates an example of display executed in a skin measuring instrument.

FIG. 63 is a diagram that illustrates an example of display executed in the skin measuring instrument 2.

In a case where a small display is disposed in the skin measuring instrument 2, as illustrated in FIG. 63, a petal chart may be displayed on the display of the skin measuring instrument 2. The petal chart illustrated in FIG. 63 is the petal chart illustrated in FIG. 24A.

The petal chart illustrated in FIG. 63 may be configured to be displayed based on the information transmitted from the analysis server 3 or displayed based on the information recorded in the skin measuring instrument 2 in advance. In the latter case, in the skin measuring instrument 2, configurations that are the same as those illustrated in FIG. 38 are disposed, and the petal chart is displayed based on the information acquired by analyzing the skin image in the skin measuring instrument 2.

Figure 64:
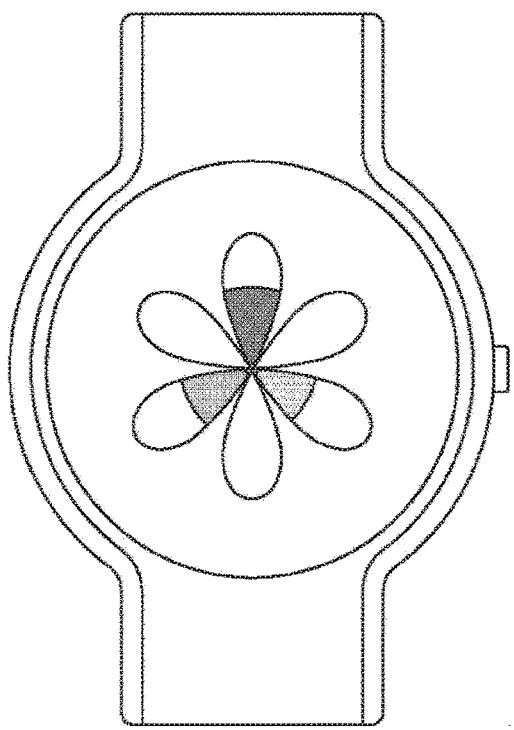
FIG. 64 is a diagram that illustrates an example of the display executed in a wrist-watch type mobile terminal.

FIG. 64 is a diagram that illustrates an example of the display executed in a wrist-watch type mobile terminal.

As illustrated in FIG. 64, a petal chart may be configured to be displayed on a circular display disposed in the wrist-watch type mobile terminal. The petal chart illustrated in FIG. 64 is the petal chart illustrated in FIG. 25B. The wrist-watch type mobile terminal illustrated in FIG. 64 has a communication function in addition to an image display function.

The petal chart illustrated in FIG. 64 may be configured to be displayed based on the information transmitted from the analysis server 3 or be displayed based on the information recorded in the wrist-watch type mobile terminal in advance. In the latter case, configurations that are the same as those illustrated in FIG. 38 are disposed in the wrist-watch type mobile terminal, and the petal chart is displayed based on the information acquired by analyzing the skin image in the wrist-watch type mobile terminal.

Figure 65:
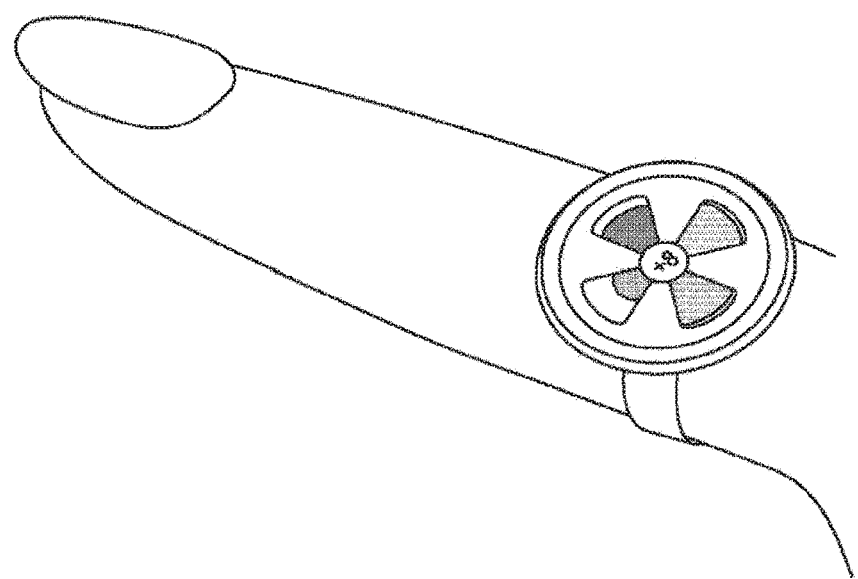
FIG. 65 is a diagram that illustrates an example of the display executed in a ring-type mobile terminal.

FIG. 65 is a diagram that illustrates an example of the display executed in a ring-type mobile terminal.

The ring-type mobile terminal illustrated in FIG. 65, as illustrated in FIG. 65, is a terminal that is used by a user mounting the mobile terminal in a finger. As illustrated in FIG. 65, a petal chart may be displayed on a circular display disposed in the ring-type mobile terminal. Similarly to the wrist-watch type mobile terminal illustrated in FIG. 64, the ring-type mobile terminal illustrated in FIG. 65 has a communication function in addition to an image display function.

The petal chart illustrated in FIG. 65 may be configured to be displayed based on the information transmitted from the analysis server 3 or be displayed based on the information recorded in the ring-type mobile terminal in advance. In the latter case, configurations that are the same as those illustrated in FIG. 38 are disposed in the ring-watch type mobile terminal, and the petal chart is displayed based on the information acquired by analyzing the skin image in the ring-type mobile terminal.

Figure 66:
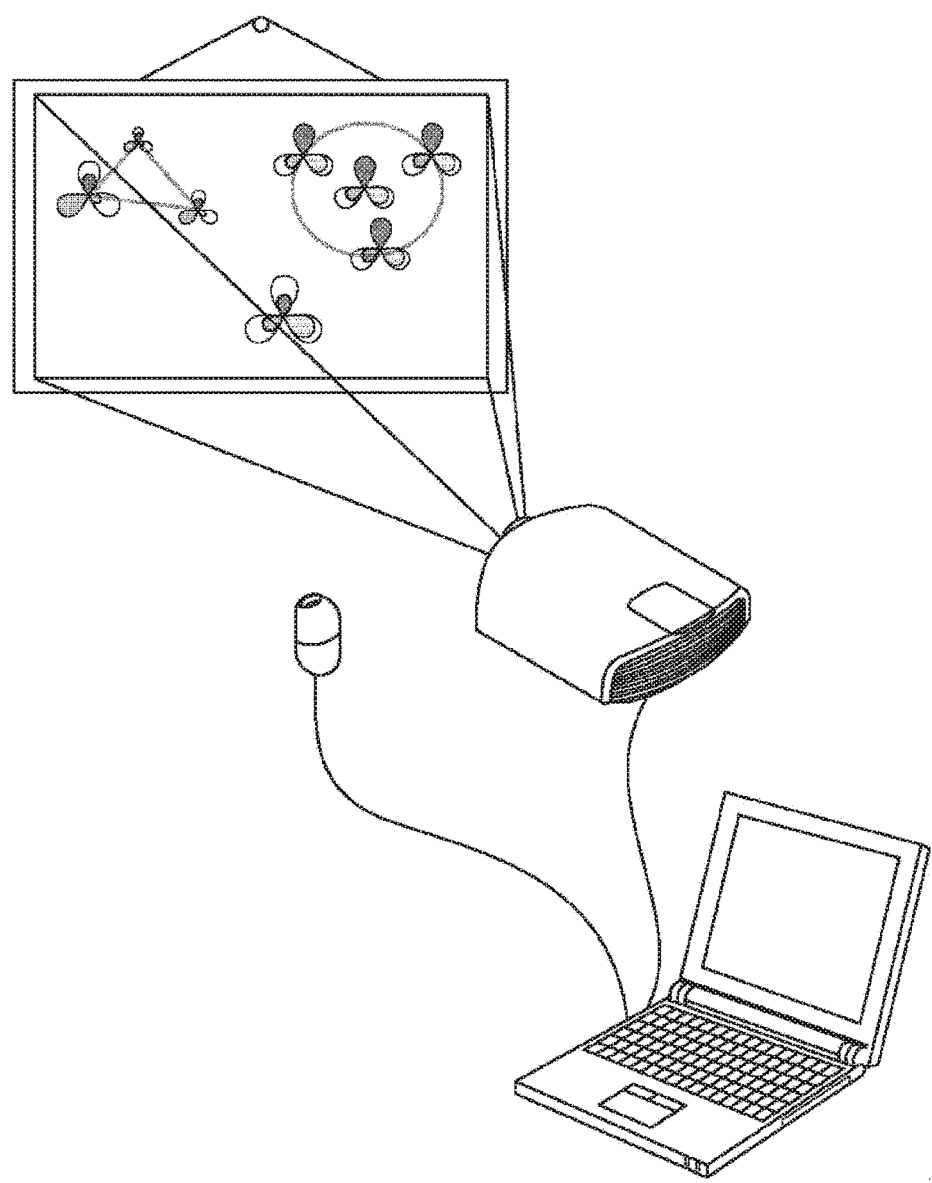
FIG. 66 is a diagram that illustrates an example of the display executed in a projection system.

FIG. 66 is a diagram that illustrates an example of the display executed in a projection system.

The projection system illustrated in FIG. 66 is configured by: an imaging unit (skin measuring instrument 2); an electronic calculation unit that is a so-called laptop PC; a projection unit that is a projector; and a screen unit.

The imaging unit is used for capturing a skin image. The electronic calculation unit measures user's skin state by analyzing the skin image captured by the imaging unit, displays a measurement result display screen on the display unit, and outputs data of the measurement result display screen to the projection unit. The projection unit projects the same screen as the screen displayed on a display unit of the electronic calculation unit to the screen unit based on the data supplied from the electronic calculation unit. The imaging unit, the electronic calculation unit, and the projection unit are connected together, as illustrated in FIG. 66, and are used.

As illustrated in FIG. 66, a measurement result display screen including a petal chart may be displayed on the screen unit. The measurement result display screen displayed on the screen unit illustrated in FIG. 66 is the measurement result display screen described with reference to FIG. 57. The imaging unit and the projection unit may be directly connected and used. In such a case, for example, the imaging unit transmits the skin image to the analysis server 3 through the network 4 and receives information representing a measurement result transmitted from the analysis server 3. The imaging unit outputs the data of the measurement result display screen to the projection unit, thereby displaying the measurement result display screen on the screen unit.

The projection system illustrated in FIG. 66 is sold with four units configuring the projection system as one body and is installed to a beauty shop, a beauty salon, a cosmetic selling store of a department store, or the like.

Figure 67:
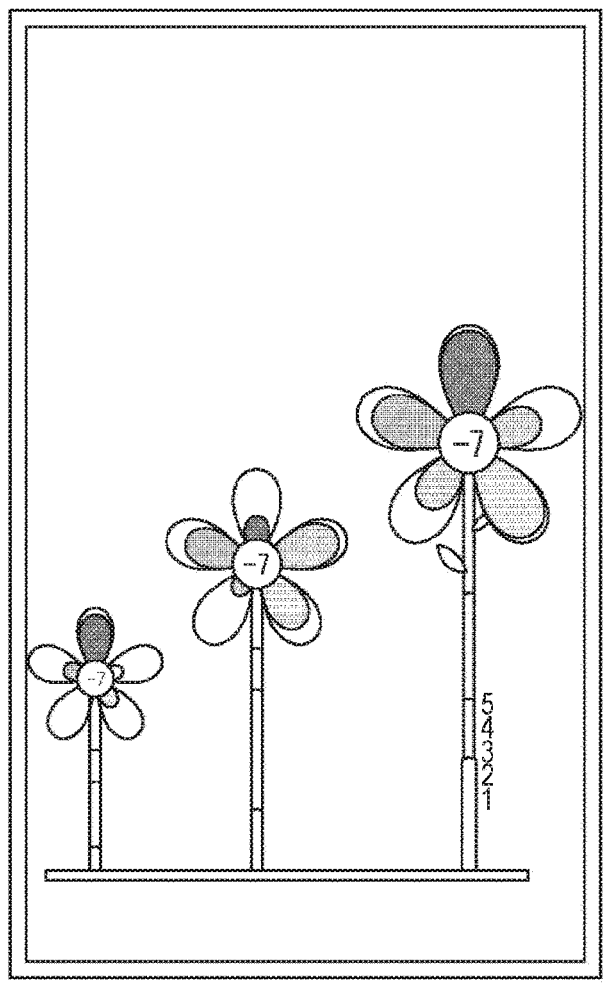
FIG. 67 is a diagram that illustrates an example of the display executed in an image display.

FIG. 67 is a diagram that illustrates an example of the display executed in an image display.

The image display illustrated in FIG. 67 includes a large display and, for example, is installed to a building, a station yard, or the like that is visible to many persons. As illustrated in FIG. 67, a measurement result display screen including petal charts may be configured to be displayed on the large display. The measurement result display screen illustrated in FIG. 67, as described with reference to FIG. 56, is a screen in which petal charts are aligned and displayed in a predetermined order. The image display illustrated in FIG. 67 has a communication function in addition to an image display function.

The measurement result display screen illustrated in FIG. 67 may be configured to be displayed based on the information transmitted from the analysis server 3 or be displayed based on information recorded in the image display in advance. In the latter case, configurations that are the same as those illustrated in FIG. 38 are disposed in the image display, and the petal charts are displayed based on the information acquired by analyzing the skin image in the image display.

<2. Other Example>

Various displays of the petal chart and the measurement result display screen as described above may be arbitrarily combined. For example, the flower head area 111 described with reference to FIG. 11 may be displayed in the petal charts illustrated in FIGS. 24A, 24B, 24C and 25. In addition, the number of petal areas configuring the petal chart illustrated in FIGS. 24A, 24B, 24C and 25, as described with reference to FIG. 16, may be configured to be appropriately changeable. Furthermore, a plurality of petal charts illustrated in FIGS. 24A, 24B, 24C and 25 may be displayed on the same screen.

An animation of the score image immediately after the start of the display described with reference to FIG. 17 may be applied to the display of score images of another petal chart. The petal chart displayed on the display of each of the articles illustrated in FIGS. 58 to 67 may be changed to another petal chart.

In the description presented above, while a case has been described in which the skin measuring instrument 2 is used as a device used for capturing a skin image, the skin image may be captured using a camera 416 mounted in the information processing terminal 1.

In the description presented above, while a case where the skin state of a face is analyzed has been described, a portion of the skin to be analyzed may be a portion other than the face such as a hand, an arm, or a foot.

Program

A series of the processes described above can be performed either by hardware or by software. In a case where the series of the processes is executed by software, a program configuring the software is installed to a computer built into dedicated hardware, a general purpose personal computer, or the like.

The program to be installed is provided with being recorded on the removable medium 421 illustrated in FIG. 35 that is configured by an optical disc (a Compact Disc-Read Only Memory (CD-ROM), a Digital Versatile Disc (DVD), or the like), a semiconductor memory, or the like. In addition, the program may be provided through a wired or wireless transmission medium such as a local area network, the Internet, or digital broadcast. The program may be installed to the ROM 412 or the memory 418 in advance.

In addition, the program executed by the computer may be a program that executes the processes in a time series along the sequence described in this specification or a program that executes the processes in a parallel manner or at necessary timing such as at the timing of being called.

In this specification, a system represents a set of a plurality of constituent elements (an apparatus, a module (component), and the like, and all the constituent elements are not necessarily disposed in a same casing. Thus, a plurality of apparatuses that are housed in separate casings and are connected through a network and one apparatus in which a plurality of modules are housed in one casing are systems.

The effects described here are merely examples but are not for the purposes of limitation, and any other effect may be present.

In addition, the present technology is not limited to the embodiments described above, and various changes can be made therein in a range not departing from the concept of the present technology.

For example, the present technology may employ a configuration of cloud computing in which one function is divided into and processed altogether by a plurality of apparatuses through a network.

In addition, each step described in each flowchart described above may be either executed by one apparatus or executed by a plurality of apparatuses in a shared manner.

Furthermore, in a case where a plurality of processes are included in one step, the plurality of processes included in the one step may be either executed by one apparatus or executed by a plurality of apparatuses in a shared manner.

Examples of Combinations of Configurations

The present technology may take the following configurations.

(1)

An apparatus for displaying a first image representing multiple parameters of biological information, the apparatus including circuitry configured to receive data values for the multiple parameters and prepare first image data that, when rendered on a display, forms from the first image data an image of a living plant, wherein the multiple parameters are represented on the display as portions of the living plant.

(2)

The apparatus of (1), wherein the biological information is representative of human skin quality.

(3)

The apparatus of (1) or (2), further comprising the display.

(4)

The apparatus of any of (1) to (3), wherein the multiple parameters comprise moisture, wrinkle, and clarity.

(5)

The apparatus of any of (1) to (4), wherein the first image is an image of a flower and at least two of the multiple parameters are represented on the display as petals of the flower.

(6)

The apparatus of (5), wherein the apparatus is configured to render the petals in different colors that correspond to different parameters of the multiple parameters.

(7)

The apparatus of (5) or (6), wherein a size of a petal corresponds to a measured value of a respective parameter of the multiple parameters.

(8)

The apparatus of any of (5) to (7), wherein the number of petals is settable by a user.

(9)

The apparatus of any of (5) to (8), wherein the circuitry is further configured to display a petal in association with a number corresponding to a measured value of a respective parameter of the multiple parameters.

(10)

The apparatus of any of (5) to (9), wherein a center of a blossom on the flower indicates a combined score of measured values for the multiple parameters.

(11)

The apparatus of any of (5) to (10), wherein at least one of the multiple parameters is rendered on the display as a leaf on a stem of the flower.

(12)

The apparatus of any of (1) to (11), wherein the circuitry is further configured to prepare second image data that, when rendered on the display, forms a second image of a living plant for comparison with the first image.

(13)

The apparatus of (12), wherein the second image is formed using values of the multiple parameters that were received by the circuitry at a different time.

(14)

The apparatus of any of (1) to (13), wherein the circuitry is further configured to receive data representative of one or more life habits of a user and prepare second image data that, when rendered on the display, forms an image of roots of the living plant, wherein the one or more life habits are represented on the display as portions of the roots.

(15)

The apparatus of (14), wherein the one or more life habits comprise sleep and exercise.

(16)

A data storage device containing machine-readable instructions that, when executed by a processor that is in communication with a display of an apparatus, adapt the apparatus to receive data values corresponding to multiple parameters of human skin quality; prepare first image data from the received data values; form from the first image data a first image; and render the first image on the display, wherein the multiple parameters are represented on the display as portions of a living plant.

(17)

The data storage device of (16), wherein the first image is an image of a flower and at least two of the multiple parameters are represented on the display as different petals of the flower.

(18)

The data storage device of (17), wherein a size of a first petal corresponds to a measured value of a first parameter of the multiple parameters.

(19)

The data storage device of any of (16) to (18), wherein the machine-readable instructions further adapt the apparatus to prepare second image data; and render the second image data on the display as a second image of a living plant for comparison with the first image.

(20)

The data storage device of any of (16) to (19), wherein the machine-readable instructions further adapt the apparatus to receive data representative of one or more life habits of a user; prepare second image data; and
render on the display, from the second image data, an image of roots of the living plant, wherein the one or more life habits are represented on the display as portions of the roots.

(17)

An information processing apparatus including:
an acquisition unit that acquires information representing measurement results of a user's skin state; and
a presentation unit that displays a chart image configured by arranging a plurality of areas, to which a plurality of items of the measurement results are assigned, having a same shape and a same size in respective directions with a predetermined position used as the center and arranging score images representing scores of the items inside each of the areas so as to have sizes corresponding to the scores and to expand from the predetermined position.

(18)

The information processing apparatus according to (17), wherein the presentation unit displays the score images arranged inside each of the areas in mutually-different colors.

(19)

The information processing apparatus according to (17) or (18), wherein the presentation unit displays the chart image such that shapes of the score images representing mutually-different scores are almost similar shapes.

(20)

The information processing apparatus according to any of (17) to (19), wherein the presentation unit displays the chart image in which information representing a reference score is arranged inside each of the areas.

(21)

The information processing apparatus according to any of (17) to (20), wherein the presentation unit displays the chart image in which the plurality of areas are arranged with a display area of predetermined information included in the measurement results disposed at the center.

(22)

The information processing apparatus according to (21), wherein the presentation unit displays information representing a comprehensive evaluation of the user's skin state in the display area.

(23)

The information processing apparatus according to any of (17) to (22), wherein the presentation unit changes the number of the areas configuring the chart image in accordance with a change in the number of the items of which the scores are displayed.

(24)

The information processing apparatus according to any of (17) to (23), wherein the presentation unit displays a plurality of the chart images to be aligned in measurement order.

(25)

The information processing apparatus according to (24), wherein the presentation unit displays the chart images above images of bar shapes having heights corresponding to comprehensive evaluations of the user's skin state.

(26)

The information processing apparatus according to any of (17) to (25), wherein the presentation unit displays the chart image together with information relating to a life habit of the user.

(27)

The information processing apparatus according to (26), wherein the presentation unit displays the chart image arranged above an image of a bar shape having a height corresponding to a comprehensive evaluation of the user's skin state above a boundary image representing a boundary of areas and displays a graph image representing the life habit of the user using a bar graph at a position with the boundary image on an extending line of the image having the bar shape interposed therebetween.

(28)

The information processing apparatus according to any of (17) to (27), wherein the presentation unit displays a plurality of the chart images representing measurement results of skin states of mutually-different users on a same screen.

(29)

The information processing apparatus according to (28), wherein the presentation unit displays the plurality of the chart images to be aligned in order of better measurement results of the skin states.

(30)

The information processing apparatus according to any of (17) to (29), wherein the areas configuring the chart image are areas having approximately petal shapes.

(31)

An information processing method including:
acquiring information representing measurement results of a user's skin state; and
displaying a chart image configured by arranging a plurality of areas, to which a plurality of items of the measurement results are assigned, having a same shape and a same size in respective directions with a predetermined position used as the center and arranging score images representing scores of the items inside each of the areas so as to have sizes corresponding to the scores and to expand from the predetermined position.

(32)

A program causing a computer to execute:
acquiring information representing measurement results of a user's skin state; and
displaying a chart image configured by arranging a plurality of areas, to which a plurality of items of the measurement results are assigned, having a same shape and a same size in respective directions with a predetermined position used as the center and arranging score images representing scores of the items inside each of the areas so as to have sizes corresponding to the scores and to expand from the predetermined position.

REFERENCE SIGNS LIST

1 Information processing terminal
2 Skin measuring instrument
3 Analysis server
51 Display
431 Skin image acquiring unit
432 Life-log acquiring unit
433 Communication control unit
434 Display control unit
471 Skin image acquiring unit
472 Skin analyzing unit
473 Analysis result acquiring unit
474 Life-log acquiring unit
475 Life-log analyzing unit
476 Presentation unit
481 Pore analyzing unit
482 Spot analyzing unit
483 Texture analyzing unit
484 Moist/oil analyzing unit

The invention claimed is:

1. An apparatus, comprising:
a display screen; and
circuitry configured to:
receive data values for a plurality of parameters of biological information;
prepare first image data based on the received data values;
generate a first image based on the first image data, wherein the first image is an image of a flower of a plant, wherein the plurality of parameters represents portions of the plant, and wherein at least two parameters of the plurality of parameters represent a plurality of petals of the flower; and
display a petal of the plurality of petals on the display screen, wherein the petal is associated with a number that corresponds to a measured value of a respective parameter of the plurality of parameters.

2. The apparatus of claim 1, wherein the biological information is representative of human skin quality.

3. The apparatus of claim 1, wherein the plurality of parameters comprises moisture, wrinkle, and clarity.

4. The apparatus of claim 1, wherein the circuitry is further configured to render, on the display screen, the plurality of petals in different colors, and wherein the plurality of petals corresponds to different parameters of the plurality of parameters.

5. The apparatus of claim 1, wherein a size of the petal of the plurality of petals corresponds to the measured value of the respective parameter of the plurality of parameters.

6. The apparatus of claim 1, wherein a count of the plurality of petals is based on a user input.

7. The apparatus of claim 1, wherein a center of a blossom on the flower indicates a combined score of measured values for the plurality of parameters.

8. The apparatus of claim 1, wherein the circuitry is further configured to render at least one parameter of the plurality of parameters on the display screen as a leaf on a stem of the flower.

9. The apparatus of claim 1, wherein the circuitry is further configured to:
prepare second image data to generate a second image of the plant;
generate the second image of the plant based on the second image data; and
compare the first image with the second image.

10. The apparatus of claim 9, wherein the circuitry is further configured to:
receive values of the plurality of parameters at a specific time; and
generate the second image based on the values of the plurality of parameters.

11. The apparatus of claim 1, wherein the circuitry is further configured to:
receive data representative of at least one user life habit;
prepare second image data based on the received data;
generate the second image based on the second image data, wherein the second image is an image of roots of the plant, and wherein the at least one user life habit represents portions of the roots.

12. The apparatus of claim 11, wherein the at least one user life habit comprises sleep and exercise.

13. A non-transitory computer-readable medium having stored thereon computer-executable instructions that, when executed by a processor that is in communication with a display screen of an apparatus, cause the apparatus to execute operations, the operations comprising:
receiving data values corresponding to a plurality of parameters of human skin quality;
preparing first image data based on the received data values;
generating a first image based on the first image data, wherein the first image is an image of a flower of a plant, wherein the plurality of parameters represents portions of the plant, and wherein at least two parameters of the plurality of parameters represent a plurality of petals of the flower; and
displaying a petal of the plurality of petals on the display screen, wherein the petal is associated with a number that corresponds to a measured value of a respective parameter of the plurality of parameters.

14. The non-transitory computer-readable medium of claim 13, wherein a size of the petal corresponds to the measured value of the respective parameter of the plurality of parameters.

15. The non-transitory computer-readable medium of claim 13, wherein the operations further comprise:
prepare second image data;
generate based on the second image data the second image of the plant; and
compare the second image with the first image.

16. The non-transitory computer-readable medium of claim 13, wherein the operations further comprise:
receive data representative of at least one user life habit;
prepare second image data; and
generate, based on the second image data, the image of roots of the plant, wherein the at least one user life habit represents portions of the roots.

* * * * *